United States Patent
Crofoot et al.

(10) Patent No.: US 10,918,587 B2
(45) Date of Patent: Feb. 16, 2021

(54) LONG LASTING COSMETIC COMPOSITION COMPRISING SILICONE ELASTOMER

(71) Applicant: DOW SILICONES CORPORATION, Midland, MI (US)

(72) Inventors: Mary Kay Crofoot, Freeland, MI (US); Kimmai Thi Nguyen, Midland, MI (US); Kenneth E. Zimmerman, Midland, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 16/492,045

(22) PCT Filed: Mar. 8, 2018

(86) PCT No.: PCT/US2018/021556
§ 371 (c)(1),
(2) Date: Sep. 6, 2019

(87) PCT Pub. No.: WO2018/165434
PCT Pub. Date: Sep. 13, 2018

(65) Prior Publication Data
US 2020/0323765 A1    Oct. 15, 2020

Related U.S. Application Data

(60) Provisional application No. 62/468,909, filed on Mar. 8, 2017.

(51) Int. Cl.
*A61K 8/896*   (2006.01)
*A61Q 19/00*   (2006.01)

(52) U.S. Cl.
CPC .............. *A61K 8/896* (2013.01); *A61Q 19/00* (2013.01)

(58) Field of Classification Search
None
See application file for complete search history.

(56) References Cited

U.S. PATENT DOCUMENTS

| 5,981,680 A | 11/1999 | Petroff et al. |
| 6,051,216 A | 4/2000 | Barr et al. |
| (Continued) | | |

FOREIGN PATENT DOCUMENTS

| EP | 1854451 B1 | 4/2011 |
| FR | 2918273 B1 | 8/2010 |
| (Continued) | | |

OTHER PUBLICATIONS

International Search Report for PCT/US2018/021556 dated May 28, 2018, 9 pages.
(Continued)

*Primary Examiner* — Melissa S Mercier
(74) *Attorney, Agent, or Firm* — Warner Norcross + Judd LLP

(57) ABSTRACT

A composition is provided that includes an elastomer and an additive. The additive stabilizes the elastomer, although it may be useful for an alternate or additional purpose. The elastomer can have a moiety according to the general formula: A-B-A or B-A-B. Each A independently comprises a polysiloxane moiety having at least two siloxy (Si—O) groups. Each B independently comprises a moiety, or a precursor thereof, having at least one carboxyl group. B is bonded to a silicon atom in A. The elastomer may comprise the reaction product of a reaction of: a first component having at least one reactive group; a second component having at least one reactive group; and a third component having at least two reactive groups reactive with the reactive groups of the first and second components. In addition, a
(Continued)

cosmetic composition is provided that includes the elastomer, the additive, and at least one cosmetic component.

12 Claims, 2 Drawing Sheets

(56) References Cited

U.S. PATENT DOCUMENTS

| | | | |
|---|---|---|---|
| 6,353,076 B1 | 3/2002 | Barr et al. |
| 6,451,295 B1 | 9/2002 | Cai et al. |
| RE38,116 E | 5/2003 | Petroff et al. |
| 6,569,955 B1 | 5/2003 | Brewer et al. |
| 6,958,155 B2 | 10/2005 | Lu et al. |
| 7,601,179 B2 | 10/2009 | Allard et al. |
| 7,611,544 B2 | 11/2009 | Allard et al. |
| 7,758,848 B2 | 7/2010 | Lu et al. |
| 7,790,148 B2 | 9/2010 | Bui et al. |
| 7,790,827 B2 | 9/2010 | Nguyen et al. |
| 2003/0082129 A1 | 5/2003 | Buckingham et al. |
| 2005/0158260 A1 | 7/2005 | Ferrari et al. |
| 2006/0104923 A1 | 5/2006 | Shah et al. |
| 2006/0193801 A1 | 8/2006 | Blin et al. |
| 2007/0041928 A1 | 2/2007 | Chen et al. |
| 2007/0128233 A1 | 6/2007 | Lu et al. |
| 2008/0171008 A1 | 7/2008 | Bui |
| 2009/0010868 A1 | 1/2009 | Ilekti et al. |
| 2010/0233114 A1 | 9/2010 | DeGeorge et al. |
| 2011/0306679 A1 | 12/2011 | Perruna et al. |
| 2012/0052030 A1 | 3/2012 | MacDermott et al. |
| 2013/0253072 A1 | 9/2013 | McDermott et al. |
| 2016/0194456 A1 | 7/2016 | Kadlec et al. |
| 2016/0199286 A1 | 7/2016 | Crofoot et al. |
| 2016/0200876 A1 | 7/2016 | Kadlec et al. |

FOREIGN PATENT DOCUMENTS

| | | | | |
|---|---|---|---|---|
| FR | 2918272 B1 | 9/2010 | | |
| FR | 2967910 A1 | 6/2012 | | |
| JP | 2008156242 A | 7/2008 | | |
| WO | 2007054492 A1 | 5/2007 | | |
| WO | 2007054494 A1 | 5/2007 | | |
| WO | 2007054830 A2 | 5/2007 | | |
| WO | 2009086036 A1 | 7/2009 | | |
| WO | 2012035513 A1 | 3/2012 | | |
| WO | 2015066161 A1 | 5/2015 | | |
| WO | 2015066165 A1 | 5/2015 | | |
| WO | 2015066199 A1 | 5/2015 | | |
| WO | WO-2015066199 A1 * | 5/2015 | ............. | A61K 8/342 |
| WO | 2015167963 A1 | 11/2015 | | |
| WO | 2016164292 A1 | 10/2016 | | |

OTHER PUBLICATIONS

Machine assisted English translation of FR2918272A1 obtained from https://worldwide.espacenet.com on Sep. 6, 2019, 41 pages.
Machine assisted English translation of FR2918273A1 obtained from https://worldwide.espacenet.com on Sep. 6, 2019, 51 pages.
Machine assisted English translation of JP2008156242A obtained from https://worldwide.espacenet.com on Sep. 6, 2019, 44 pages.
Machine assisted English translation of FR2967910A1 obtained from https://worldwide.espacenet.com on Sep. 6, 2019, 54 pages.

* cited by examiner

LONG LASTING COSMETIC COMPOSITION COMPRISING SILICONE ELASTOMER

CROSS-REFERENCE TO RELATED APPLICATIONS

This application is the National Stage of International Application No. PCT/US2018/021556 filed on 8 Mar. 2018, which claims priority to and all advantages of U.S. Provisional Pat. Appl. No. 62/468,909 filed on 8 Mar. 2017, the contents of which are hereby incorporated by reference.

This application claims priority to and all advantages of U.S. Provisional Pat. Appl. No. 62/468,909 filed on 8 Mar. 2017, the content of which is hereby incorporated by reference in its entirety.

This disclosure relates to compositions comprising an elastomer and an additive; to cosmetic compositions comprising the elastomer, the additive, and at least one cosmetic component optionally in a cosmetically acceptable medium; and to methods of making such compositions.

Silicone elastomers are rheology modifiers which may also positively impact the sensory profile of cosmetic compositions. There remains an opportunity to improve substantivity of elastomers on keratinous substrates. There also remains an opportunity to provide improved compositions, such as improved cosmetic compositions, and improved methods of forming such compositions.

SUMMARY OF THE INVENTION

This disclosure relates to compositions comprising elastomers and additives. In particular, this disclosure relates to compositions that include an elastomer and an additive, and to cosmetic compositions comprising the elastomers and additives. This disclosure also relates to cosmetic compositions that include the elastomer, the additive, and at least one cosmetic component optionally in a cosmetically acceptable medium.

In various embodiments, the elastomer has a moiety according to the general formula: A-B-A or B-A-B. Each A independently comprises a polysiloxane moiety having at least two siloxy (Si—O) groups. Each B independently comprises a moiety, or a precursor thereof, having at least one carboxyl group. B is bonded to a silicon atom in A.

In certain embodiments, the elastomer has at least two siloxy groups and at least one carboxyl group and is the reaction product of a reaction of a first component, a second component, and a third component. The first component has at least one reactive group. The second component also has at least one reactive group. The third component has at least two reactive groups reactive with the reactive groups of the first and second components for linking (e.g. cross-linking) the first component to the second component.

In certain of these embodiments, the at least one reactive group of the first component and the second components are independently selected from a hydroxyl group or an amine group and the at least two reactive groups of the third component are anhydride groups. In other embodiments, the at least one reactive group of the first component and the second component are anhydride groups and the at least two reactive groups of the third component are hydroxyl groups or amine groups.

The compositions of this disclosure are useful for a variety of end applications, and are not limited to any particular one. Examples of suitable applications include use in personal care, household care, and beauty care products. In embodiments having free carboxyl groups, the compositions can also be used for modifying organic resins or fibers and surface-treating powder. The treated surface shows high affinity with an unctuous agent. Particularly, dispersivity of powder is significantly improved. Therefore, the compositions can be useful for applications where high dispersivity of a powder is required, e.g., cosmetics such as skincare and makeup products, and coatings. The compositions can also be used to enhance the aesthetics of personal care formulations for skin care and healthcare by providing a unique sensory profile upon application. The compositions can provide sensory characteristics such as a velvety, silky, or powdery feel. In addition, the compositions can be used for providing rheology modification to personal care (e.g. skin, sun, cosmetic, etc.) and healthcare formulations. The compositions also have excellent formulation versatility. Without being bound or limited to any particular theory, it is thought that potential benefits provided by, or attributable to, the compositions include, but are not limited to, one or more of the following: film forming, substantivity, durability, pigment/particle suspension and/or modification, long lasting/wear, additional chemistry, actives (e.g. drug) or inactives (e.g. fragrance) delivery/release (e.g. to skin), and combinations thereof.

DETAILED DESCRIPTION OF THE INVENTION

Figure 1:
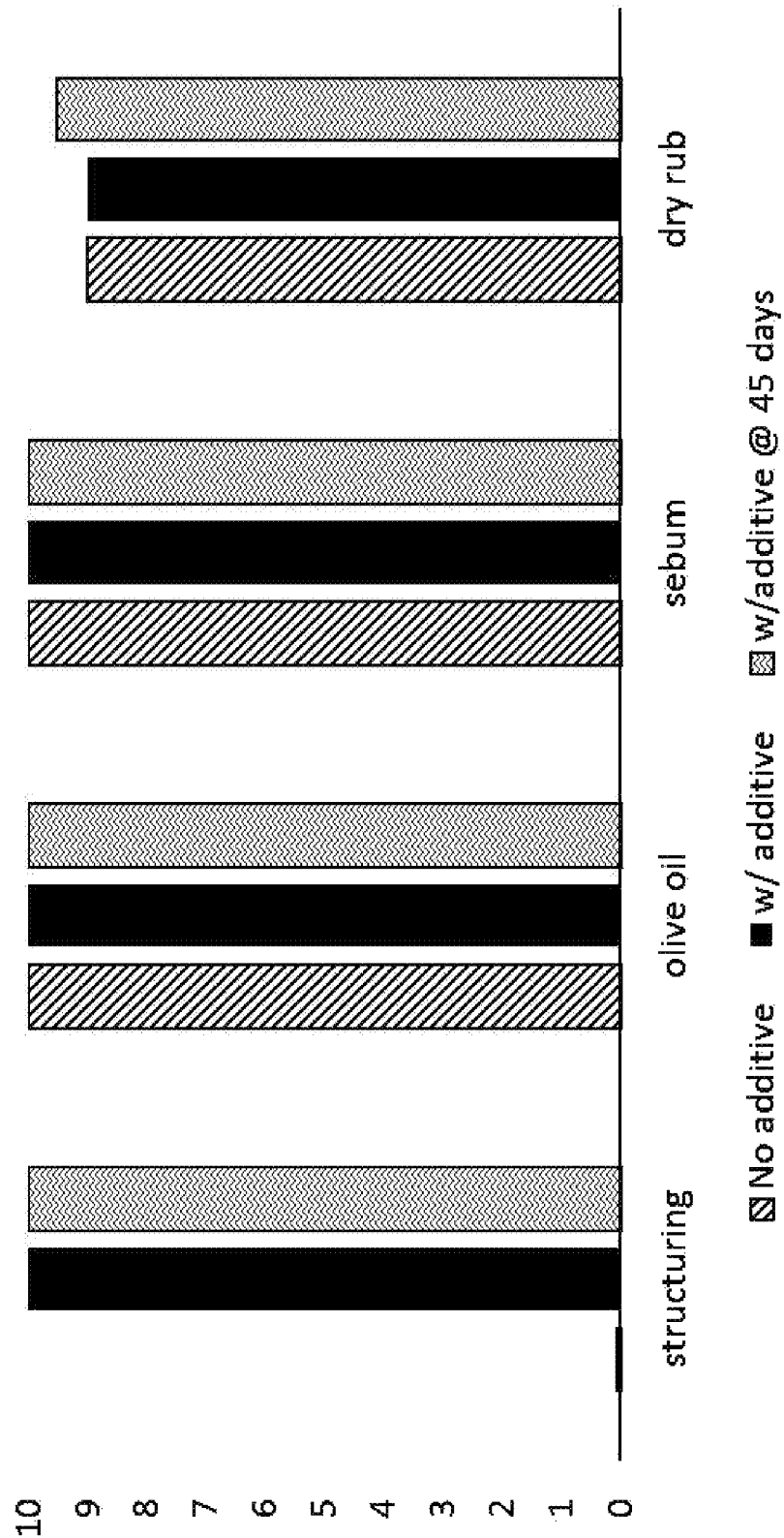
FIG. 1 is a column chart illustrating structuring and durability of pigmented elastomers with or without an additive.

Disclosed herein are compositions that include an elastomer and an additive for stabilizing the elastomer. Also disclosed herein are cosmetic compositions that include the elastomer, the additive, and at least one cosmetic component optionally in a cosmetically acceptable medium.

Cosmetic compositions include those compositions which are intended to be placed in contact with the external parts of the human body (skin (epidermis), hair system, nails, mucosa, etc., also referred to as "keratinous substrates") or with the teeth and the mucous membranes of the oral cavity with a view exclusively or mainly to cleaning them, perfuming them, changing their appearance, protecting them, keeping them in good condition or correcting body odors. In some instances, cosmetic compositions may also include health care compositions. Cosmetic applications, and in some instances health care applications, include skin care, sun care, hair care, or nail care applications.

Elastomer

The elastomer can be of various types. In general, the elastomer is a siloxane-based elastomer, which may also be referred to as a polysiloxane-based elastomer. Examples of suitable elastomers and methods of forming such elastomers include, but are not limited to, those described in US Pat. App. Pub. Nos. 2016/0194456, 2016/0199286, 2016/0200876, and 2017/0065514; and U.S. Pat. Nos. 9,822,221 and 9,714,323; the disclosures of which are hereby incorporated by reference in their entirety. In these publications/patents, suitable elastomers for this disclosure may also be referred to as cross-linked compositions or reaction products.

In various embodiments, the elastomer has a moiety according to the general formula: A-B-A or B-A-B, wherein each A independently comprises a polysiloxane moiety having at least two siloxy (Si—O) groups and wherein each B independently comprises a moiety, or a precursor thereof, having at least one, optionally at least two carboxyl groups, and wherein B is bonded to a silicon atom in A. The elastomer may also be referred to as a carboxy elastomer, a carboxy functional elastomer, or a carboxylic acid functional elastomer.

In certain embodiments, the elastomer has at least two siloxy (Si—O) groups and at least one, optionally at least two, carboxyl groups and is the reaction product of a reaction of: a first component having at least one reactive group; a second component having at least one reactive group; and a third component having at least two reactive groups reactive with the reactive groups of the first and second component for linking the first component to the second component.

In certain of these embodiments, the reactive groups of the first and second component are independently selected from a hydroxyl group or an amine group and the reactive groups of the third component are anhydride groups. In more specific related embodiments, the first and second components are selected from siloxanes having at least one hydroxyl group or organic alcohols having at least one hydroxyl group and the third component is a siloxane having at least two terminal anhydride groups. In other more specific related embodiments, the first and second components are selected from siloxanes having at least one amine group or organic amines having at least one amine group and the third component is a siloxane having at least two pendant anhydride groups.

In still other embodiments, the reactive groups of the first and second component are anhydride groups and the reactive groups of the third component are hydroxyl groups or amine groups. In more specific related embodiments, the first and second components are siloxanes and the anhydride groups are pendant. In certain of these embodiments, the third component is selected from i) an organic polyol having at least two hydroxyl groups; ii) a third siloxane having at least two hydroxyl groups; iii) an organic polyamine having at least two amine groups; or iv) a third siloxane having at least two amine groups.

In certain embodiments, each of the first and second reactive components can be chemically (or physically) the same, such as two separate molecules of the same reactive component (or type). For example, the first and second reactive components can be provided together, such as in an "A-part" (or A-side) of a system for forming the elastomer. Alternatively, the first and second reactive components can be provided separately, especially when they are different from each other. This may be useful for formulation purposes. However, separation is not required, as the first and second reactive components are typically inert with respect to each other.

The third reactive component can be provided separate from the first and second reactive component, such as in a "B-part" (or B-side) of a system for forming the elastomer. If the elastomer, or cosmetic composition, includes one or more optional additives, the additive(s) can be included with either of, each of, or a combination of, the system parts. The system may include more than two parts. Optionally, various types of conventional additives can be utilized depending on, for example, the end use of cosmetic composition. This disclosure is not limited to any particular arrangement of the system, system parts, or to any particular additive or additives.

In certain embodiments, the siloxanes used to form the elastomers consist of siloxane bonds (Si—O—Si) within each of their backbones. Alternatively, each of the siloxanes may include siloxane bonds separated by one or more bivalent groups, e.g. a —$CH_2$— linking group. Further examples of suitable bivalent groups include polyether groups, e.g. a —$CH_2CH_2O$— linking group (i.e., an EO group), a —$CH(CH_3)CH_2O$— linking group (i.e., a PO group), etc. Combinations of different bivalent groups may be present within each of their backbones. Each of the bivalent groups may be singular or repeated, e.g. 2 times, 5 times, 10 times, >10 times, etc. In certain embodiments, the first and second siloxanes are free of polyether groups.

In various embodiments, each of the siloxanes comprise at least one [$SiR_2$—O—] unit ("D" or $R_2SiO_{2/2}$ units). In further embodiments, each of the siloxanes has repeating D units, which generally constitute linear portions of the siloxanes. In yet further embodiments, each of the siloxanes has terminal $R_3SiO_{1/2}$ ("M") units. In these embodiments, R is an independently selected substituted or unsubstituted hydrocarbyl group.

In certain embodiments, each of the siloxanes described herein may optionally be branched, partially branched, and/or may include a resinous portion having a three-dimensional networked structure. In such embodiments, the respective siloxane may further comprise $RSiO_{3/2}$ ("T") units and/or $SiO_{4/2}$ ("Q") units. Branching of the siloxane, or the resinous portion, if present, can be attributable to the presence of T and/or Q units. Branching may also be attributable to side groups of one or more D units. In various embodiments, the siloxanes are free of T units, Q units, or both T and Q units. Where more than one siloxane is described, the siloxanes can be the same or different, e.g. one is linear and one is branched, both are branched, both are linear, etc.

The amount of elastomer in the cosmetic compositions may vary. In certain embodiments, the elastomer is present in an amount of from about 0.1% to about 95%, from about 0.2% to about 50%, or from about 0.5% to about 25%, by weight, relative to the total weight (or 100 parts by weight) of the cosmetic composition.

In certain embodiments having free carboxyl groups (e.g. after a ring-opening reaction), the elastomer has a carboxyl equivalent of from 100 to 50,000, from 500 to 10,000, or from 500 to 5,000, g/mol. For good handling property, the elastomer can have a viscosity of from 10 to 1,000,000, or from 10 to 100,000, mm²/sec.

In certain embodiments, a non-functionalized resin (i.e., one lacking reactive groups) is utilized with and/or in the elastomer. In these embodiments, at least a portion of the non-functionalized resin is trapped within the polymeric network during cure of the elastomer. Such non-functionalized resins can be useful for providing chemical and/or physical modifications to the elastomer.

Various non-limiting, more specific, embodiments of the elastomer of this disclosure (labeled as Elastomers 1-8), in accordance with the general embodiments above, as well as the description of the various cosmetic components that may also be included, are described below. Combinations of the components for each of Elastomers 1-8 described below can be utilized to form further elastomers, and thus compositions, not specifically elucidated herein.

Elastomer 1—Reaction Product of First and Second Siloxanes Having Pendant Anhydride Group(s) and Organic Polyol(s)

In a first embodiment, the elastomer ("Elastomer 1") comprises the reaction product of a reaction of a first siloxane, a second siloxane, and at least one organic polyol. In further embodiments, Elastomer 1 consists essentially of, optionally consists of, the reaction product of the first siloxane, second siloxane, and organic polyol(s). In certain embodiments, Elastomer 1 can include the further reaction product of one or more siloxanes in addition to, and different from, the first and second siloxanes.

Each of the first and second siloxanes has at least one, optionally at least two, pendant anhydride group(s). In various embodiments, each of the first and second siloxanes independently has from 1 to 25, 2 to 20, 3 to 15, 4 to 14, 5 to 12, 6 to 10, 7, 8, or 9, pendent anhydride group(s). Pendant groups may also be referred to as side groups, and are different from terminal groups (sometimes referred to as end groups). In various embodiments, each of the first and second siloxanes is free of terminal anhydride groups. In certain embodiments, each of the anhydride groups is directly bonded to an intervening atom or linkage that is directly bonded to a silicon atom. The anhydride groups are useful for reaction with the organic polyol, and can also impart additional functionality to Elastomer 1. It is thought that potential benefits provided by, or attributable to, the anhydride groups include, but are not limited to, film forming, substantivity, durability, pigment/particle suspension and/or modification, long lasting/wear, additional chemistry, actives (e.g. drug) or inactives (e.g. fragrance) delivery/release, hydrophilicity, reactivity, compatibility, polarity, and combinations thereof. In certain embodiments, the anhydride groups can provide free carboxyl groups, which can also provide benefits and/or be available for a subsequent, non-limiting reaction. For example, at least some of the anhydride groups are not reacting during the cross-linking reaction. Such anhydride groups may later react with water to provide carboxyl groups. In other embodiments, Elastomer 1 may have one or more free anhydride groups for a subsequent, non-limiting reaction.

The organic polyol has at least two hydroxyl groups reactive with the pendant anhydride groups of the first and second siloxanes. Each of the hydroxyl groups can be pendant or terminal. In various embodiments, the organic polyol has two hydroxyl groups. In further embodiments, the organic polyol has two terminal hydroxyl groups and is free of pendant hydroxyl groups. Each of the hydroxyl groups can be directly bonded to a carbon atom, or to an intervening atom or linkage that is directly bonded to a carbon atom. Each of the hydroxyl groups can be primary, secondary, or tertiary, optionally primary or secondary, optionally primary. The hydroxyl groups are useful for reaction with the first and second siloxanes, and can also impart additional functionality to Elastomer 1. In various embodiments, all of the hydroxyl groups of the organic polyol cross-link with anhydride groups of the first and second siloxanes to form linkages (e.g. ester cross-links). Some amount of anhydride and/or carboxyl groups can remain free depending on the amount of hydroxyl groups present during reaction to form Elastomer 1. Such free groups can be useful for subsequent reaction(s), e.g. with another component of the composition, and/or can also interact with substrate surfaces, e.g. skin, leather, etc.

Each of the first and second siloxanes can be chemically (or physically) the same, such as two separate molecules of the same siloxane component (or type). For example, the first and second siloxanes can be provided together, such as in an "A-part" of a system for forming Elastomer 1 or provided separately, especially when they are different from each other. The organic polyol can be provided separate from the first and second siloxanes, such as in a "B-part" of a system for forming Elastomer 1.

In various embodiments, each of the first and second siloxanes comprise at least one [SiR$^1$R$^2$—O—] unit (i.e., D unit). In these embodiments, R$^1$ is an independently selected substituted or unsubstituted hydrocarbyl group. By "substituted," it is meant that one or more hydrogen atoms of the hydrocarbon may be replaced with atoms other than hydrogen (e.g. a halogen atom), or a carbon atom within the chain of R$^1$ may be replaced with an atom other than carbon, i.e., R$^1$ may include one or more heteroatoms within the chain, such as oxygen, sulfur, nitrogen, etc. Examples of suitable hydrocarbyl groups represented by R$^1$ include alkyl, aryl, alkenyl, alkaryl, and aralkyl, groups.

In certain embodiments, R$^1$ is an independently selected alkyl group. Suitable alkyl groups can be linear, branched, or cyclic. If present as R$^1$, the alkyl group generally has from 1 to 20, 1 to 15, 1 to 10, 1 to 6, 1 to 4, 1, or 2, carbon atoms, or any number of carbon atoms in between. Specific examples of suitable alkyl groups include methyl groups, ethyl groups, propyl groups, butyl groups, pentyl groups, etc. In specific embodiments, R$^1$ is a methyl group (i.e., —CH$_3$).

In various embodiments for Elastomer 1, R$^2$ is a pendant anhydride group of the following general formula (A):

(A)

R$^3$ is a divalent group. R$^3$ can be a hydrocarbylene, heterohydrocarbylene, or organoheterylene group. In various embodiments, R$^3$ is (CH$_2$)$_n$ where n is an integer selected from 1 to 30, 1 to 25, 1 to 20, 1 to 15, 1 to 10, 1 to 5, or 1 to 3, or any number/range in between. In specific embodiments, n is 1, 2, or 3.

In various embodiments, each of the first and second siloxanes is individually of the following general formula (B):

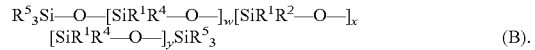

R$^5_3$Si—O—[SiR$^1$R$^4$—O—]$_w$[SiR$^1$R$^2$—O—]$_x$
[SiR$^1$R$^4$—O—]$_y$SiR$^5_3$     (B).

In further embodiments, each of the first and second siloxanes is individually of the following general formula (C):

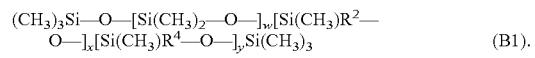

(CH$_3$)$_3$Si—O—[Si(CH$_3$)$_2$—O—]$_w$[Si(CH$_3$)R$^2$—
O—]$_x$[Si(CH$_3$)R$^4$—O—]$_y$Si(CH$_3$)$_3$     (B1).

Each of R$^1$ and R$^2$ is as described above. Examples of suitable groups for each of R$^4$ and R$^5$ are as described above for R$^1$. In certain embodiments, each R$^4$ is an independently selected alkyl group, aryl group, or polyether group. If R$^4$ is a polyether group, the polyether group generally terminates with an —OR$^6$ group. R$^6$ may be an alkyl group or aryl group, and there may be from 2 to 49, 2 to 24, 2 to 9, 2 to 4, or 2, ether linkages, or any number of ether linkages in between. In specific embodiments, R$^4$ is an independently selected alkyl group having from 2 to 20, 2 to 15, 2 to 10, 2 to 8, 4 to 6, 5, or 6, carbon atoms, or any number of carbon atoms in between. Without being bound or limited by any particular theory, it is thought that the organic compatibility of Elastomer 1, e.g. in a solvent, can be enhanced by having a long chain alkyl group on one or both of the first and second siloxane backbones, e.g. as $R^4$. In alternate embodiments, $R^4$ may be silicone side chain of the siloxane. The groups represented by subscripts w, x, and y, e.g. the groups having square brackets in formulas (B) and (B1), may be present in any order within the respective siloxane, including a different order than that which is represented above and throughout this disclosure. Moreover, these groups may be present in randomized or block form.

In certain embodiments, $R^4$ is either an alkyl group or a polyether group. Without being bound or limited to any particular theory, it is thought that the hydrophilic character of Elastomer 1 can be enhanced by having a polyether side chain (or chains) on one or both of the first and second siloxane backbones, e.g. as $R^4$. Each $R^5$ may be $R^1$. For example, each of $R^1$ and $R^5$ can be an alkyl group, e.g. a methyl group. In certain embodiments where free anhydride groups are desired after reaction, at least some of $R^4$ may be $R^2$.

In various embodiments, w is an integer selected from zero (0) to 1,000, 0 to 950, 0 to 750, 0 to 500, 0 to 400, 1 to 350, 1 to 300, 25 to 250, 50 to 200, 50 to 150, 75 to 125, 90 to 110, 90 to 100, or 90 to 95, or any number/range in between. In certain embodiments, w≥1, w≥2, w≥3, w≥4, w≥5, w≥25, w≥50, or w≥75, and/or w≤1000, w≤750, w≤500, w≤250, w≤150, or w≤100. In specific embodiments, w is 90, 91, 92, 93, 94, or 95. In further embodiments, x is an integer selected from 1 to 100, 1 to 75, 1 to 50, 1 to 25, 1 to 20, 1 to 15, or 1 to 10, or any number/range in between. In certain embodiments, x≥1, x≥2, x≥3, x≥1, x≥5, x≥10, x≥15, or x≥20, and/or x≤50, x≤40, x≤30, x≤20, x≤15, or x≤10. In specific embodiments, x is 2, 3, 4, 5, 6, 7, 8, 9, or 10. In further embodiments, y is an integer selected from 0 to 1,000, 0 to 950, 0 to 750, 0 to 500, 0 to 400, 1 to 350, 1 to 300, 1 to 250, 1 to 200, 1 to 150, 1 to 100, 1 to 75, 1 to 50, 1 to 25, 1 to 20, 1 to 15, or 1 to 10, or any number/range in between. In certain embodiments, y≥1, y≥2, y≥3, y≥4, y≥5, y≥10, y≥15, or y≥20, and/or y≤50, y≤40, y≤30, y≤20, y≤15, or y≤10. In specific embodiments, y is 1, 2, 3, 4, 5, 6, 7, 8, 9, or 10.

In various embodiments, w and y are not simultaneously 0. Said another way, in these embodiments, each of the first and second siloxanes include at least one D unit associated with each of the x units and at least one of the w and y units in formula (B) or (B1). In certain embodiments, the sum of w+x+y is from 25 to 1,500, 25 to 1,000, 25 to 900, 25 to 800, 25 to 700, 25 to 600, 25 to 500, 25 to 400, 25 to 300, 50 to 200, 75 to 150, 85 to 125, or 90 to 110, or any number/range in between. In these embodiments, x is as described above. Thus, each of the first and second siloxanes has at least one of the pendant anhydride groups, and can have other side groups based on the presence of one or more D units associated with w and y.

The organic polyol can be any type of polyol provided it has at least two hydroxyl groups reactive with the pendant anhydride groups of the first and second siloxanes. In this way, the organic polyol serves as a cross-linker between the first and second siloxanes to form Elastomer 1. Elastomer 1 may constitute just one moiety, or a plurality of moieties, imparted by the organic polyol depending on, for example, the number of pendant anhydride groups attributable to the first and second siloxanes. In certain embodiments, Elastomer 1 can include the further reaction product of one or more polyols in addition to, and different from, the organic polyol.

By "organic", it is generally meant that the organic polyol contains predominantly carbon, e.g. a carbon backbone. While carbon is present, other atoms may also be present, such as oxygen atoms, hydrogen atoms, nitrogen atoms, etc. In many embodiments, the organic polyol is free of silicon, e.g. one or more silicon atoms.

In various embodiments, the organic polyol ("polyol") is a diol (i.e., the polyol has two hydroxyl groups). Examples of suitable diols include, but are not limited to, methylene glycol, ethylene glycol, diethylene glycol, propylene glycol, dipropylene glycol, butane diol, bisphenol A, 1,4-butanediol, 1,3-propanediol, 1,5-pentanediol, 1,7-heptanediol, 1,2-hexanediol, triethylene glycol, tripropylene glycol neopentyl glycol, and combinations thereof. In other embodiments, the polyol is a triol (i.e., the polyol has three hydroxyl groups).

In many embodiments, the polyol has the following general formula: HO—$R^7$—OH. In these embodiments, $R^7$ is selected from alkyl, cycloalkyl, alkyl cycloalkyl, aromatic, and alkylaromatic diradicals. Such diradicals generally have up to 50, up to 40, up to 30, up to 20, or up to 10, carbon atoms, or any number of carbon atoms between 1 and 50. The carbon chain which makes up the backbone of the polyol may be straight chained or branched. In certain embodiments, the polyol may have ether, thio, or amine linkages in its main chain. In specific embodiments, $R^7$ is a hydrocarbylene group having from 1 to 10, 2 to 9, 3 to 8, 4 to 7, 5, or 6, carbon atom(s).

In certain embodiments, the polyol is a (poly)oxyalkylene compound. Suitable examples of such compounds include, but are not limited to, ethylene glycol, diethylene glycol, triethylene glycol, polyethylene glycol (e.g. having a molecular weight of 200 to 2,000), propylene glycol, dipropylene glycol, polypropylene glycol (e.g. having a molecular weight of 200 to 3,000), butylene glycol, dibutylene glycol, polybutylene glycol (e.g. having a molecular weight of 200 to 4,000), random copolymers and block copolymers of polyethylenepropylene glycol (e.g. having a molecular weight of 100 to 3,000), random copolymers and block copolymers of polyethylenebutylene glycol (e.g. having a molecular weight of 100 to 4,000), and combinations thereof.

In various embodiments, the polyol can comprise a polyester polyol, a polyether polyol, a polyether/ester polyol, or combinations thereof. Furthermore, the polyol may be selected from aliphatic polyols, cycloaliphatic polyols, aromatic polyols, heterocyclic polyols, and combinations thereof. Some examples of suitable polyols include, but are not limited to, glycol-initiated polyols, glycerine-initiated polyols, sucrose-initiated polyols, sucrose/glycerine-initiated polyols, trimethylolpropane-initiated polyols, and combinations thereof.

Suitable polyester polyols include hydroxyl-terminated reaction products of polyhydric alcohols, polyester polyols obtained by the polymerization of lactones, e.g. caprolactone, in conjunction with a polyol, and polyester polyols obtained by the polymerization of hydroxy carboxylic acids, e.g. hydroxy caproic acid. Polyesteramide polyols, polythioether polyols, polycarbonate polyols, polyacetal polyols, and polyolefin polyols may also be used.

Suitable polyether polyols include products obtained by the polymerization of a cyclic oxide, such as ethylene oxide (EO), propylene oxide (PO), butylene oxide (BO), and tetrahydrofuran in the presence of a polyfunctional initiator. Suitable initiator compounds contain a plurality of active hydrogen atoms, and include, but are not limited to, water, butanediol, ethylene glycol, propylene glycol, diethylene glycol, triethylene glycol, dipropylene glycol, ethanolamine, diethanolamine, triethanolamine, toluene diamine, diethyl toluene diamine, phenyl diamine, diphenylmethane diamine, ethylene diamine, cyclohexane diamine, cyclohexane dimethanol, resorcinol, bisphenol A, glycerol, trimethylolpropane, 1,2,6-hexanetriol, pentaerythritol, and combinations thereof. Some of these initiators may also be useful as the polyol itself. In specific embodiments, the polyol is a polyether diol. Combinations of different polyols can be utilized to form Elastomer 1.

In certain embodiments, Elastomer 1 is of the following general formula (D):

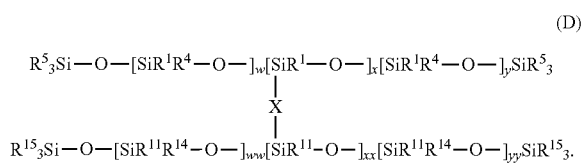

(D)

In formula (D), the upper and lower portions are attributable to the first and second siloxanes, which can be the same or different. Each of $R^1$, $R^4$, and $R^5$ is as described above. Each of subscripts w, x, and y are also as described above, and each of subscripts ww, xx, and yy can be the same as or different from each of w, x, and y, respectively. Each of $R^{11}$, $R^{14}$, and $R^{15}$ can be the same as or different from each of $R^1$, $R^4$, and $R^5$, respectively. Each $R^5$ may be $R^1$ and/or each $R^{15}$ may be $R^{11}$. The groups represented by subscripts w, ww, x, xx, y, and yy, e.g. the groups having square brackets in formula (D), may be present in any order within Elastomer 1, including a different order than that which is represented above and throughout this disclosure. Moreover, these groups may be present in randomized or block form.

Each of $R^{11}$, $R^{14}$, and $R^{15}$ can be an independently selected substituted or unsubstituted hydrocarbyl group. Examples of suitable groups for $R^{11}$, $R^{14}$, and $R^{15}$ are as described above for $R^1$, $R^4$, and $R^5$.

Examples of suitable subscripts ww, xx, and yy are as described above for w, x, and y, respectively. In various embodiments, ww and yy are not simultaneously 0. In certain embodiments, the sum of ww+xx+yy is from 25 to 1,500, 25 to 1,000, 25 to 900, 25 to 800, 25 to 700, 25 to 600, 25 to 500, 25 to 400, 25 to 300, 50 to 200, 75 to 150, 85 to 125, or 90 to 110, or any number/range in between. In these embodiments, xx is as described above.

The middle (or "X") portion of formula (D) is attributable to the polyol, as well as the anhydride groups of the first and second siloxanes, and is according to the following general formula (E):

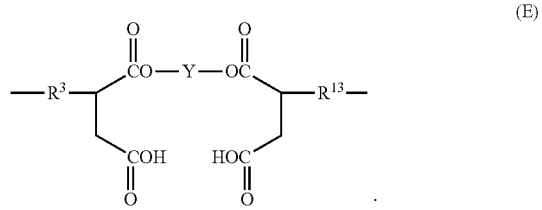

(E)

$R^3$ is as described above and $R^{13}$ is a divalent group. $R^{13}$ may be the same or different than $R^3$. Examples of suitable groups for $R^{13}$ are as described above for $R^3$.

Each Y is a divalent group, such as an organic divalent group, which is attributable to the polyol. During formation of Elastomer 1, the polyol had two hydroxyl groups, e.g. terminal hydroxyl groups, which reacted with pendant anhydride groups of the first and second siloxanes to form linkages between the siloxanes and polyol. As shown in formula (E), Elastomer 1 has at least two carboxyl groups. The possibility of such carboxyl groups is described below. In other embodiments (not shown), another molecule of the polyol has reacted between the two carboxyl groups to form another —Y— linkage (i.e., the two carboxyl groups in formula (E) are gone).

Y can be of any structure attributable to the polyol. In various embodiments, Y comprises at least one of a hydrocarbylene, heterohydrocarbylene, or organoheterylene group. In certain embodiments, Y is a hydrocarbylene group having from 1 to 50, 1 to 40, 1 to 20, 1 to 20, 1 to 10, 2 to 9, 3 to 8, 4 to 7, 5, or 6, carbon atom(s), or any number of carbon atoms in between. Further examples of suitable groups for Y are as described with the $R^7$ groups of polyol. In certain embodiments where the polyol is free of polyether groups, the Y is also free of polyether groups.

In certain embodiments, Elastomer 1 can be formed with a supplemental cross-linker in addition to the polyol. Examples of suitable supplemental cross-linkers include polyols, polyamines, polyepoxides, and combinations thereof. Suitable supplemental cross-linkers, as well as other optional components that can be used to form, and/or be used in combination with Elastomer 1 are described in U.S. Pat. Nos. 5,444,139 and 8,026,330; and US Pat. App. Pub. No. 2012/0040931; which are incorporated herein by reference in their entirety. Further suitable supplemental cross-linkers and siloxanes that can be used to form, and/or be used in combination with, Elastomer 1, are described in US Pat. App. Pub. Nos. 2016/0194456, 2016/0199286, 2016/0200876, and 2017/0065514; and U.S. Pat. Nos. 9,822,221 and 9,714,323; which are incorporated herein by reference in their entirety. Combinations of cross-linkers, supplemental cross-linkers, (functional and/or non-functional) resins, and/or siloxanes, can be utilized.

The first siloxane, second siloxane, and polyol can be reacted in various amounts to form Elastomer 1. Based on the number of hydroxyl groups provided by the polyol, relative to the number of anhydride groups provided by the first and second siloxanes, the reactants can be utilized in a 1:1 stoichiometric ratio. For example, one hydroxyl group can be present for every one of the anhydride groups present. Alternatively, the polyol can be utilized in a stoichiometric excess relative to the first and second siloxanes. Conversely, the first and second siloxanes can be utilized in a stoichiometric excess relative to the polyol. Such situations may also be referred to as over-indexing or under-indexing the ring-opening reaction, with an index of 1.0 (or 100) indicating that there is a stoichiometric amount of hydroxyl groups present to react with the amount of anhydride groups present (1:1). The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 1 can include various functional groups for subsequent reaction, including free carboxyl groups, and possibly even free anhydride groups and/or free hydroxyl groups, or combinations thereof. In many embodiments, Elastomer 1 does not include free hydroxyl groups. In certain embodiments, Elastomer 1 has at least two carboxyl groups. This disclosure is not limited to any particular subsequent reaction or use of such free functional groups. Various degrees of cross-linking can be present in Elastomer 1 based on the index utilized to form Elastomer 1, from various degrees of partial cross-linking to full cross-linking.

Elastomer 2—Reaction Product of First and Second Siloxanes Having Pendant Anhydride Group(s) and Organic Polyamine(s)

In a second embodiment, the elastomer ("Elastomer 2") comprises the reaction product of a first siloxane, a second siloxane, and at least one organic polyamine. In further embodiments, Elastomer 2 consists essentially of, optionally consists of, the reaction product of the first siloxane, second siloxane, and organic polyamine(s). In certain embodiments, Elastomer 2 can include the further reaction product of one or more siloxanes in addition to, and different from, the first and second siloxanes. The first and second siloxanes are as described above for Elastomer 1. The organic polyamine can be provided separate from the first and second siloxanes, such as in a "B-part" of a system for forming Elastomer 2.

The organic polyamine has at least two amine groups reactive with the pendant anhydride groups of the first and second siloxanes. Each of the amine groups can be pendant or terminal. In various embodiments, the organic polyamine has two amine groups. In further embodiments, the organic polyamine has two terminal amine groups and is free of pendant amine groups. Each of the amine groups can be directly bonded to a carbon atom, or to an intervening atom or linkage that is directly bonded to a carbon atom. Each of the amine groups can be primary or secondary, optionally primary. The amine groups are useful for reaction with the first and second siloxanes, and can also impart additional functionality to Elastomer 2. In various embodiments, all of the amine groups of the polyamine cross-link with anhydride groups of the first and second siloxanes to form linkages. Some amount of anhydride and/or carboxyl groups can remain free depending on the amount of amine groups present during reaction to form Elastomer 2.

The organic polyamine can be any type of polyamine provided it has at least two amine groups reactive with the pendant anhydride groups of the first and second siloxanes. In this way, the organic polyamine serves as a cross-linker between the first and second siloxanes to form Elastomer 2. Elastomer 2 may constitute just one moiety, or a plurality of moieties, imparted by the organic polyamine depending on, for example, the number of pendant anhydride groups attributable to the first and second siloxanes. In certain embodiments, Elastomer 2 can include the further reaction product of one or more polyamines in addition to, and different from, the organic polyamine.

By "organic", it is generally meant that the organic polyamine contains predominantly carbon, e.g. a carbon backbone. While carbon is present, other atoms may also be present, such as oxygen atoms, hydrogen atoms, nitrogen atoms, etc. In many embodiments, the organic polyamine is free of silicon, e.g. one or more silicon atoms.

In various embodiments, the organic polyamine ("polyamine") is a diamine (i.e., the polyamine has two amine groups). Examples of suitable diamines include, but are not limited to, ethylenediamine, toluene diamine, 1,3-diaminpropane, putrescine, cadaverine, hexamethylenediamine, 1,2-diaminopropane, diphenylethylenediamine, diaminocyclohexane, xylylenediamines, phenylenediamines, benzidine, spermidine, spermine, toluene diamine, aminobenzylamines, and combinations thereof. In other embodiments, the polyamine is a triamine (i.e., the polyamine has three amine groups). In specific embodiments, the polyamine is a polyether diamine.

In many embodiments, the polyamine has the following general formula: $R_2N—R^{17}—NR_2$. Each R is independently a hydrogen atom (H) or $R^1$, optionally a H. $R^1$ can be as described above. In these embodiments, $R^{17}$ is selected from alkyl, cycloalkyl, alkyl cycloalkyl, aromatic, and alkylaromatic diradicals. Such diradicals generally have up to 50, up to 40, up to 30, up to 20, or up to 10, carbon atoms, or any number of carbon atoms between 1 and 50. The carbon chain which makes up the backbone of the polyamine may be straight chained or branched. In certain embodiments, the polyamine may have ether, thio, or amine linkages in its main chain. In specific embodiments, $R^{17}$ is a hydrocarbylene group having from 1 to 10, 2 to 9, 3 to 8, 4 to 7, 5, or 6, carbon atom(s).

In certain embodiments, the polyamine is a (poly)oxyalkylene compound. Suitable examples of such compounds include, but are not limited to, ethylene diamine, diethylene diamine, polyethylene diamine (e.g. having a molecular weight of 200 to 2,000), propylene diamine, dipropylene diamine, polypropylene diamine (e.g. having a molecular weight of 200 to 3,000), butylene diamine, dibutylene diamine, polybutylene diamine (e.g. having a molecular weight of 200 to 4,000), and combinations thereof.

In various embodiments, the polyamine can comprise a polyester polyamine, a polyether polyamine, a polyether/ester polyamine, or combinations thereof. Furthermore, the polyamine may be selected from aliphatic polyamines, cycloaliphatic polyamines, aromatic polyamines, heterocyclic polyamines, and combinations thereof. Some examples of suitable polyamines include, but are not limited to, glycol-initiated polyamines, glycerine-initiated polyamines, sucrose-initiated polyamines, sucrose/glycerine-initiated polyamines, trimethylolpropane-initiated polyamines, and combinations thereof.

Further examples of suitable polyamines include, but are not limited to, divalent and higher polyvalent primary or secondary, aliphatic, araliphatic, cycloaliphatic or aromatic amines. Specific examples include among others, 4-aminobenzylamines, 4,4'-diaminodicyclohexylmethane, phenylene diamines, etc. Polyamines such as diethylenetriamine, triethylenetetramine, diethylenepropylamine, N-(2-hydroxyethyl) diethylenetriamine, N,N'-di(2-hydroxyethyl) diethylenetriamine, m-phenylenediamine, methylenedianiline, aminoethyl piperazine, 4,4-diaminodiphenyl sulfone, benzyldimethylamine, dicyandiamide, and 2-methylimidazole, and triethylamine, can also be utilized.

Suitable aromatic diamines such as a diaminodiphenylsulfone, a methylenedianiline such as 4,4'-methylenedianiline, a diaminodiphenylether, benzidine, 4,4'-thiodianiline, 4-methoxy-6-m-phenylenediamine, 2,6-diaminopyridine, 2,4-toluenediamine, and dianisidine can be utilized. Further examples include alicyclic amines, such as menthane diamine and heterocyclic amines such as pyridine. In some cases, aliphatic amines such as secondary alkylamines can be utilized.

Further suitable diamines include, but are not limited to, the isomeric phenylene diamines, 4,4'-diaminobenzophenone, bis(4-amino)diphenyl ether and 2,2-bis(4-aminophenyl)propane. Other examples of suitable amines include alcohol amines, such as ethanol amine and diethanol amine, as well as amino acids and peptides.

Further examples of suitable polyamines include, but are not limited to, m-phenylenediamine, p-phenylenediamine, 4,4'-diaminodiphenyl ether, 3,4'-diaminodiphenyl ether, 4,4'-diaminodiphenylsulfone, 3,3'-diaminodiphenylsulfone, 2,2'-ditrifluoromethyl-4,4'-diaminobiphenyl, 9,9-bis(4-aminophenyl)fluorene, 9,9-bis(4-mino-3-methylphenyl)fluorene, bis[4-(4-aminophenoxy)phenyl]sulfone, bis[4-(3-aminophenoxy)phenyl]sulfone, 2,2-bis[4-(4-aminophenoxy)phenyl]propane, 3-(methylamino)propylamine, and 2,2-bis(4-aminophenyl) hexafluoropropane. Other examples include alkyl amines, propyl amine, isobutyl amine, alkyleneoxide amines, EO amines, PO amines, BO amines, etc. Combinations of different polyamines can be utilized to form Elastomer 2.

In certain embodiments, Elastomer 2 is of the following general formula (F):

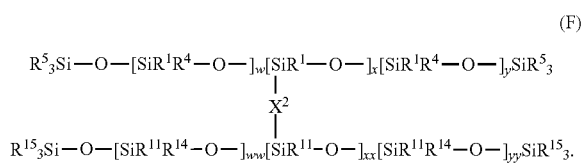

In formula (F), the upper and lower portions of Elastomer 2 are attributable to the first and second siloxanes. Each of $R^1$, $R^4$, $R^5$, $R^{11}$, $R^{14}$, and $R^{15}$, and subscripts w, x, y, ww, xx, and yy is as described above for Elastomer 1.

The middle (or "$X^2$") portion of formula (F) is attributable to the polyamine, as well as the anhydride groups of the first and second siloxanes, and is according to the following general formula (G):

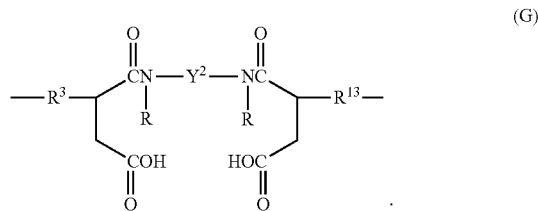

Each of $R^3$ and $R^{13}$ is as described above for Elastomer 1. Each R is independently H or $R^1$, optionally a H.

Each $Y^2$ is an organic divalent group, which is attributable to the polyamine. During formation of Elastomer 2, the polyamine had two amine groups, e.g. terminal amine groups, which reacted with pendant anhydride groups of the first and second siloxanes to form linkages between the siloxanes and polyamine. As shown in formula (G), Elastomer 2 has at least two carboxyl groups. In other embodiments (not shown), another molecule of the polyamine has reacted between the two carboxyl groups to form another —$Y^2$— linkage (i.e., the two carboxyl groups in formula (G) are gone).

$Y^2$ can be of any structure attributable to the polyamine. In various embodiments, $Y^2$ comprises at least one of a hydrocarbylene, heterohydrocarbylene, or organoheterylene group. In certain embodiments, $Y^2$ is a hydrocarbylene group having from 1 to 50, 1 to 40, 1 to 20, 1 to 20, 1 to 10, 1 to 5, 1 to 2, 1, or 2, carbon atom(s), or any number of carbon atoms in between. Further examples of suitable groups for $Y^2$ are as described with the $R^{17}$ groups of the polyamine. In certain embodiments where the polyamine is free of polyether groups, the $Y^2$ is also free of polyether groups.

In certain embodiments, Elastomer 2 can be formed with a supplemental cross-linker in addition to the polyamine. Examples of suitable supplemental cross-linkers are as described above for Elastomer 1.

The first siloxane, second siloxane, and polyamine can be reacted in various amounts to form Elastomer 2. Based on the number of amine groups provided by the polyamine, relative to the number of anhydride groups provided by the first and second siloxanes, the reactants can be utilized in a 1:1 stoichiometric ratio. For example, one amine group can be present for every one of the anhydride groups present. Alternatively, the polyamine can be utilized in a stoichiometric excess relative to the first and second siloxanes. Conversely, the first and second siloxanes can be utilized in a stoichiometric excess relative to the polyamine. Such situations may also be referred to as over-indexing or under-indexing the ring-opening reaction, with an index of 1.0 (or 100) indicating that there is a stoichiometric amount of amine groups present to react with the amount of anhydride groups present (1:1). The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 2 can include various functional groups for subsequent reaction, including free carboxyl groups, and possibly even free anhydride groups and/or free amine groups, or combinations thereof. In many embodiments, Elastomer 2 does not include free amine groups. In certain embodiments, Elastomer 2 has at least two carboxyl groups. Various degrees of cross-linking can be present in Elastomer 2 based on the index utilized to form Elastomer 2, from various degrees of partial cross-linking to full cross-linking.

Elastomer 3—Reaction Product of First and Second Siloxanes Having Pendant Anhydride Group(s) and Third Siloxane(s) Having at Least Two Hydroxyl Groups In a third embodiment, the elastomer ("Elastomer 3") comprises the reaction product of a first siloxane, a second siloxane, and at least one third siloxane. In further embodiments, Elastomer 3 consists essentially of, optionally consists of, the reaction product of the first, second, and third siloxanes. In certain embodiments, Elastomer 3 can include the further reaction product of one or more siloxanes in addition to, and different from, the first, second, and third siloxanes. The first and second siloxanes are as described above for Elastomer 1. The third siloxane can be provided separate from the first and second siloxanes, such as in a "B-part" of a system for forming Elastomer 3.

The third siloxane has at least two hydroxyl groups reactive with the pendant anhydride groups of the first and second siloxanes. Each of the hydroxyl groups can be pendant or terminal. In various embodiments, the third siloxane has two hydroxyl groups. In further embodiments, the third siloxane has two terminal hydroxyl groups and is free of pendant hydroxyl groups. Each of the hydroxyl groups can be directly bonded to a silicon atom, or to an intervening atom or linkage that is directly bonded to a silicon atom. Alternatively, each of the hydroxyl groups can be directly bonded to a carbon atom, or to an intervening atom or linkage that is directly bonded to a carbon atom. Each of the hydroxyl groups can be primary, secondary, or tertiary, optionally primary or secondary, optionally primary. The hydroxyl groups are useful for reaction with the first and second siloxanes, and can also impart additional functionality to Elastomer 3. In various embodiments, all of the hydroxyl groups of the third siloxane cross-link with anhydride groups of the first and second siloxanes to form linkages (e.g. ester cross-links). Some amount of anhydride and/or carboxyl groups can remain free depending on the amount of hydroxyl groups present during reaction to form Elastomer 3.

The third siloxane can be any type of siloxane provided it has at least two hydroxyl groups reactive with the pendant anhydride groups of the first and second siloxanes. In this way, the third siloxane serves as a cross-linker between the first and second siloxanes to form Elastomer 3. Elastomer 3 may constitute just one moiety, or a plurality of moieties, imparted by the third siloxane depending on, for example, the number of pendant anhydride groups attributable to the first and second siloxanes.

In various embodiments, the third siloxane comprises at least one D unit. In further embodiments, the third siloxane has repeating D units, which generally constitute linear portions of the siloxane. In various embodiments, the third siloxane is a carbinol siloxane or a carbinol polysiloxane.

In certain embodiments, the third siloxane is a polysiloxane of the following general formula (H):

Each $R^1$ is as described above for Elastomer 1—but $R^2$ is not. Specifically, each of $R^2$ and $R^{10}$ can be an independently selected substituted or unsubstituted hydrocarbyl group. Examples of suitable groups for $R^2$ and $R^{10}$ are as described above for $R^1$ and $R^4$. For example, at least one of $R^2$ and $R^{10}$ can be an alkyl group having from 1 to 20 carbon atoms or a polyether group. In alternate embodiments, at least one of $R^2$ and $R^{10}$ may be silicone side chain of the siloxane. The groups represented by subscripts a, b, and c, e.g. the groups having square brackets in formula (H), may be present in any order within the siloxane, including a different order than that which is represented above and throughout this disclosure. Moreover, these groups may be present in randomized or block form.

Each Z is a divalent group, and in various embodiments can independently comprise at least one of a hydrocarbylene, heterohydrocarbylene, or organoheterylene group. In certain embodiments, Z is a hydrocarbylene group having from 1 to 20, 1 to 10, 1 to 5, 1 to 2, 1, or 2, carbon atom(s), or any number of carbon atoms in between. Further examples of suitable groups for Z are as described with the optional bivalent groups of the first and second siloxanes, e.g. a —CH$_2$— linking group, an EO group, a PO group, etc., or combinations thereof. In certain embodiments, the third siloxane is free of polyether groups.

In various embodiments, Z comprises at least one structural unit selected from the group consisting of: $[(CH_2)_i]_k$; $[(CH_2)_iO]_k$; $[(CH_2)_i(CH)(CH_3)O]_k$; $[(CH_2)_i(CH)(CH_2)_j(CH_3)O]_k$; $[(CH)OH]_k$; $[(CH)(CH_2)_iOH]_k$; $[(CH_3)_2COH(CH_2)_i]_k$; $[(CH_3)(CH_2)_iCOH(CH_2)_j(CH_3)]_k$; and combinations thereof. These units may be modified or rearranged to allow for proper orientation and bonding of the respective Z units in formula (H). In various embodiments, i is an integer selected from 1 to 100, 1 to 75, 1 to 50, 1 to 25, 1 to 10, 1 to 5, or 1, or any number/range in between; j is an integer selected from 1 to 100, 1 to 75, 1 to 50, 1 to 25, 1 to 10, 1 to 5, or 1, or any number/range in between; and k is an integer selected from 1 to 100, 1 to 75, 1 to 50, 1 to 25, 1 to 10, 1 to 5, or 1, or any number/range in between. Examples of Z include structural units (or moieties) attributable to use of 4-penten-1-ol, 7-octen-1-ol, glycerol monoallyl ether, allyl xylitol, trimethylolpropane monoallyl ether, xylitol, pentaerythritol, triglycerol, and combinations thereof. In certain embodiments, Z can include one or more pendant functional (e.g. hydroxyl and/or amine) groups in addition to the terminal hydroxyl group attached thereto.

In various embodiments, a is an integer selected from 0 to 1,000, 1 to 950, 2 to 750, 3 to 500, 4 to 400, 5 to 300, 6 to 200, 7 to 100, 8 to 75, 9 to 50, 10 to 25, 11 to 20, or 12 to 15, or any number/range in between. In further embodiments, b is an integer selected from 1 to 1,000, 5 to 950, 10 to 750, 15 to 500, 25 to 400, 35 to 300, 45 to 200, or 50 to 100, or any number/range in between. In further embodiments, c is an integer selected from 0 to 1,000, 1 to 950, 2 to 750, 3 to 500, 4 to 400, 5 to 300, 6 to 200, 7 to 100, 8 to 75, 9 to 50, 10 to 25, 11 to 20, or 12 to 15, or any number/range in between. In various embodiments, each d is independently 0 or 1. In specific embodiments, at least one d is 1, or both of d are 1.

In certain embodiments, the third siloxane is a silicone resin of the general formula $R^*_sSiO_{(4-s)/2}$. Typically, a silicone resin will have T and/or Q units, along with M units and, optionally, D units. $R^*$ can be an independently selected substituted hydrocarbyl group, unsubstituted hydrocarbyl group, or hydroxyl group, and s is from 0 to 3. Suitable $R^*$ groups are as described above for $R^1$, $R^2$, and $R^{10}$. Various combinations of such groups can be present, provided the silicone resin has at least two hydroxyl groups per molecule (typically on M units). In these embodiments, the resin generally includes a combination of M, D, T, and/or Q units. In specific embodiments, the third siloxane is a MDT resin, a MT resin, a MDQ resin, a MQ resin, or a MDTQ resin. Each of the M, D, and T units can have differing R groups. The silicone resin can be of various molecular weights, including, but not limited to, a number average molecular weight of from 800 to 500,000, or any number/range in between.

In certain embodiments, Elastomer 3 is according to the general formula (I):

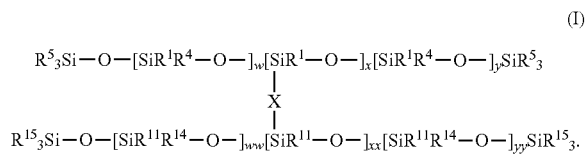

In formula (I), the upper and lower portions of Elastomer 3 are attributable to the first and second siloxanes. Each of $R^1$, $R^4$, $R^5$, $R^{11}$, $R^{14}$, and $R^{15}$, and subscripts w, x, y, ww, xx, and yy is as described above for Elastomer 1.

The middle (or "X") portion of formula (I) is attributable to the third siloxane, as well as the anhydride groups of the first and second siloxanes, and is according to the following general formula (J):

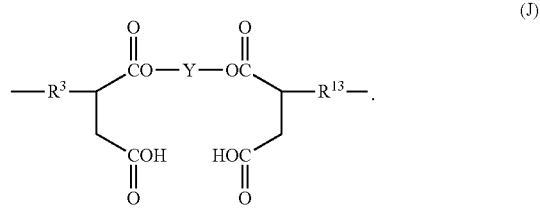

Each of $R^3$ and $R^{13}$ is as described above. Y is attributable to the third siloxane. During formation of Elastomer 3, the third siloxane had two hydroxyl groups, e.g. terminal hydroxyl groups, which reacted with pendant anhydride groups of the first and second siloxanes to form linkages between the siloxanes. As shown in formula (J), Elastomer 3 has at least two carboxyl groups. In other embodiments (not shown), another molecule of the third siloxane has reacted between the two carboxyl groups to form another —Y— linkage (i.e., the two carboxyl groups in formula (J) are gone).

Y can be of any structure attributable to the third siloxane. In various embodiments where the third siloxane is a polysiloxane, Y is of the following general formula (K):

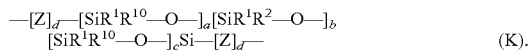

(K).

Each of $R^1$, $R^2$, $R^{10}$, and Z, and subscripts a, b, c, and d is as described above. In other embodiments where the third siloxane is a resin, Y is of the general formula $R^*_s SiO_{(4-s)/2}$. Each of $R^*$ and s is as described above.

In certain embodiments, Elastomer 3 can be formed with a supplemental cross-linker in addition to the third siloxane. Examples of suitable supplemental cross-linkers are as described above for Elastomer 1.

The first, second, and third siloxanes can be reacted in various amounts to form Elastomer 3. Based on the number of hydroxyl groups provided by the third siloxane, relative to the number of anhydride groups provided by the first and second siloxanes, the reactants can be utilized in a 1:1 stoichiometric ratio. Alternatively, the third siloxane can be utilized in a stoichiometric excess relative to the first and second siloxanes. Conversely, the first and second siloxanes can be utilized in a stoichiometric excess relative to the third siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 3 can include various functional groups, including free carboxyl groups, and possibly even free anhydride groups and/or free hydroxyl groups, or combinations thereof. In many embodiments, Elastomer 3 does not include free hydroxyl groups. In certain embodiments, Elastomer 3 has at least two carboxyl groups. Various degrees of cross-linking can be present in Elastomer 3 based on the index utilized to form Elastomer 3, from various degrees of partial cross-linking to full cross-linking.

Elastomer 4—Reaction Product of First and Second Siloxanes Having Pendant Anhydride Group(s) and Third Siloxane(s) Having Pendant and/or Terminal Amine Group(s)

In a fourth embodiment, the elastomer ("Elastomer 4") comprises the reaction product of a first siloxane, a second siloxane, and at least one third siloxane. In further embodiments, Elastomer 4 consists essentially of, optionally consists of, the reaction product of the first, second, and third siloxanes. In certain embodiments, Elastomer 4 can include the further reaction product of one or more siloxanes in addition to, and different from, the first, second, and third siloxanes. The first and second siloxanes are as described above for Elastomer 1. The third siloxane can be provided separate from the first and second siloxanes, such as in a "B-part" of a system for forming Elastomer 4.

The third siloxane of Elastomer 4 has at least two amine groups reactive with the pendant anhydride groups of the first and second siloxanes. Each of the amine groups can be pendant or terminal. In various embodiments, the third siloxane has two amine groups. In further embodiments, the third siloxane has two terminal amine groups and is free of pendant amine groups. Each of the amine groups can be directly bonded to a silicon atom, or to an intervening atom or linkage that is directly bonded to a silicon atom. Alternatively, each of the amine groups can be directly bonded to a carbon atom, or to an intervening atom or linkage that is directly bonded to a carbon atom. Each of the amine groups can be primary or secondary, optionally primary. The amine groups are useful for reaction with the first and second siloxanes, and can also impart additional functionality to Elastomer 4. In various embodiments, all of the amine groups of the third siloxane cross-link with anhydride groups of the first and second siloxanes to form linkages. Some amount of anhydride and/or carboxyl groups can remain free depending on the amount of amine groups present during reaction to form Elastomer 4.

The third siloxane of Elastomer 4 can be any type of siloxane provided it has at least two amine groups reactive with the pendant anhydride groups of the first and second siloxanes. In this way, the third siloxane serves as a cross-linker between the first and second siloxanes to form Elastomer 4. Elastomer 4 may constitute just one moiety provided by the third siloxane, or a plurality of moieties provided by the third siloxane depending on, for example, the number of pendant anhydride groups attributable to the first and second siloxanes.

In various embodiments, the third siloxane of Elastomer 4 comprises at least one D unit. In further embodiments, the third siloxane has repeating D units. In certain embodiments, the third siloxane of Elastomer 4 is a polysiloxane of the following general formula (L):

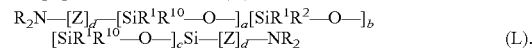

(L).

Each of R, $R^1$, $R^2$, $R^{10}$, and Z, and subscripts a, b, c, and d is as described above for Elastomer 3. In other embodiments, the third siloxane of Elastomer 4 is a silicone resin of the general formula $R^*_s SiO_{(4-s)/2}$. Each of $R^*$ and s is as described above.

In certain embodiments, Elastomer 4 is according to the general formula (M):

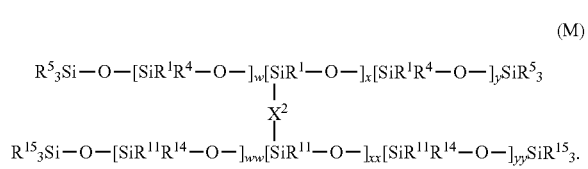

In formula (M), the upper and lower portions of Elastomer 4 are attributable to the first and second siloxanes. Each of $R^1$, $R^4$, $R^5$, $R^{11}$, $R^{14}$, and $R^{15}$, and subscripts w, x, y, ww, xx, and yy is as described above.

The middle (or "$X^2$") portion of formula (M) is attributable to the third siloxane, as well as the anhydride groups of the first and second siloxanes, and is according to the following general formula (N):

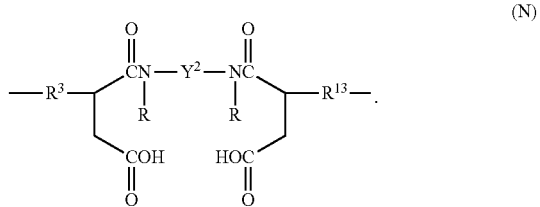

Each of R, $R^3$ and $R^{13}$ is as described above. Each $Y^2$ is a divalent group, which is attributable to the third siloxane. During formation of Elastomer 4, the third siloxane had two amine groups, e.g. terminal amine groups, which reacted with pendant anhydride groups of the first and second siloxanes to form linkages between the siloxanes. As shown in formula (N), Elastomer 4 has at least two carboxyl groups. In other embodiments (not shown), another molecule of the third siloxane has reacted between the two carboxyl groups to form another —$Y^2$— linkage (i.e., the two carboxyl groups in formula (N) are gone).

$Y^2$ can be of any structure attributable to the third siloxane of Elastomer 4. In various embodiments, $Y^2$ is of the following general formula (O):

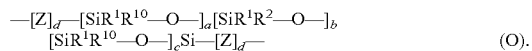

(O).

Each of $R^1$, $R^2$, $R^{10}$, and Z, and subscripts a, b, c, and d is as described above for Elastomer 3. In other embodiments where the third siloxane is a silicone resin, $Y^2$ is of the general formula $R*_sSiO_{(4-s)/2}$. Each of $R*$ and s is as described above.

In certain embodiments, Elastomer 4 can be formed with a supplemental cross-linker in addition to the third siloxane. Examples of suitable supplemental cross-linkers are as described above for Elastomer 1.

The first, second, and third siloxanes can be reacted in various amounts to form Elastomer 4. Based on the number of amine groups provided by the third siloxane, relative to the number of anhydride groups provided by the first and second siloxanes, the reactants can be utilized in a 1:1 stoichiometric ratio. Alternatively, the third siloxane can be utilized in a stoichiometric excess relative to the first and second siloxanes. Conversely, the first and second siloxanes can be utilized in a stoichiometric excess relative to the third siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 4 can include various functional groups, including free carboxyl groups, and possibly even free anhydride groups and/or free amine groups, or combinations thereof. In many embodiments, Elastomer 4 does not include free amine groups. In certain embodiments, Elastomer 4 has at least two carboxyl groups. This disclosure is not limited to any particular subsequent reaction or use of such free functional groups. Various degrees of cross-linking can be present in Elastomer 4 based on the index utilized to form Elastomer 4, from various degrees of partial cross-linking to full cross-linking.

Elastomer 5—Reaction Product of First and Second Siloxanes Having Pendant Hydroxyl Group(s) and Third Siloxane(s) Having at Least Two Terminal Anhydride Groups In a fifth embodiment, the elastomer ("Elastomer 5") comprises the reaction product of a first siloxane, a second siloxane, and at least one third siloxane. In further embodiments, Elastomer 5 consists essentially of, optionally consists of, the reaction product of the first, second, and third siloxanes. In certain embodiments, Elastomer 5 can include the further reaction product of one or more siloxanes in addition to, and different from, the first, second, and third siloxanes.

Each of the first and second siloxanes has at least one, optionally at least two, hydroxyl group(s). Each of the hydroxyl groups can be pendant or terminal. In further embodiments, each of the first and second siloxanes has pendant hydroxyl groups and is free of terminal hydroxyl groups. Each of the hydroxyl groups can be directly bonded to a silicon atom, or to an intervening atom or linkage that is directly bonded to a silicon atom. Alternatively, each of the hydroxyl groups can be directly bonded to a carbon atom, or to an intervening atom or linkage that is directly bonded to a carbon atom. Each of the hydroxyl groups can be primary, secondary, or tertiary, optionally primary or secondary, optionally primary. The hydroxyl groups are useful for reaction with the third siloxane, and can also impart additional functionality to Elastomer 5. In various embodiments, all of the hydroxyl groups of the first and second siloxanes cross-link with anhydride groups of the third siloxane to form linkages (e.g. ester cross-links). Some amount of anhydride and/or carboxyl groups can remain free depending on the amount of hydroxyl groups present during reaction to form Elastomer 5.

The third siloxane of Elastomer 5 has at least two terminal anhydride groups. In certain embodiments, the third siloxane has two terminal anhydride groups and is free of pendant anhydride groups. In various embodiments, each of the anhydride groups is directly bonded to an intervening atom or linkage that is directly bonded to a silicon atom. The anhydride groups are useful for reaction with the first and second siloxanes, and can also impart additional functionality to Elastomer 5. In certain embodiments, the anhydride groups can provide free carboxyl groups, which can also provide benefits and/or be available for a subsequent, non-limiting reaction. In other embodiments, Elastomer 5 may have one or more free anhydride groups for a subsequent, non-limiting reaction.

Each of the first and second siloxanes can be chemically (or physically) the same, such as two separate molecules of the same siloxane component (or type), and can be provided together, such as in an "A-part" of a system for forming Elastomer 5, or can be provided separately, especially when they are different from each other. The third siloxane can be provided separate from the first and second siloxanes, such as in a "B-part" of a system for forming Elastomer 5.

In various embodiments, each of the first, second, and third siloxane comprises at least one D unit. In further embodiments, each of the first, second, and third siloxanes has repeating D units.

In various embodiments, the third siloxane of Elastomer 5 is of the following general formula (P):

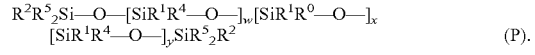

(P).

In further embodiments, the third siloxane is of the following general formula (Q):

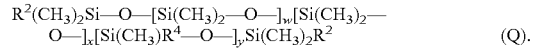

(Q).

Each of $R^1$, $R^2$, $R^4$, and $R^5$, and subscripts w, x, and y is as described above for Elastomer 1. Each $R^0$ can be $R^1$ or $R^2$. In certain embodiments, the third siloxane has two terminal anhydride groups (represented by $R^2$—as described above for Elastomer 1) and can have other side groups based on the presence of one or more D units associated with w, x, and/or y. In further embodiments, each $R^0$ is $R^1$. In certain embodiments, the third siloxane is a dimer, such that each of w, x, and y is 0.

Each of the first and second siloxanes can be any type of siloxane provided they have at least one hydroxyl group reactive with the terminal anhydride groups of the third siloxane. In this way, the third siloxane serves as a cross-linker between the first and second siloxanes to form Elastomer 5. Elastomer 5 may constitute just one moiety, or a plurality of moieties, imparted by the third siloxane depending on, for example, the number of hydroxyl groups attributable to the first and second siloxanes.

In certain embodiments, at least one, or both, of the first and second siloxanes is a polysiloxane individually of the following general formula (R):

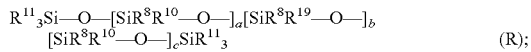

(R);

where each $R^{19}$ is of the following general formula (S):

$$-[Z]_d-OH \quad (S).$$

Each of $R^{10}$, $R^{11}$, and Z, and subscripts a, b, c, and d is as described above for Elastomer 3. $R^8$ can be an independently selected substituted or unsubstituted hydrocarbyl group. Examples of suitable groups for $R^8$ are $R^1$ and $R^4$ as described above for Elastomer 3. In alternate embodiments, $R^8$ may be silicone side chain of the siloxane.

In certain embodiments, at least one, or both, of the first and second siloxanes is a silicone resin of the general formula $R^*_s SiO_{(4-s)/2}$. Each of $R^*$ and s is as described above.

In certain embodiments, Elastomer 5 is of the following general formula (T):

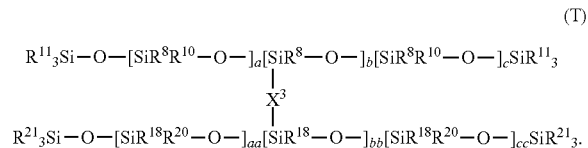

(T)

In formula (T), the upper and lower portions are attributable to the first and second siloxanes, which can be the same or different. Each of $R^8$, $R^{10}$, and $R^{11}$ is as described above. Each of subscripts a, b, and c are also as described above, and each of subscripts aa, bb, and cc can be the same as or different from each of a, b, and c, respectively. Each of $R^{18}$, $R^{20}$, and $R^{21}$ can be the same as or different from each of $R^8$, $R^{10}$, and $R^{11}$, respectively. Each $R^{11}$ may be $R^8$ and/or each $R^{21}$ may be $R^{18}$.

The middle (or "$X^3$") portion of formula (T) is attributable to the third siloxane, as well as the hydroxyl groups of the first and second siloxanes, and is according to the following general formula (U):

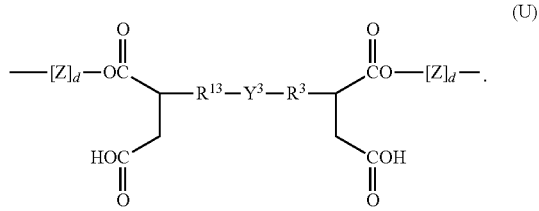

(U)

Each of Z, $R^3$, and $R^{13}$, and subscript d is as described above. Each $Y^3$ is a divalent group, such as an organic divalent group, which is attributable to the third siloxane. During formation of Elastomer 5, the first and second siloxanes had hydroxyl groups, e.g. pendant hydroxyl groups, which reacted with terminal anhydride groups of the third siloxane to form linkages between the siloxanes. As shown in formula (U), Elastomer 5 has at least two carboxyl groups. In other embodiments (not shown), two molecules of the first/second siloxane has reacted with the two carboxyl groups to form additional linkages (i.e., the two carboxyl groups in formula (U) are gone). In yet other embodiments (not shown), only one of the two carboxyl groups in formula (U) is gone, i.e., one carboxyl group remains free.

$Y^3$ can be of any structure attributable to the third siloxane. In various embodiments where the third siloxane is a polysiloxane, $Y^3$ is of the following general formula (V):

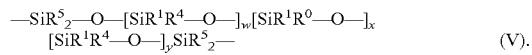

(V).

Each of $R^0$, $R^1$, $R^4$, and $R^5$, and subscripts w, x, and y is as described above. In other embodiments where the third siloxane is a resin, $Y^3$ is of the general formula $R^*_s SiO_{(4-s)/2}$. Each of $R^*$ and s is as described above.

In certain embodiments, Elastomer 5 can be formed with a supplemental cross-linker in addition to the third siloxane. Examples of suitable supplemental cross-linkers are as described above for Elastomer 1.

The first, second, and third siloxanes can be reacted in various amounts to form Elastomer 5. Based on the number of hydroxyl groups provided by the first and second siloxanes, relative to the number of anhydride groups provided by the third siloxane, the reactants can be utilized in a 1:1 stoichiometric ratio. Alternatively, the third siloxane can be utilized in a stoichiometric excess relative to the first and second siloxanes. Conversely, the first and second siloxanes can be utilized in a stoichiometric excess relative to the third siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 5 can include various functional groups, including free carboxyl groups, and possibly even free anhydride groups and/or free hydroxyl groups, or combinations thereof. In many embodiments, Elastomer 5 does not include free hydroxyl groups. In certain embodiments, Elastomer 5 has at least two carboxyl groups. Various degrees of cross-linking can be present in Elastomer 5 based on the index utilized to form Elastomer 5, from various degrees of partial cross-linking to full cross-linking.

Elastomer 6—Reaction Product of First and Second Siloxanes Having Pendant Amine Group(s) and Third Siloxane(s) Having at Least Two Terminal Anhydride Groups In a sixth embodiment, the elastomer ("Elastomer 6") comprises the reaction product of a first siloxane, a second siloxane, and at least one third siloxane. In further embodiments, Elastomer 6 consists essentially of, optionally consists of, the reaction product of the first, second, and third siloxanes. In certain embodiments, Elastomer 6 can include the further reaction product of one or more siloxanes in addition to, and different from, the first, second, and third siloxanes. The third siloxane is as described above for Elastomer 5.

Each of the first and second siloxanes has at least one, optionally at least two, amine group(s). Each of the amine groups can be pendant or terminal. In further embodiments, each of the first and second siloxanes has pendant amine groups and is free of terminal amine groups. Each of the amine groups can be directly bonded to a silicon atom, or to an intervening atom or linkage that is directly bonded to a silicon atom. Alternatively, each of the amine groups can be directly bonded to a carbon atom, or to an intervening atom or linkage that is directly bonded to a carbon atom. Each of the amine groups can be primary or secondary, optionally primary. The amine groups are useful for reaction with the third siloxane, and can also impart additional functionality to Elastomer 6. In various embodiments, all of the amine groups of the first and second siloxanes cross-link with anhydride groups of the third siloxane to form linkages. Some amount of anhydride and/or carboxyl groups can remain free depending on the amount of amine groups present during reaction to form Elastomer 6.

Each of the first and second siloxanes can be chemically (or physically) the same, such as two separate molecules of the same siloxane component (or type) and can be provided together, such as in an "A-part" of a system for forming Elastomer 6, or can be provided separately, especially when they are different from each other. The third siloxane can be provided separate from the first and second siloxanes, such as in a "B-part" of a system for forming Elastomer 6.

In various embodiments, each of the first, second, and third siloxane comprises at least one D unit. In further embodiments, each of the first, second, and third siloxanes has repeating D units.

Each of the first and second siloxanes can be any type of siloxane provided they have at least one amine group reactive with the terminal anhydride groups of the third siloxane. In this way, the third siloxane serves as a cross-linker between the first and second siloxanes to form Elastomer 6. Elastomer 6 may constitute just one moiety, or a plurality of moieties, imparted by the third siloxane depending on, for example, the number of amine groups attributable to the first and second siloxanes.

In certain embodiments, at least one, or both, of the first and second siloxanes is a polysiloxane individually of the following general formula (W):

$$R^{11}{}_3Si-O-[SiR^8R^{10}-O-]_a[SiR^8R^9-O-]_b[SiR^8R^{10}-O-]_cSiR^{11}{}_3 \quad (W);$$

where each $R^9$ is of the following general formula (X):

$$-[Z]_d-NR_2 \quad (X).$$

Each of R, $R^8$, $R^{10}$, and $R^{11}$, and subscripts a, b, c, and d is as described above. Each Z is a divalent group, and can be as described above. Examples of Z include structural units (or moieties) attributable to use of aminopropyl, aminoethylaminoisobutyl, and combinations thereof. In certain embodiments, Z can include one or more pendant functional (e.g. amine and/or hydroxyl) groups in addition to the terminal amine group attached thereto.

Z can also be attributable to a polyamine. Examples of suitable amines are as described above for Elastomer 2. Combinations of different polyamines can be utilized to impart Z.

In certain embodiments, at least one, or both, of the first and second siloxanes is a resin of the general formula $R^*{}_sSiO_{(4-s)/2}$. Each of R* and s is described above.

In certain embodiments, Elastomer 6 is of the following general formula (Y):

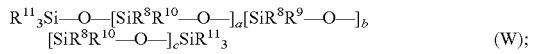

(Y)

In formula (Y), the upper and lower portions are attributable to the first and second siloxanes, which can be the same or different. Each of $R^8$, $R^{10}$, $R^{11}$, $R^{18}$, $R^{20}$, and $R^{21}$, and subscripts a, aa, b, bb, c, and cc is as described above.

The middle (or "$X^4$") portion of formula (Y) is attributable to the third siloxane, as well as the amine groups of the first and second siloxanes, and is according to the following general formula (Z):

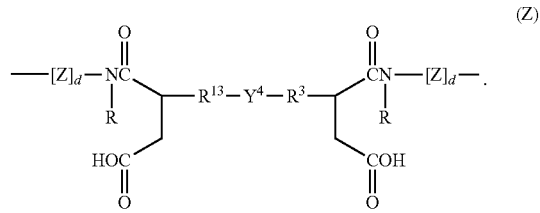

(Z)

Each of Z, R, $R^3$, and $R^{13}$, and subscript d is as described above. Each $Y^4$ is a divalent group, which is attributable to the third siloxane. During formation of Elastomer 6, the first and second siloxanes had amine groups, e.g. pendant amine groups, which reacted with terminal anhydride groups of the third siloxane to form linkages between the siloxanes. As shown in formula (Z), Elastomer 6 has at least two carboxyl groups. In other embodiments (not shown), two molecules of the first/second siloxane has reacted with the two carboxyl groups to form additional linkages (i.e., the two carboxyl groups in formula (Z) are gone). In yet other embodiments (not shown), only one of the two carboxyl groups in formula (Z) is gone, i.e., one carboxyl group remains free.

$Y^4$ can be of any structure attributable to the third siloxane. In various embodiments where the third siloxane is a polysiloxane, $Y^4$ is of the following general formula (AA):

(AA).

Each of $R^0$, $R^1$, $R^4$, and $R^5$, and subscripts w, x, and y is as described above. In other embodiments where the third siloxane is a resin, $Y^4$ is of the general formula: $R^*{}_sSiO_{(4-s)/2}$. Each of R* and s is as described above.

In certain embodiments, Elastomer 6 can be formed with a supplemental cross-linker in addition to the third siloxane. Examples of suitable supplemental cross-linkers are as described above for Elastomer 1.

The first, second, and third siloxanes can be reacted in various amounts to form Elastomer 6. Based on the number of amine groups provided by the first and second siloxanes, relative to the number of anhydride groups provided by the third siloxane, the reactants can be utilized in a 1:1 stoichiometric ratio. Alternatively, the third siloxane can be utilized in a stoichiometric excess relative to the first and second siloxanes. Conversely, the first and second siloxanes can be utilized in a stoichiometric excess relative to the third siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 6 can include various functional groups, including free carboxyl groups, and possibly even free anhydride groups and/or free amine groups, or combinations thereof. In many embodiments, Elastomer 6 does not include free amine groups. In certain embodiments, Elastomer 6 has at least two carboxyl groups. Various degrees of cross-linking can be present in Elastomer 6 based on the index utilized to form Elastomer 6, from various degrees of partial cross-linking to full cross-linking.

Elastomer 7—Reaction Product of First and Second Organic Alcohols and Siloxane(s) Having Terminal Anhydride Groups In a seventh embodiment, the elastomer ("Elastomer 7") comprises the reaction product of a first organic alcohol, a second organic alcohol, and at least one siloxane. In further embodiments, Elastomer 7 consists essentially of, optionally consists of, the reaction product of the first and second organic alcohols and the siloxane(s). In certain embodiments, Elastomer 7 can include the further reaction product of one or more alcohols in addition to, and different from, the first and second organic alcohols ("alcohols") and the siloxane(s). The siloxane is as described above as the third siloxane of Elastomer 5.

Each of the first and second organic alcohols has at least one, optionally at least two, hydroxyl group(s). In further embodiments, at least one, or each, of the alcohols has three or more hydroxyl groups. Each of the hydroxyl groups can be pendant or terminal. In certain embodiments, each of the alcohols has pendant hydroxyl group(s) and is free of terminal hydroxyl groups. Each of the hydroxyl groups can be directly bonded to a carbon atom, or to an intervening atom or linkage that is directly bonded to a carbon atom. Each of the hydroxyl groups can be primary, secondary, or tertiary, optionally primary or secondary, optionally primary. The hydroxyl groups are useful for reaction with the siloxane, and can also impart additional functionality to Elastomer 7. In various embodiments, all of the hydroxyl groups of the alcohols cross-link with anhydride groups of the siloxane to form linkages (e.g. ester cross-links). Some amount of anhydride and/or carboxyl groups can remain free depending on the amount of hydroxyl groups present during reaction to form Elastomer 7.

Each of the alcohols can be chemically (or physically) the same, such as two separate molecules of the same alcohol component (or type) and can be provided together, such as in an "A-part" of a system, or can be provided separately, especially when they are different from each other. The siloxane can be provided separate from the alcohols, such as in a "B-part" of a system for forming Elastomer 7.

Each of the alcohols can be any type of alcohol provided they have at least one hydroxyl group reactive with the terminal anhydride groups of the siloxane. In this way, the siloxane serves as a cross-linker between the alcohols to form Elastomer 7. Elastomer 7 may constitute just one moiety, or a plurality of moieties, imparted by the siloxane depending on, for example, the number of hydroxyl groups attributable to the alcohols. The alcohols may also serve as cross-linkers, end-cappers, and combinations thereof, depending on the number of hydroxyl groups provided by each. In certain embodiments, Elastomer 7 can include the further reaction product of one or more alcohols in addition to, and different from, the alcohols.

By "organic", it is generally meant that each of the alcohols contains predominantly carbon. While carbon is present, other atoms may also be present, such as oxygen atoms, hydrogen atoms, nitrogen atoms, etc. In many embodiments, each of the organic alcohols is free of silicon.

Each of the alcohols can independently be selected from the group consisting of organic monols having one hydroxyl group, polyols having two or more hydroxyl groups (e.g. diols, triols, tetrols, etc.), and combinations thereof. In various embodiments, at least one, or both, of the alcohols is a diol. Examples of suitable diols include those as described above for Elastomer 1. In other embodiments, at least one, or both, of the alcohols is a triol. Polyols of higher functionality may also be utilized.

In many embodiments, at least one, or both, of the alcohols has the following general formula: $HO-R^7-OH$; as described above for Elastomer 1. In certain embodiments, at least one, or both, of the alcohols is a (poly)oxyalkylene compound. Suitable examples of such compounds include those as described above for Elastomer 1.

In various embodiments, at least one, or both, of the alcohols can comprise a polyester polyol, a polyether polyol, a polyether/ester polyol, or combinations thereof. Furthermore, at least one, or both, of the alcohols may be selected from aliphatic polyols, cycloaliphatic polyols, aromatic polyols, heterocyclic polyols, and combinations thereof. Suitable examples of such compounds include those as described above for Elastomer 1. In specific embodiments, at least one, or both, of the alcohols is a polyether diol. Combinations of different alcohols can be utilized to form Elastomer 7.

In certain embodiments, Elastomer 7 is of the following general formula (BB):

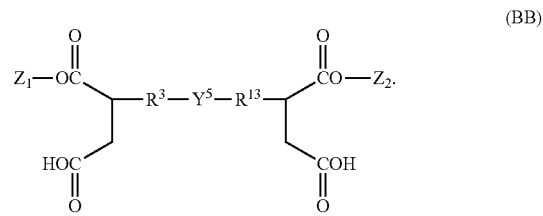

(BB)

In formula (BB), the leftmost and rightmost portions are attributable to the alcohols, which can be the same or different. Each of $R^3$ and $R^{13}$ is as described above. Each of $Z_1$ and $Z_2$ is independently attributable to one of the alcohols. The alcohols can be the same or different. In certain embodiments, one or both of $Z_1$ and $Z_2$ comprises at least one structural unit selected from the group consisting of: $[(CH_2)_i]_k$; $[(CH_2)_iO]_k$; $[(CH_2)_i(CH)(CH_3)O]_k$; $[(CH_2)_i(CH)(CH_2)_j(CH_3)O]_k$; $[(CH)OH]_k$; $[(CH)(CH_2)_iOH]_k$; $[(CH_3)_2COH(CH_2)_i]_k$; $[(CH_3)(CH_2)_iCOH(CH_2)_j(CH_3)]_k$; and combinations thereof. These units may be modified or rearranged to allow for proper orientation and bonding of the respective $Z_1$ and $Z_2$ units in formula (BB). Each of subscripts i, j, and k is as described above for Elastomer 3.

The middle (or "$Y^5$") portion of formula (BB) is attributable to the siloxane, as well as the hydroxyl groups of the alcohols. Each $Y^5$ is a divalent group, which is attributable to the siloxane. During formation of Elastomer 7, the alcohols had hydroxyl groups which reacted with terminal anhydride groups of the siloxane to form linkages between the siloxane and alcohols. As shown in formula (BB), Elastomer 7 has at least two carboxyl groups. In other embodiments (not shown), two molecules of the alcohols has reacted with the two carboxyl groups to form additional linkages (i.e., the two carboxyl groups in formula (BB) are gone). In yet other embodiments (not shown), only one of the two carboxyl groups in formula (BB) is gone, i.e., one carboxyl group remains free.

$Y^5$ can be of any structure attributable to the siloxane. In various embodiments where the siloxane is a polysiloxane, $Y^5$ is of the following general formula (CC):

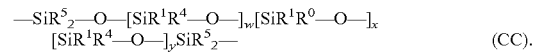

(CC).

Each of $R^0$, $R^1$, $R^4$, and $R^5$, and subscripts w, x, and y is as described above. In other embodiments where the siloxane is a resin, $Y^5$ is of the general formula: $R^*_s SiO_{(4-s)/2}$. Each of $R^*$ and s is as described above.

In certain embodiments, Elastomer 7 can be formed with a supplemental cross-linker in addition to the siloxane. Examples of suitable supplemental cross-linkers are as described above for Elastomer 1.

The alcohols and siloxane can be reacted in various amounts to form Elastomer 7. Based on the number of hydroxyl groups provided by the alcohols, relative to the number of anhydride groups provided by the siloxane, the reactants can be utilized in a 1:1 stoichiometric ratio. Alternatively, the siloxane can be utilized in a stoichiometric excess relative to the alcohols. Conversely, the alcohols can be utilized in a stoichiometric excess relative to the siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 7 can include various functional groups, including free carboxyl groups, and possibly even free anhydride groups and/or free hydroxyl groups, or combinations thereof. In many embodiments, Elastomer 7 does not include free hydroxyl groups. In certain embodiments, Elastomer 7 has at least two carboxyl groups. Various degrees of cross-linking can be present in Elastomer 7 based on the index utilized to form Elastomer 7, from various degrees of partial cross-linking to full cross-linking.

Elastomer 8—Reaction Product of First and Second Organic Amines and Siloxane(s) Having Terminal Anhydride Groups In an eighth embodiment, the elastomer ("Elastomer 8") comprises the reaction product of a first organic amine, a second organic amine, and at least one siloxane. In further embodiments, Elastomer 8 consists essentially of, optionally consists of, the reaction product of the first and second organic amines and the siloxane(s). In certain embodiments, Elastomer 8 can include the further reaction product of one or more amines in addition to, and different from, the first and second organic amines ("amines") and the siloxane(s). The siloxane is as described above as the third siloxane of Elastomer 5.

Each of the first and second organic amines has at least one, optionally at least two, amine group(s). In further embodiments, at least one, or each, of the amines has three or more amine groups. Each of the amine groups can be pendant or terminal. In certain embodiments, each of the amines has pendant amine group(s) and is free of terminal amine groups. Each of the amine groups can be directly bonded to a carbon atom, or to an intervening atom or linkage that is directly bonded to a carbon atom. Each of the amine groups can be primary or secondary, optionally primary. The amine groups are useful for reaction with the siloxane, and can also impart additional functionality to Elastomer 8. In various embodiments, all of the amine groups of the amines cross-link with anhydride groups of the siloxane to form linkages. Some amount of anhydride and/or carboxyl groups can remain free depending on the amount of amine groups present during reaction to form Elastomer 8.

Each of the amines can be chemically (or physically) the same, such as two separate molecules of the same amine component (or type) and can be provided together, such as in an "A-part" of a system for forming Elastomer 8 or can be provided separately, especially when they are separate from each other. The siloxane can be provided separate from the amines, such as in a "B-part" of a system for forming Elastomer 8.

Each of the amines can be any type of amine provided they have at least one amine group reactive with the terminal anhydride groups of the siloxane. In this way, the siloxane serves as a cross-linker between the amines to form Elastomer 8. Elastomer 8 may constitute just one moiety, or a plurality of moieties, imparted by the siloxane depending on, for example, the number of amine groups attributable to the amines. The amines may also serve as cross-linkers, endcappers, and combinations thereof, depending on the number of amine groups provided by each. In certain embodiments, Elastomer 8 can include the further reaction product of one or more amines in addition to, and different from, the amines.

By "organic", it is generally meant that each of the amines contains predominantly carbon. While carbon is present, other atoms may also be present, such as oxygen atoms, hydrogen atoms, nitrogen atoms, etc. In many embodiments, each of the organic amines is free of silicon.

Each of the amines can independently be selected from the group consisting of organic monoamines having one amine group, polyamines having two or more amine groups (e.g. diamines, triamines, tetramines, etc.), and combinations thereof. In various embodiments, at least one, or both, of the amines is a diamine. Examples of suitable diamines include those as described above for Elastomer 2. In other embodiments, at least one, or both, of the amines is a triamine. Polyamines of higher functionality may also be utilized.

In certain embodiments, at least one, or both, of the amines has the following general formula: $R_2N$—$R^{17}$—$NR_2$; as described above for Elastomer 2. In certain embodiments, at least one, or both, of the amines is a (poly) oxyalkylene compound. Suitable examples of such compounds include those as described above for Elastomer 2.

In various embodiments, at least one, or both, of the amines can comprise a polyester polyamine, a polyether polyamine, a polyether/ester polyamine, or combinations thereof. Furthermore, at least one, or both, of the amines may be selected from aliphatic polyamines, cycloaliphatic polyamines, aromatic polyamines, heterocyclic polyamines, and combinations thereof. Suitable examples of such compounds include those as described above for Elastomer 2. In specific embodiments, at least one, or both, of the amines is a polyether diamine. Combinations of different amines can be utilized to form Elastomer 8.

In certain embodiments, Elastomer 8 is of the following general formula (DD):

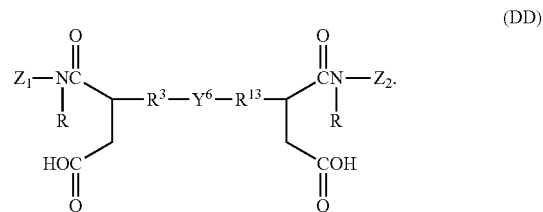

(DD)

In formula (DD), the leftmost and rightmost portions are attributable to the amines, which can be the same or different. Each of R, $R^3$, $R^{13}$, $Z_1$, and $Z_2$ is as described above.

The middle (or "$Y^6$") portion of formula (DD) is attributable to the siloxane, as well as the amine groups of the amines. Each $Y^6$ is a divalent group, which is attributable to the siloxane. During formation of Elastomer 8, the amines had amine groups which reacted with terminal anhydride groups of the siloxane to form linkages between the siloxane and amines. As shown in formula (DD), Elastomer 8 has at least two carboxyl groups. In other embodiments (not shown), two molecules of the amines has reacted with the two carboxyl groups to form additional linkages (i.e., the two carboxyl groups in formula (DD) are gone). In yet other embodiments (not shown), only one of the two carboxyl groups in formula (DD) is gone, i.e., one carboxyl group remains free.

$Y^6$ can be of any structure attributable to the siloxane. In various embodiments where the siloxane is a polysiloxane, $Y^6$ is of the following general formula (EE):

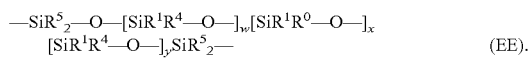

Each of $R^0$, $R^1$, $R^4$, and $R^5$, and subscripts w, x, and y is as described above. In other embodiments where the siloxane is a resin, $Y^6$ is of the general formula: $R^*_s SiO_{(4-s)/2}$. Each of $R^*$ and s is as described above.

In certain embodiments, Elastomer 8 can be formed with a supplemental cross-linker in addition to the siloxane. Examples of suitable supplemental cross-linkers are as described above for Elastomer 1.

The amines and siloxane can be reacted in various amounts to form Elastomer 8. Based on the number of amine groups provided by the amines, relative to the number of anhydride groups provided by the siloxane, the reactants can be utilized in a 1:1 stoichiometric ratio. Alternatively, the siloxane can be utilized in a stoichiometric excess relative to the amines. Conversely, the amines can be utilized in a stoichiometric excess relative to the siloxane. The index may be from 0.25 to 2.0, 0.5 to 1.5, 0.9 to 1.1, 0.95 to 1.05, or 1.0, or any number/range in between. Higher or lower indexes may also be utilized.

Based on the particular index utilized, various situations can arise. Specifically, Elastomer 8 can include various functional groups, including free carboxyl groups, and possibly even free anhydride groups and/or free amine groups, or combinations thereof. In many embodiments, Elastomer 8 does not include free amine groups. In certain embodiments, Elastomer 8 has at least two carboxyl groups. Various degrees of cross-linking can be present in Elastomer 8 based on the index utilized to form Elastomer 8, from various degrees of partial cross-linking to full cross-linking.

Additive

Various types of additives can be used along with the elastomer(s) to form the compositions of this disclosure. In general, the additive should be capable of stabilizing the elastomer. In particular, the additive generally serves to de-structure (e.g. thin), and/or improve the rheology for better mixing, while maintaining substantivity of the elastomer. The additive may also be referred to as a stabilizer, a de-structuring agent, or a rheology modifier. Without being bound or limited to any particular theory, it is thought that the additive blocks or prevents hydrogen bonding of the elastomer. Such hydrogen bonding is thought to cause structuring (e.g. thickening) of the elastomer.

Examples of additives that are thought to reduce structuring of the elastomer include hydroxyl (—OH) functional materials, such as alcohols (e.g. ethanol) and water; and Si-carboxy materials of various DPs, such as those of the general formula:

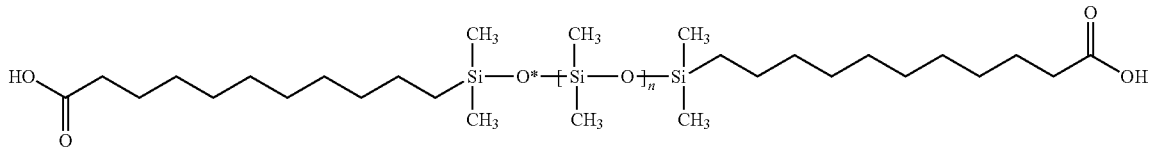

where n is 0 or an integer from 1 to 500, 5 to 250, or 10 to 250, or any integer/range in between.

In various embodiments, the additive is solid at room temperature (about 25° C.), optionally has a melting point greater than 25° C., optionally a melting point greater than 25° C. and generally a melting point less than a decomposition temperature of the elastomer and/or additive.

In certain embodiments, the additive comprises a silicon-based wax, an organic-based wax, or combinations thereof. Examples of silicon-based waxes include those of the formulas:

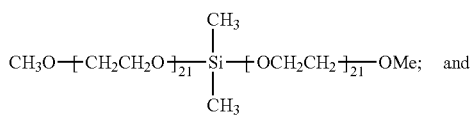

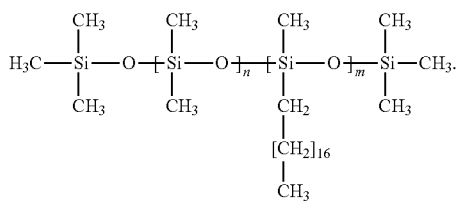

Examples of organic-based waxes include those of the general formulas:

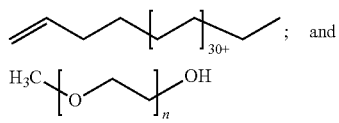

where n is an integer from 1 to 5000, 50 to 2500, 100 to 1000, or 1000, or any integer/range in between.

Further examples of additives that are thought to reduce structuring of the elastomer include dimethyl, methyl hydrogen siloxane trimethyl-term polymers with dimethylsiloxane dimethylvinyl-terminated; and a silixone of the formula:

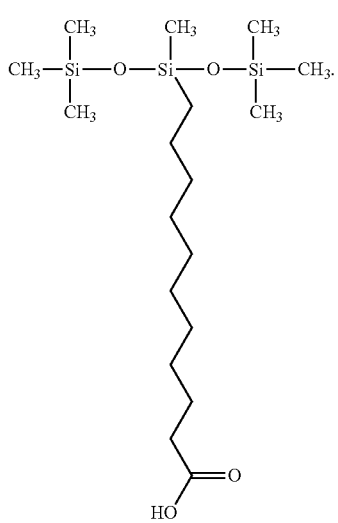 [SMILES: C[Si](C)(C)O[Si](C)(CCCCCCCCCCC(=O)O)O[Si](C)(C)C]

Yet further examples of additives that are thought to reduce structuring of the elastomer include copolymers, such as ethylene/propylene/styrene copolymers, butylene/ethylene/styrene copolymers, and combinations thereof.

In various embodiments, the additive comprises a siloxane-based polyamide. In these embodiments, the additive may also be referred to as a polysiloxane-based polyamide, a silicone polyamide, or simply as a polyamide. In certain embodiments, the additive comprises a siloxane-based polyamide having multiples of a unit represented by the following general Formula A:

Formula A

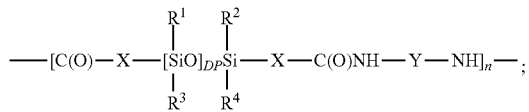

where:
(1) DP is generally selected from the group of 1-700, optionally 15-500, optionally 15-45. DP represents an average value for degree of polymerization of the siloxane units in the polymer with greater or lesser DP values centered around the indicated DP value.
(2) n is a number generally selected from the group of 1-500, optionally 1-100, optionally 4-25.
(3) X is a linear or branched chain alkylene generally having 1-30 carbons, optionally 3-10 carbons, optionally 10 carbons.
(4) Y is selected from linear or branched chain alkylenes generally having 1-40 carbons, optionally 1-20 carbons, optionally 2-6 carbons, optionally 6 carbons, where
   (a) The alkylene group may optionally and additionally contain in the alkylene portion at least one of (i) 1-3 amide linkages; (ii) C5 or C6 cycloalkane; and (iii) phenylene optionally substituted by 1-3 members selected independently from the group of C1-C3 alkyls; and
   (b) the alkylene group itself may optionally be substituted by at least one member selected from the group of (i) hydroxy; (ii) C3-C8 cycloalkane; (iii) 1-3 members selected independently from the group of C1-C3 alkyls; (iv) phenyl optionally substituted by 1-3 members selected independently from the group of C1-C3 alkyls; (v) C1-C3 alkyl hydroxy; and (vi) C1-C6 alkyl amines; or Y=Z where Z=T($R^{20}$)($R^{21}$)($R^{22}$) where each of $R^{20}$, $R^{21}$ and $R^{22}$ are independently selected from the group consisting of linear and branched C1-C10 alkylenes; and T is selected from the group consisting of CR, where R is selected from hydrogen, the group consisting of the group defined for $R^1$-$R^4$ (see (5) below) and a trivalent atom selected from N, P and Al.
(5) Each of $R^1$-$R^4$ (collectively "R") is independently selected from the group of methyl, ethyl, propyl, isopropyl, a siloxane chain, and phenyl, where the phenyl may optionally be substituted by 1-3 members from the group of methyl and ethyl. In further embodiments, each of $R^1$-$R^4$ may be selected from methyl and ethyl, optionally are methyl.
(6) Each of X, Y, DP, and $R^1$—$R^4$ may be the same or different for each polyamide unit.

Here, "siloxane chain" is generally meant a group of units, such as:

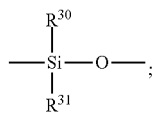

where $R^{30}$ and $R^{31}$ are each independently organic moieties; and each $R^{30}$ and $R^{31}$ are connected to silicon by a carbon-silicon bond.

In general, the carbon numbers in the alkylene chain do not include the carbons in the extra segments or substitutions. Also, the polyamides generally must have a siloxane portion in the backbone and optionally may have a siloxane portion in a pendant or branched portion.

If repeated with no variations in the defined variables, Formula A is representative of a linear homopolymer. Variations of this disclosure include: (1) polyamides in which multiple values of DP, and of units X, Y, and $R^1$-$R^4$ occur in one polymeric molecule, and where the sequencing of these units may be alternating, random, or block; (2) polyamides in which an organic triamine or higher amine (such as tris(2-aminoethyl)amine) replaces the organic diamine in part, to produce a branched or crosslinked molecule; and (3) physical blends of any of (1) and (2) and/or linear homopolymers.

Other components that may be suitable as the additive, including polyamides for example, and/or methods of forming such components, are described in U.S. RE38116, U.S. Pat. Nos. 5,981,680, 6,051,216, 6,353,076, 6,362,288, 6,451,295, 6,569,955, 7,410,695, 7,758,848, 7,790,148, 7,611,544, 7,601,179, 6,958,155, US 20030082129, US 20110306679, US 20100233114, US 20080171008, US 20070128233, US 20070041928, US 20060193801, US 20060104923, US 20050158260, US 2009010868, US 2012052030, US 2013253072, EP 1854451, JP 2008156242, FR 2967910, FR 2918273, FR 2918272, WO 2007054830, WO 2007054494, WO 2007054492, WO 2009086036, and WO 2012035513, the disclosures of which are incorporated by reference in their entirety. In certain embodiments, the additive comprises a polyether-polyamide, such as those described in U.S. Pat. No. 7,790,827, the disclosure of which is incorporated by reference.

The additive can be present in the composition in various amounts. In certain embodiments, the additive is present in an amount of from about 0.01 to about 100, about 1 to about 50, about 1 to about 40, about 1 to about 30, about 1 to about 25, about 1 to about 20, about 1 to about 15, about 1 to about 10, about 2 to about 10, about 2.5 to about 10, about 3 to about 10, about 3 to about 5, or about 5, parts by weight, based on 100 parts by weight of the elastomer.

As introduced above, carboxy-functionality of the elastomers is useful for improving substantivity of the elastomers on keratinous substrates. However, inter and intra-molecular interactions between polar moieties in the material structure of the elastomers, seemingly causes issues for material handling and formulation homogeneity in the form of structuring or thickening. To decrease structuring in carboxy-functional elastomers prior to use, mixing (shear thinning) can disrupt the interactions temporarily and allow for better introduction into a formulation. Introduction of polar solvents (e.g. water, EtOH, etc.) can also disrupt structuring; however, these materials limit formulation flexibility, especially in anhydrous formulations.

In general, silicone polyamides may be added to cosmetic compositions as thickeners or structuring agents. However, addition of silicone polyamides to the elastomers of this disclosure, e.g. direct addition, resulted in a surprising and an unexpected decrease in structuring while maintaining the performance (substantivity) of the elastomers.

Cosmetic Component

It is to be appreciated that certain components may be classified under different terms of art and just because a component is classified under such a term does not mean that they are limited to that function. As just one example, a component may be useful as a moisturizer but can also be useful for additional or alternate purposes, such as a diluent, an anti-aging active, an anti-bacterial agent, etc. The cosmetic component(s) may be present in the cosmetic composition in various amounts.

Cosmetic components are those components known to be used in cosmetic application. A wide review of such components may be found in the CTFA cosmetic component handbook. Exemplary cosmetic components are described in further detail below.

Cosmetic components include emollients, waxes, moisturizers, surface active materials such as surfactants or detergents or emulsifiers, thickeners, water phase stabilizing agents, pH controlling agents, preservatives and cosmetic biocides, sebum absorbants or sebum control agents, vegetable or botanical extracts, vitamins, proteins or aminoacids and their derivatives, pigments, colorants, fillers, silicone conditioning agents, cationic conditioning agents, hydrophobic conditioning agents, UV absorbers, sunscreen agents, antidandruff agents, antiperspirant agents, deodorant agents, skin protectants, hair dyes, nail care components, fragrances or perfume, antioxidants, oxidizing agents, reducing agents, propellant gases, and mixtures thereof.

Additional components that may be used in the cosmetic compositions include fatty alcohols, color care additives, anticellulites, pearlising agents, chelating agents, film formers, styling agents, ceramides, suspending agents, anti-aging actives, and others.

Health care components include antiacne agents, antibacterial agents, antifungal agents, therapeutic active agents, external analgesics, skin bleaching agents, anti-cancer agents, diuretics, agents for treating gastric and duodenal ulcers, proteolytic enzymes, antihistamine or H1 histamine blockers, sedatives, bronchodilators, diluents.

Additional components that may be used in the health care compositions include antibiotic, antiseptic, antibacterial, anti-inflammatory, astringents, hormones, smoking cessation compositions, cardiovascular, antiarrythmic, alpha-I blocker, beta blocker, ACE inhibitor, antiaggregant, non-steroidal anti-inflammatory agents such as diclofenac, anti-psoriasis agents such as clobetasol propionate, antidermatitis agents, tranquilizer, anticonvulsant, anticoagulant agents, healing factors, cell growth nutrients, peptides, corticosteroidal drugs, antipruritic agents and others.

Cosmetic components may be used in health care compositions, such as waxes, and others; and health care components may be used in cosmetic compositions such as anti-acne agents, and others.

Examples of emollients include volatile or non-volatile silicone oils; silicone resins such as polypropylsilsesquioxane and phenyl trimethicone; silicone elastomers such as dimethicone crosspolymer; alkylmethylsiloxanes such as $C_{30-45}$ alkyl methicone; volatile or non-volatile hydrocarbon compounds, such as squalene, paraffin oils, petrolatum oils and naphthalene oils; hydrogenated or partially hydrogenated polyisobutene; isoeicosane; isoparaffin; isododecane; isodecane or isohexa-decane; branched $C_8$-$C_{16}$ esters; isohexyl neopentanoate; ester oils such as isononyl isononanoate, cetostearyl octanoate, isopropyl myristate, palmitate derivatives, stearates derivatives, isostearyl isostearate and the heptanoates, octanoates, decanoates or ricinoleates of alcohols or of polyalcohols, or mixtures thereof; hydrocarbon oils of plant origin, such as wheatgerm, sunflower, grapeseed, castor, shea, avocado, olive, soybean, sweet almond, palm, rapeseed, cotton seed, hazelnut, macadamia, jojoba, blackcurrant, evening primrose; or triglycerides of caprylic/capric acids; higher fatty acids, such as oleic acid, linoleic acid or linolenic acid, and mixtures thereof.

Example of waxes include hydrocarbon waxes such as beeswax, lanolin wax, rice wax, carnauba wax, candelilla wax, microcrystalline waxes, paraffins, ozokerite, polyethylene waxes, synthetic wax, ceresin, lanolin, lanolin derivatives, cocoa butter, shellac wax, bran wax, capok wax, sugar cane wax, montan wax, whale wax, bayberry wax, silicone waxes (e.g. polymethylsiloxane alkyls, alkoxys and/or esters, $C_{30-45}$ alkyldimethylsilyl polypropylsilsesquioxane), and mixtures thereof Examples of moisturizers include lower molecular weight aliphatic diols such as propylene glycol and butylene glycol; polyols such as glycerine and sorbitol; and polyoxyethylene polymers such as polyethylene glycol 200; hyaluronic acid and its derivatives, and mixtures thereof.

Examples of surface active materials may be anionic, cationic or non ionic, and include organomodified silicones such as dimethicone copolyol; oxyethylenated and/or oxypropylenated ethers of glycerol; oxyethylenated and/or oxypropylenated ethers of fatty alcohols such as ceteareth-30, $C_{12-15}$ pareth-7; fatty acid esters of polyethylene glycol such as PEG-50 stearate, PEG-40 monostearate; saccharide esters and ethers, such as sucrose stearate, sucrose cocoate and sorbitan stearate, and mixtures thereof; phosphoric esters and salts thereof, such as DEA oleth-10 phosphate; sulphosuccinates such as disodium PEG-5 citrate lauryl sulphosuccinate and disodium ricinoleamido MEA sulphosuccinate; alkyl ether sulphates, such as sodium lauryl ether sulphate; isethionates; betaine derivatives; and mixtures thereof.

Further examples of nonionic surfactants include polyoxyethylene alkyl ethers, polyoxyethylene alkylphenol ethers, polyoxyethylene lauryl ethers, polyoxyethylene sorbitan monoleates, polyoxyethylene alkyl esters, polyoxyethylene sorbitan alkyl esters, polyethylene glycol, polypropylene glycol, diethylene glycol, ethoxylated trimethylnonanols, polyoxyalkylene-substituted silicones (rake or ABn types), silicone alkanolamides, silicone esters, silicone glycosides, and mixtures thereof.

Nonionic surfactants include dimethicone copolyols, fatty acid esters of polyols, for instance sorbitol or glyceryl mono-, di-, tri- or sesqui-oleates or stearates, glyceryl or polyethylene glycol laurates; fatty acid esters of polyethylene glycol (polyethylene glycol monostearate or monolaurate); polyoxyethylenated fatty acid esters (stearate or oleate) of sorbitol; polyoxyethylenated alkyl (lauryl, cetyl, stearyl or octyl)ethers.

Anionic surfactants include carboxylates (sodium 2-(2-hydroxyalkyloxy)acetate)), amino acid derivatives (N-acylglutamates, N-acylgly-cinates or acylsarcosinates), alkyl sulfates, alkyl ether sulfates and oxyethylenated derivatives thereof, sulfonates, isethionates and N-acylisethionates, taurates and N-acyl N-methyltaurates, sulfosuccinates, alkylsulfoacetates, phosphates and alkyl phosphates, polypeptides, anionic derivatives of alkyl polyglycoside (acyl-D-galactoside uronate), and fatty acid soaps, and mixtures thereof.

Amphoteric and zwitterionic surfactants include betaines, N-alkylamidobetaines and derivatives thereof, proteins and derivatives thereof, glycine derivatives, sultaines, alkyl polyaminocarboxylates and alkylamphoacetates, and mixtures thereof.

Examples of thickeners include acrylamide copolymers, acrylate copolymers and salts thereof (such as sodium polyacrylate), xanthan gum and derivatives, cellulose gum and cellulose derivatives (such as methylcellulose, methylhydroxypropylcellulose, hydroxypropylcellulose, polypropylhydroxyethylcellulose), starch and starch derivatives (such as hydroxyethylamylose and starch amylase), polyoxyethylene, carbomer, sodium alginate, arabic gum, cassia gum, guar gum and guar gum derivatives, cocamide derivatives, alkyl alcohols, gelatin, PEG-derivatives, saccharides (such as fructose, glucose) and saccharides derivatives (such as PEG-120 methyl glucose diolate), and mixtures thereof.

Examples of water phase stabilizing agents include electrolytes (e.g. alkali metal salts and alkaline earth salts, especially the chloride, borate, citrate, and sulfate salts of sodium, potassium, calcium and magnesium, as well as aluminum chlorohydrate, and polyelectrolytes, especially hyaluronic acid and sodium hyaluronate), polyols (glycerine, propylene glycol, butylene glycol, and sorbitol), alcohols such as ethyl alcohol, and hydrocolloids, and mixtures thereof.

Examples of pH controlling agents include any water soluble acid such as a carboxylic acid or a mineral acid such as hydrochloric acid, sulphuric acid, and phosphoric acid, monocarboxylic acid such as acetic acid and lactic acid, and polycarboxylic acids such as succinic acid, adipic acid, citric acid, and mixtures thereof.

Example of preservatives and cosmetic biocides include paraben derivatives, hydantoin derivatives, chlorhexidine and its derivatives, imidazolidinyl urea, phenoxyethanol, silver derivatives, salicylate derivatives, triclosan, ciclopirox olamine, hexamidine, oxyquinoline and its derivatives, PVP-iodine, zinc salts and derivatives such as zinc pyrithione, and mixtures thereof.

Examples of sebum absorbants or sebum control agents include silica silylate, silica dimethyl silylate, dimethicone/vinyl dimethicone crosspolymer, polymethyl methacrylate, cross-linked methylmethacrylate, aluminum starch octenylsuccinate, and mixtures thereof.

Examples of vegetable or botanical extracts are derived from plants (herbs, roots, flowers, fruits, or seeds) in oil or water soluble form, such as coconut, green tea, white tea, black tea, horsetail, Ginkgo biloba, sunflower, wheat germ, seaweed, olive, grape, pomegranate, aloe, apricot kernel, apricot, carrot, tomato, tobacco, bean, potato, actzuki bean, catechu, orange, cucumber, avocado, watermelon, banana, lemon or palm. Examples of herbal extracts include dill, horseradish, oats, neem, beet, broccoli, tea, pumpkin, soybean, barley, walnut, flax, ginseng, poppy, avocado, pea, sesame, and mixtures thereof.

Examples of vitamins include a variety of different organic compounds such as alcohols, acids, sterols, and quinones. They may be classified into two solubility groups: lipid-soluble vitamins and water-soluble vitamins. Lipid-soluble vitamins that have utility in personal care formulations include retinol (vitamin A), ergocalciferol (vitamin D2), cholecalciferol (vitamin D3), phytonadione (vitamin K1), and tocopherol (vitamin E). Water-soluble vitamins that have utility in personal care formulations include ascorbic acid (vitamin C), thiamin (vitamin B1) niacin (nicotinic acid), niacinamide (vitamin B3), riboflavin (vitamin B2), pantothenic acid (vitamin B5), biotin, folic acid, pyridoxine (vitamin B6), and cyanocobalamin (vitamin B12). Additional examples of vitamins include derivatives of vitamins such as retinyl palmitate (vitamin A palmitate), retinyl acetate (vitamin A acetate), retinyl linoleate (vitamin A linoleate), and retinyl propionate (vitamin A propionate), tocopheryl acetate (vitamin E acetate), tocopheryl linoleate (vitamin E linoleate), tocopheryl succinate (vitamin E succinate), tocophereth-5, tocophereth-10, tocophereth-12, tocophereth-18, tocophereth-50 (ethoxylated vitamin E derivatives), PPG-2 tocophereth-5, PPG-5 tocophereth-2, PPG-10 tocophereth-30, PPG-20 tocophereth-50, PPG-30 tocophereth-70, PPG-70 tocophereth-100 (propoxylated and ethoxylated vitamin E derivatives), sodium tocopheryl phosphate, ascorbyl palmitate, ascorbyl dipalmitate, ascorbyl glucoside, ascorbyl tetraisopalmitate, tetrahexadecyl ascorbate, ascorbyl tocopheryl maleate, potassium ascorbyl tocopheryl phosphate, tocopheryl nicotinate, and mixtures thereof.

Examples of proteins or amino-acids and their derivatives include those extracted from wheat, soy, rice, corn, keratin, elastin or silk. Proteins may be in the hydrolyzed form and they may also be quaternized, such as hydrolyzed elastin, hydrolyzed wheat powder, hydrolyzed silk. Examples of protein include enzymes such as hydrolases, cutinases, oxidases, transferases, reductases, hemicellulases, esterases, isomerases, pectinases, lactases, peroxidases, laccases, catalases, and mixtures thereof. Examples of hydrolases include proteases (bacterial, fungal, acid, neutral or alkaline), amylases (alpha or beta), lipases, mannanases, cellulases, collagenases, lisozymes, superoxide dismutase, catalase, and mixtures thereof.

Examples of pigments and colorants include surface treated or untreated iron oxides, surface treated or untreated titanium dioxide, surface treated or untreated mica, silver oxide, silicates, chromium oxides, carotenoids, carbon black, ultramarines, chlorophyllin derivatives and yellow ocher. Examples of organic pigments include aromatic types including azo, indigoid, triphenylmethane, anthraquinone, and xanthine dyes which are designated as D&C and FD&C blues, browns, greens, oranges, reds, yellows, etc., and mixtures thereof. Surface treatments include those treatments based on lecithin, silicone, silanes, fluoro compounds, and mixtures thereof.

Examples of fillers include talc, micas, kaolin, zinc or titanium oxides, calcium or magnesium carbonates, silica, silica silylate, titanium dioxide, glass or ceramic beads, polymethylmethacrylate beads, boron nitride, aluminum silicate, aluminum starch octenylsuccinate, bentonite, magnesium aluminum silicate, nylon, silk powder metal soaps derived from carboxylic acids having 8-22 carbon atoms, non-expanded synthetic polymer powders, expanded powders and powders from natural organic compounds, such as cereal starches, which may or may not be crosslinked, copolymer microspheres, polytrap, silicone resin microbeads, and mixtures thereof. The fillers may be surface treated to modify affinity or compatibility with remaining components.

Examples of silicone conditioning agents include silicone oils such as dimethicone; silicone gums such as dimethiconol; silicone resins such as trimethylsiloxy silicate, polypropyl silsesquioxane; silicone elastomers; alkylmethylsiloxanes; organomodified silicone oils, such as amodimethicone, aminopropyl phenyl trimethicone, phenyl trimethicone, trimethyl pentaphenyl trisiloxane, silicone quaternium-16/glycidoxy dimethicone crosspolymer, silicone quaternium-16; saccharide functional siloxanes; carbinol functional siloxanes; silicone polyethers; siloxane copolymers (divinyldimethicone/dimethicone copolymer); acrylate or acrylic functional siloxanes; and mixtures or emulsions thereof.

Examples of cationic conditioning agents include guar derivatives such as hydroxypropyltrimethylammonium derivative of guar gum; cationic cellulose derivatives, cationic starch derivatives; quaternary nitrogen derivatives of cellulose ethers; homopolymers of dimethyldiallyl ammonium chloride; copolymers of acrylamide and dimethyldiallyl ammonium chloride; homopolymers or copolymers derived from acrylic acid or methacrylic acid which contain cationic nitrogen functional groups attached to the polymer by ester or amide linkages; polymeric quaternary ammonium salts of hydroxyethyl cellulose reacted with a fatty alkyl dimethyl ammonium substituted epoxide; polycondensation products of N,N'-bis-(2,3-epoxypropyl)-piperazine or piperazine-bis-acrylamide and piperazine; and copolymers of vinylpyrrolidone and acrylic acid esters with quaternary nitrogen functionality. Specific materials include the various polyquats Polyquaternium-7, Polyquaternium-8, Polyquaternium-10, Polyquaternium-11, and Polyquaternium-23. Other categories of conditioners include cationic surfactants such as cetyl trimethylammonium chloride, cetyl trimethylammonium bromide, stearyltrimethylammonium chloride, and mixtures thereof. In some instances, the cationic conditioning agent is also hydrophobically modified, such as hydrophobically modified quaternized hydroxyethylcellulose polymers; cationic hydrophobically modified galactomannan ether; and mixtures thereof.

Examples of hydrophobic conditioning agents include guar derivatives; galactomannan gum derivatives; cellulose derivatives; and mixtures thereof.

UV absorbers and sunscreen agents include those which absorb ultraviolet light between about 290-320 nanometers (the UV-B region) and those which absorb ultraviolet light in the range of 320-400 nanometers (the UV-A region).

Some examples of sunscreen agents are aminobenzoic acid, cinoxate, diethanolamine methoxycinnamate, digalloyl trioleate, dioxybenzone, ethyl 4-[bis(Hydroxypropyl)] aminobenzoate, glyceryl aminobenzoate, homosalate, lawsone with dihydroxyacetone, menthyl anthranilate, octocrylene, ethyl hexyl methoxycinnamate, octyl salicylate, oxybenzone, padimate 0, phenylbenzimidazole sulfonic acid, red petrolatum, sulisobenzone, titanium dioxide, trolamine salicylate, and mixtures thereof.

Some examples of UV absorbers are acetaminosalol, allatoin PABA, benzalphthalide, benzophenone, benzophenone 1-12, 3-benzylidene camphor, benzylidenecamphor hydrolyzed collagen sulfonamide, benzylidene camphor sulfonic Acid, benzyl salicylate, bornelone, bumetriozole, butyl methoxydibenzoylmethane, butyl PABA, ceria/silica, ceria/silica talc, cinoxate, DEA-methoxycinnamate, dibenzoxazol naphthalene, di-t-butyl hydroxybenzylidene camphor, digalloyl trioleate, diisopropyl methyl cinnamate, dimethyl PABA ethyl cetearyldimonium tosylate, dioctyl butamido triazone, diphenyl carbomethoxy acetoxy naphthopyran, disodium bisethylphenyl tiamminotriazine stilbenedisulfonate, disodium distyrylbiphenyl triaminotriazine stilbenedisulfonate, disodium distyrylbiphenyl disulfonate, drometrizole, drometrizole trisiloxane, ethyl dihydroxypropyl PABA, ethyl diisopropylcinnamate, ethyl methoxycinnamate, ethyl PABA, ethyl urocanate, etrocrylene ferulic acid, glyceryl octanoate dimethoxycinnamate, glyceryl PABA, glycol salicylate, homosalate, isoamyl p-methoxycinnamate, isopropylbenzyl salicylate, isopropyl dibenzolylmethane, isopropyl methoxycinnamate, menthyl anthranilate, menthyl salicylate, 4-methylbenzylidene, camphor, octocrylene, octrizole, octyl dimethyl PABA, ethyl hexyl methoxycinnamate, octyl salicylate, octyl triazone, PABA, PEG-25 PABA, pentyl dimethyl PABA, phenylbenzimidazole sulfonic acid, polyacrylamidomethyl benzylidene camphor, potassium methoxycinnamate, potassium phenylbenzimidazole sulfonate, red petrolatum, sodium phenylbenzimidazole sulfonate, sodium urocanate, TEA-phenylbenzimidazole sulfonate, TEA-salicylate, terephthalylidene dicamphor sulfonic acid, titanium dioxide, tri-PABA panthenol, urocanic acid, VA/crotonates/methacryloxybenzophenone-1 copolymer, and mixtures thereof.

Examples of antidandruff agents include pyridinethione salts, selenium compounds such as selenium disulfide, and soluble antidandruff agents, and mixtures thereof.

Examples of antiperspirant agents and deodorant agents include aluminum chloride, aluminum zirconium tetrachlorohydrex GLY, aluminum zirconium tetrachlorohydrex PEG, aluminum chlorohydrex, aluminum zirconium tetrachlorohydrex PG, aluminum chlorohydrex PEG, aluminum zirconium trichlorohydrate, aluminum chlorohydrex PG, aluminum zirconium trichlorohydrex GLY, hexachlorophene, benzalkonium chloride, aluminum sesquichlorohydrate, sodium bicarbonate, aluminum sesquichlorohydrex PEG, chlorophyllin-copper complex, triclosan, aluminum zirconium octachlorohydrate, zinc ricinoleate, and mixtures thereof.

Examples of skin protectants include allantoin, aluminium acetate, aluminium hydroxide, aluminium sulfate, calamine, cocoa butter, cod liver oil, colloidal oatmeal, dimethicone, glycerin, kaolin, lanolin, mineral oil, petrolatum, shark liver oil, sodium bicarbonate, talc, witch hazel, zinc acetate, zinc carbonate, zinc oxide, and mixtures thereof.

Examples of hair dyes include 1-acetoxy-2-methylnaphthalene; acid dyes; 5-amino-4-chloro-o-cresol; 5-amino-2,6-dimethoxy-3-hydroxypyridine; 3-amino-2,6-dimethylphenol; 2-amino-5-ethylphenol HCl; 5-amino-4-fluoro-2-methylphenol sulfate; 2-amino-4-hydroxyethylaminoanisole; 2-amino-4-hydroxyethylaminoanisole sulfate; 2-amino-5-nitrophenol; 4-amino-2-nitrophenol; 4-amino-3-nitrophenol; 2-amino-4-nitrophenol sulfate; m-aminophenol HCl; p-aminophenol HCl; m-aminophenol; o-aminophenol; 4,6-bis(2-hydroxyethoxy)-m-phenylenediamine HCl; 2,6-bis(2-hydroxyethoxy)-3,5-pyridinediamine HCl; 2-chloro-6-ethylamino-4-nitrophenol; 2-chloro-5-nitro-N-hydroxyethyl p-phenylenediamine; 2-chloro-p-phenylenediamine; 3,4-di-aminobenzoic acid; 4,5-diamino-1-((4-chlorophenyl)methyl)-1 H-pyrazole-sulfate; 2,3-diaminodihydropyrazolo pyrazolone dimethosulfonate; 2,6-diaminopyridine; 2,6-diamino-3-((pyridin-3-yl)azo)pyridine; dihydroxyindole; dihydroxyindoline; N,N-dimethyl-p-phenylenediamine; 2,6-dimethyl-p-phenylenediamine; N,N-dimethyl-p-phenylenediamine sulfate; direct dyes; 4-ethoxy-m-phenylenediamine sulfate; 3-ethylamino-p-cresol sulfate; N-ethyl-3-nitro PABA; gluconamidopropyl aminopropyl dimethicone; *Haematoxylon brasiletto* wood extract; HC dyes; *Lawsonia inermis* (Henna) extract; hydroxyethyl-3,4-methylenedioxyaniline HCl; hydroxyethyl-2-nitro-p-toluidine; hydroxyethyl-p-phenylenediamine sulfate; 2-hydroxyethyl picramic acid; hydroxypyridinone; hydroxysuccinimidyl $C_{21}$-$C_{22}$ isoalkyl acidate; isatin; *Isatis tinctoria* leaf powder; 2-methoxymethyl-p-phenylenediamine sulfate; 2-methoxy-p-phenylenediamine sulfate; 6-methoxy-2,3-pyridinediamine HCl; 4-methylbenzyl 4,5-diamino pyrazole sulfate; 2,2'-methylenebis 4-aminophenol; 2,2'-methylenebis-4-aminophenol HCl; 3,4-methylenedioxyaniline; 2-methylresorcinol; methylrosanilinium chloride; 1,5-naphthalenediol; 1,7-naphthalenediol; 3-nitro-p-Cresol; 2-nitro-5-glyceryl methylaniline; 4-nitroguaiacol; 3-nitro-p-hydroxyethylaminophenol; 2-nitro-N-hydroxyethyl-p-anisidine; nitrophenol; 4-nitrophenyl aminoethylurea; 4-nitro-o-phenylenediamine dihydrochloride; 2-nitro-p-phenylenediamine dihydrochloride; 4-nitro-o-phenylenediamine HCl; 4-nitro-m-phenylenediamine; 4-nitro-o-phenylenediamine; 2-nitro-p-phenylenediamine; 4-nitro-m-phenylenediamine sulfate; 4-nitro-o-phenylenediamine sulfate; 2-nitro-p-phenylenediamine sulfate; 6-nitro-2,5-pyridinediamine; 6-nitro-o-toluidine; PEG-3 2,2'-di-p-phenylenediamine; p-phenylenediamine HCl; p-phenylenediamine sulfate; phenyl methyl pyrazolone; N-phenyl-p-phenylenediamine HCl; pigment blue 15:1; pigment violet 23; pigment yellow 13; pyrocatechol; pyrogallol; resorcinol; sodium picramate; sodium sulfanilate; solvent yellow 85; solvent yellow 172; tetraaminopyrimidine sulfate; tetrabromophenol blue; 2,5,6-triamino-4-pyrimidinol sulfate; 1,2,4-trihydroxybenzene.

Example of nail care components include butyl acetate; ethyl acetate; nitrocellulose; acetyl tributyl citrate; isopropyl alcohol; adipic acid/neopentyl glycol/trimelitic anhydride copolymer; stearalkonium bentonite; acrylates copolymer; calcium pantothenate; gCetraria *islandica* extract; *Chondrus crispus*; styrene/acrylates copolymer; trimethylpentanediyl dibenzoate-1; polyvinyl butyral; N-butyl alcohol; propylene glycol; butylene glycol; mica; silica; tin oxide; calcium borosilicate; synthetic fluorphlogopite; polyethylene terephtalate; sorbitan laurate derivatives; talc; jojoba extract; diamond powder; isobutylphenoxy epoxy resin; silk powder; and mixtures thereof.

Examples of fragrances or perfume include hexyl cinnamic aldehyde; anisaldehyde; methyl-2-n-hexyl-3-oxo-cyclopentane carboxylate; dodecalactone gamma; methylphenylcarbinyl acetate; 4-acetyl-6-tert-butyl-1,1-dimethyl indane; patchouli; olibanum resinoid; labdanum; vetivert; copaiba balsam; fir balsam; 4-(4-hydroxy-4-methyl pentyl)-3-cyclohexene-1-carboxaldehyde; methyl anthranilate; geraniol; geranyl acetate; linalool; citronellol; terpinyl acetate; benzyl salicylate; 2-methyl-3-(p-isopropylphenyl)-propanal; phenoxyethyl isobutyrate; cedryl acetal; aubepine; musk fragrances; macrocyclic ketones; macrolactone musk fragrances; ethylene brassylate; and mixtures thereof. Further perfume components are described in detail in standard textbook references such as Perfume and Flavour Chemicals, 1969, S. Arctander, Montclair, N.J.

Examples of antioxidants are acetyl cysteine, arbutin, ascorbic acid, ascorbic acid polypeptide, ascorbyl dipalmitate, ascorbyl methylsilanol pectinate, ascorbyl palmitate, ascorbyl stearate, BHA, p-hydroxyanisole, BHT, t-butyl hydroquinone, caffeic acid, *Camellia sinensis* oil, chitosan ascorbate, chitosan glycolate, chitosan salicylate, chlorogenic acids, cysteine, cysteine HCl, decyl mercaptomethylimidazole, erythorbic acid, diamylhydroquinone, di-t-butylhydroquinone, dicetyl thiodipropionate, dicyclopentadiene/t-butylcresol copolymer, digalloyl trioleate, dilauryl thiodipropionate, dimyristyl thiodipropionate, dioleyl tocopheryl methylsilanol, isoquercitrin, diosmine, disodium ascorbyl sulfate, disodium rutinyl disulfate, distearyl thiodipropionate, ditridecyl thiodipropionate, dodecyl gallate, ethyl ferulate, ferulic acid, hydroquinone, hydroxylamine HCl, hydroxylamine sulfate, isooctyl thioglycolate, kojic acid, madecassicoside, magnesium ascorbate, magnesium ascorbyl phosphate, melatonin, methoxy-PEG-7 rutinyl succinate, methylene di-t-butylcresol, methylsilanol ascorbate, nordihydroguaiaretic acid, octyl gallate, phenylthioglycolic acid, phloroglucinol, potassium ascorbyl tocopheryl phosphate, thiodiglycolamide, potassium sulfite, propyl gallate, rosmarinic acid, rutin, sodium ascorbate, sodium ascorbyl/cholesteryl phosphate, sodium bisulfite, sodium erythorbate, sodium metabisulfide, sodium sulfite, sodium thioglycolate, sorbityl furfural, tea tree (*Melaleuca aftemifolia*) oil, tocopheryl acetate, tetrahexyldecyl ascorbate, tetrahydrodiferuloylmethane, tocopheryl linoleate/oleate, thiodiglycol, tocopheryl succinate, thiodiglycolic acid, thioglycolic acid, thiolactic acid, thiosalicylic acid, thiotaurine, retinol, tocophereth-5, tocophereth-10, tocophereth-12, tocophereth-18, tocophereth-50, tocopherol, tocophersolan, tocopheryl linoleate, tocopheryl nicotinate, tocoquinone, o-tolyl biguanide, tris(nonylphenyl) phosphite, ubiquinone, zinc dibutyldithiocarbamate, and mixtures thereof.

Examples of oxidizing agents are ammonium persulfate, calcium peroxide, hydrogen peroxide, magnesium peroxide, melamine peroxide, potassium bromate, potassium caroate, potassium chlorate, potassium persulfate, sodium bromate, sodium carbonate peroxide, sodium chlorate, sodium iodate, sodium perborate, sodium persulfate, strontium dioxide, strontium peroxide, urea peroxide, zinc peroxide, and mixtures thereof.

Examples of reducing agents are ammonium bisulfite, ammonium sulfite, ammonium thioglycolate, ammonium thiolactate, cystemaine HCl, cystein, cysteine HCl, ethanolamine thioglycolate, glutathione, glyceryl thioglycolate, glyceryl thioproprionate, hydroquinone, p-hydroxyanisole, isooctyl thioglycolate, magnesium thioglycolate, mercaptopropionic acid, potassium metabisulfite, potassium sulfite, potassium thioglycolate, sodium bisulfite, sodium hydrosulfite, sodium hydroxymethane sulfonate, sodium metabisulfite, sodium sulfite, sodium thioglycolate, strontium thioglycolate, superoxide dismutase, thioglycerin, thioglycolic acid, thiolactic acid, thiosalicylic acid, zinc formaldehyde sulfoxylate, and mixtures thereof.

Examples of propellant gases include carbon dioxide, nitrogen, nitrous oxide, volatile hydrocarbons such as butane, isobutane, or propane, and chlorinated or fluorinated hydrocarbons such as dichlorodifluoromethane and dichlorotetrafluoroethane or dimethylether; and mixtures thereof.

Examples of antiacne agents include salicylic acid, sulfur benzoyl, peroxide, tretinoin, and mixtures thereof.

Examples of antibacterial agents include chlorohexadiene gluconate, alcohol, benzalkonium chloride, benzethonium chloride, hydrogen peroxide, methylbenzethonium chloride, phenol, poloxamer 188, povidone-iodine, and mixtures thereof.

Examples of antifungal agents include miconazole nitrate, calcium undecylenate, undecylenic acid, zinc undecylenate, and mixtures thereof.

Examples of therapeutic active agents include penicillins, cephalosporins, tetracyclines, macrolides, epinephrine, amphetamines, aspirin, acetaminophen, barbiturates, catecholamines, benzodiazepine, thiopental, codeine, morphine, procaine, lidocaine, benzocaine, sulphonamides, ticonazole, perbuterol, furosamide, prazosin, hormones, prostaglandins, carbenicillin, salbutamol, haloperidol, suramin, indomethicane, diclofenac, glafenine, dipyridamole, theophylline, hydrocortisone, steroids, scopolamine, and mixtures thereof.

Examples of external analgesics are benzyl alcohol, *capsicum* oleoresin (*Capsicum frutescens* oleoresin), methyl salicylate, camphor, phenol, capsaicin, juniper tar (*Juniperus oxycedrus* tar), phenolate sodium (sodium phenoxide), *capsicum* (*Capsicum frutescens*), menthol, resorcinol, methyl nicotinate, turpentine oil (turpentine), and mixtures thereof.

An example of a skin bleaching agent is hydroquinone.

Examples of anti-cancer agents include alkylating agents (such as busulfan, fluorodopan), antimitotic agents (such as colchicine, rhizoxin), topoisomerase I inhibitors (such as camptothecin and its derivatives), topoisomerase II inhibitors (such as menogaril, amonafide), RNA/DNA or DNA anti-metabolites (such as acivicin, guuanazole), plant alkaloids and terpenoids, antineoplastics, some plant-derived compounds (such as podophyllotoxin, vinca alkaloids), and mixtures thereof.

Examples of diuretics include loop diuretics (such as bumetanide, furosemide), thiazide diuretics (such as chlorothiazide, hydroflumethiazide), potassium-sparing diuretics (such as amioloride, spironolactone), carbonic anhydrase inhibitors (such as acetazolamide), osmotic diuretics (such as mannitol), and mixtures thereof.

Examples of agents for treating gastric and duodenal ulcers include proton pump inhibitor (such as lansoprazole, omeprazole), acid blockers or H2 histamine blockers (such as cimetidine, ranitidine), bismuth, sucralfate, and mixtures thereof.

Examples of proteolytic enzymes include nattokinase, serratiopeptidase, bromelain, papain, and mixtures thereof.

Examples of antihistamine or H1 histamine blockers include brompheniramine, clemastine, cetirizine, loratadine, fexofenadine, and mixtures thereof.

Examples of sedatives include barbiturates (such as phenobarbitol), benzodiazepines (such as lorazepam), herbal sedatives, benzodiazepine-like drugs (such as zolpidem, zopiclone), and mixtures thereof.

Examples of bronchodilators include short-acting β2-agonists and long-acting β2-agonists, anticholinergics, and mixtures thereof.

The formulations may also include diluents. Such diluents are often necessary to decrease the viscosity of the formulation sufficiently for application.

Examples of diluents include silicon containing diluents such as hexamethyldisiloxane, octamethyltrisiloxane, and other short chain linear siloxanes such as octamethyltrisiloxane, decamethyltetrasiloxane, dodecamethylpentasiloxane, tetradecamethylhexasiloxane, hexadeamethylheptasiloxane, heptamethyl-3-{(trimethylsilyl)oxy)}trisiloxane, cyclic siloxanes such as hexamethylcyclotrisiloxane, octamethylcyclotetrasiloxane, decamethylcyclopentasiloxane, dodecamethylcyclohexasiloxane; organic diluents such as butyl acetate, alkanes, alcohols, ketones, esters, ethers, glycols, glycol ethers, hydrofluorocarbons or any other material which can dilute the formulation without adversely affecting any of the component materials of the cosmetic composition. Hydrocarbons include isododecane, isohexadecane, Isopar L ($C_{11}$-$C_{13}$), Isopar H ($C_{11}$-$C_{12}$), hydrogentated polydecene. Ethers and esters include isodecyl neopentanoate, neopentylglycol heptanoate, glycol distearate, dicaprylyl carbonate, diethylhexyl carbonate, propylene glycol n butyl ether, ethyl-3 ethoxypropionate, propylene glycol methyl ether acetate, tridecyl neopentanoate, propylene glycol methylether acetate (PGMEA), propylene glycol methylether (PGME), octyldodecyl neopentanoate, diisobutyl adipate, diisopropyl adipate, propylene glycol dicaprylate/dicaprate, and octyl palmitate. Additional organic diluents include fats, oils, fatty acids, and fatty alcohols.

The formulations may also include film formers. The term "film-forming polymer" means a polymer capable, by itself or in the presence of an auxiliary film-forming agent, of forming a macroscopically continuous film on a support, especially on keratin materials, preferably a cohesive film and better still a film whose cohesion and mechanical properties are such that the film can be isolated from the support. This film former can be delivered from either an oil media, aqueous media or in an emulsion form.

Examples of film formers include those polymers capable, by themselves or in the presence of an auxiliary film-forming agent, of forming a macroscopically continuous film on a support, especially on keratin materials, preferably a cohesive film and better still a film whose cohesion and mechanical properties are such that the film can be isolated from the support. Examples of film formers include silicone resins, gums, silicone acrylates, sugar siloxanes, and others.

Examples of anti-aging actives include, but are not limited to, retinol (retinoic acid, retinyl palmitate); alpha hydroxy acids ("AHAs"; e.g. glycolic acid, lactic acid, etc.), beta hydroxy acids ("BHAs"; e.g. salicylic acid); other acid (e.g. hyaluronic acid); antioxidants, such as green tea, vitamin C, vitamin E, soy, genistein, pomegranate, resveratrol, etc.; Coenzyme Q10 (Ubiquinone); peptides; extracts (e.g. grape seed extract); niacinamide; curcuminoids; ceramides; and combinations thereof.

It is thought that the carboxyl groups of the elastomer may interact with certain cosmetic components, thus providing delivery of such component's to a subject's skin. Thus, in certain embodiments, the elastomer is reacted with the at least one cosmetic component. Examples of such interactions are thought to be hydrogen bonding, coordination, and/or chemical reaction between carboxyl groups of the elastomer and a functional group of the cosmetic component.

Further materials suitable for the personal care and health care are well known to the person skilled in the art and are described in many text books as well as other publications. For example, the CTFA Cosmetic Ingredient Dictionary, Second Edition (1977), includes a number of suitable cosmetic components for this disclosure, and is thus incorporated herein by reference in its entirety.

Cosmetically Acceptable Medium

A cosmetically acceptable medium is meant to designate a medium particularly suitable for applying a composition of the disclosure on keratin materials. The cosmetically acceptable medium is generally adapted to the nature of the support on which the composition should be applied as well as to the aspect under which the composition should be conditioned and includes water, solvents, diluents, or mixtures and emulsions thereof. When utilized, the cosmetically acceptable medium can be present in an amount ranging from 0.1% to 99.9% weight percent based upon the total weight of the cosmetic composition.

Cosmetic Composition and Methods of Preparation

The general level of elastomer of any embodiment described above in the cosmetic compositions may vary from about 0.1% to about 95% by weight, optionally from about 0.2% to about 50%, optionally from about 0.5% to about 25%, relative to the total weight of the cosmetic composition. The cosmetic component is present at a level of from about 0.01% to about 99.99% by weight, relative to the total weight of the cosmetic composition. The cosmetic component may be a combination or mixture of cosmetic components as listed above.

The cosmetic composition may be prepared by a process comprising the steps of mixing the elastomer and additive according to any embodiment described above and at least one cosmetic component optionally in the presence of a cosmetically acceptable medium. In various embodiments, the elastomer and the additive are first combined to form a mixture. In certain embodiments, these are the only two components of the mixture. The additive stabilizes the elastomer and generally prevents the elastomer from structuring and/or de-structures (i.e., thins) the elastomer if already structured or beginning to structure (i.e., thicken). This is useful for ease of formulation and handling. In further embodiments, the mixture and the at least one cosmetic component are combined to form the cosmetic composition, optionally in the presence of the cosmetically acceptable medium. In these embodiments, the combining steps are generally separate.

The cosmetic compositions may be prepared by mixing the elastomer and additive in the aqueous phase with the appropriate phase components, or in the oil phase with the appropriate phase components, and optionally provide for a second phase, and mix both phases together, optionally under heating.

The process may be conducted at temperatures ranging of from 15 to 90° C., optionally of from 20 to 60° C., optionally at room temperature (at or about 25° C.), using simple propeller mixers, counter-rotating mixers, or homogenizing mixers. In general, no special equipment or processing conditions are required. Depending on the type of composition prepared, the method of preparation will be different, but such methods are understood by those skilled in the art.

The cosmetic compositions may be in the form of a cream, a gel, a powder (free flowing powder or pressed), a paste, a solid, freely pourable liquid, an aerosol. The cosmetic compositions may be in the form of monophasic systems, biphasic or alternate multi phasic systems; emulsions, e.g. oil-in-water, water-in-oil, silicone-in-water, water-in-silicone; multiple emulsions, e.g. oil-in-water-in-oil, polyol-in-silicone-in-water, oil-in-water-in-silicone.

Skin care compositions include shower gels, soaps, hydrogels, creams, lotions and balms; antiperspirants; deodorants such as sticks, soft solid, roll on, aerosol, and pumpsprays; skin creams; skin care lotions; moisturizers; facial treatments such as wrinkle control or diminishment treatments; anti-aging compositions; exfoliates; body and facial cleansers; bath oils; perfumes; colognes; sachets; sunscreens; mousses; patches; pre-shave and after-shave lotions; shaving soaps; shaving lathers; depilatories; make-ups; color cosmetics; foundations; concealers; blushes; lipsticks; eyeliners; mascaras; oil removers; color cosmetic removers, powders, and kits thereof.

Hair care compositions include shampoos, rinse-off conditioners, leave-in conditioners and styling aids, gels, sprays, pomades, mousses, waxes, cuticle coats, hair colorants, hair relaxants, hair straighteners, permanents, and kits thereof.

Nail care compositions include color coats, base coats, nail hardeners, and kits thereof.

Health care compositions may be in the form of ointments, creams, gels, mousses, pastes, patches, spray on bandages, foams and/or aerosols or the like, medicament creams, pastes or sprays including anti-acne, dental hygienic, antibiotic, healing promotive, which may be preventative and/or therapeutic medicaments, and kits thereof.

The cosmetic compositions may be used by the standard methods, such as applying them to the human or animal body, e.g. skin or hair, using applicators, brushes, applying by hand, pouring them and/or possibly rubbing or massaging the composition onto or into the body. Removal methods, for example for color cosmetics are standard methods understood in the art, including washing, wiping, peeling and the like.

The cosmetic compositions are applied topically to the desired area of the skin or hair in an amount sufficient to provide a satisfactory cleansing or conditioning of the skin or hair. The compositions may be diluted with water prior to, during, or after topical application, and then subsequently rinsed or wiped off of the applied surface, for example rinsed off of the applied surface using water or a water-insoluble substrate in combination with water.

This disclosure also comprises a method of treating keratinous substrates, such as hair or skin, by applying to it a cosmetic composition according to certain embodiments of this disclosure.

The cosmetic compositions may be used on hair in a conventional manner. An effective amount of the composition for washing or conditioning hair is applied to the hair. Such effective amounts generally range from about 1 g to about 50 g, optionally from about 1 g to about 20 g. Application to the hair typically includes working the cosmetic composition through the hair such that most or all of the hair is contacted with the cosmetic composition. These steps can be repeated as many times as desired to achieve the desired benefit.

Benefits obtained from using the cosmetic compositions on hair include one or more of the following benefits: color retention, improvement in coloration process, hair conditioning, softness, detangling ease, silicone deposition, anti-static, anti-frizz, lubricity, shine, strengthening, viscosity, tactile, wet combing, dry combing, straightening, heat protection, styling, or curl retention.

The cosmetic compositions may be used on skin in a conventional manner. An effective amount of the composition for the purpose is applied to the skin. Such effective amounts generally range from about 1 $mg/cm^2$ to about 3 $mg/cm^2$. Application to the skin typically includes working the cosmetic composition into the skin. This method for applying to the skin comprises the steps of contacting the skin with the cosmetic composition in an effective amount and then rubbing the composition into the skin. These steps can be repeated as many times as desired to achieve the desired benefit.

Benefits obtained from using the cosmetic compositions on skin include one or more of the following benefits: stability in various formulations (o/w, w/o, anhydrous), utility as an emulsifier, level of hydrophobicity, organic compatibility, Substantivity/durability, wash off resistance, interactions with sebum, performance with pigments, pH stability, skin softness, suppleness, moisturization, skin feel, long lasting, long wear, long lasting color uniformity, color enhancement, foam generation, optical effects (soft focus), stabilization of actives.

The cosmetic composition may be used to care for keratinous substrates, to cleanse, to condition, to refresh, to make up, to remove make up, or to fix hair.

INDUSTRIAL APPLICABILITY

The compositions of this disclosure are useful for a variety of end applications, and are not limited to any particular one. Examples of suitable applications include use in personal care, household care, and beauty care products. In embodiments having free carboxyl groups, the compositions can also be used for modifying organic resins or fibers and surface-treating powder. The treated surface shows high affinity with an unctuous agent. Particularly, dispersivity of powder is significantly improved. Therefore, the compositions can be useful for applications where high dispersivity of a powder is required, for example, cosmetics such as skincare and makeup products, and coatings. The compositions can also be used to enhance the aesthetics of personal care formulations for skin care and healthcare by providing a unique sensory profile upon application. The compositions can provide sensory characteristics such as a velvety, silky or powdery feel.

In addition, the compositions can be used for providing rheology modification to personal care (e.g. skin, sun, cosmetic, etc.) and healthcare formulations. The compositions also have excellent formulation versatility. Without being bound or limited to any particular theory, it is thought that potential benefits provided by, or attributable to, the compositions include, but are not limited to, one or more of the following: film forming, substantivity, durability, pigment/particle suspension and/or modification, long lasting/wear, additional chemistry, actives (e.g. drug) or inactives (e.g. fragrance) delivery/release, and combinations thereof. It is thought that the carboxyl (or carboxy) groups may interact with a subject's skin, thus providing long lasting/wear benefits of cosmetic compositions.

The following examples, illustrating the compositions and method, are intended to illustrate and not to limit the invention.

EXAMPLES

The following examples are included to demonstrate various embodiments of the invention. It should be appreciated by those of skill in the art that the techniques disclosed in the examples which follow represent techniques discovered by the inventor to function well in the practice of the invention, and thus can be considered to constitute desirable modes for its practice. However, those of skill in the art should, in light of the present disclosure, appreciate that many changes can be made in the specific embodiments which are disclosed and still obtain a like or similar result without departing from the spirit and scope of the invention. All percentages are in wt. % and all measurements are conducted at 23° C. unless indicated otherwise.

An additive ("silicone polyamide") of the following general formula, which can be formed via the components and methods described in U.S. Pat. No. RE 38,116, is provided:

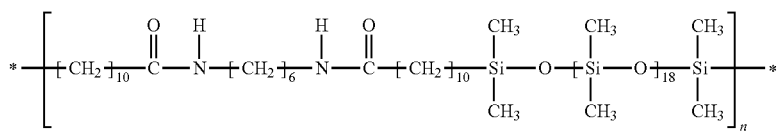

An elastomer ("carboxy elastomer") of the following general formula (of the Elastomer 1 type), which can be formed via the components and methods described in US Pat. App. Pub. No. 2016/0200876 (see, e.g., Example 15), is also provided:

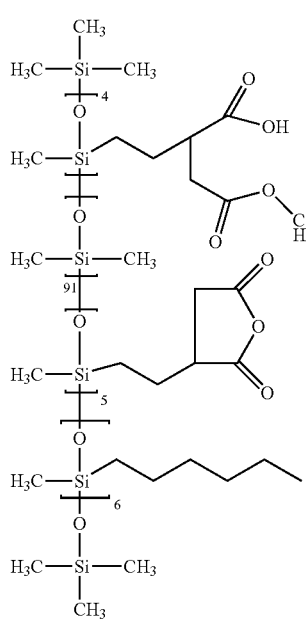
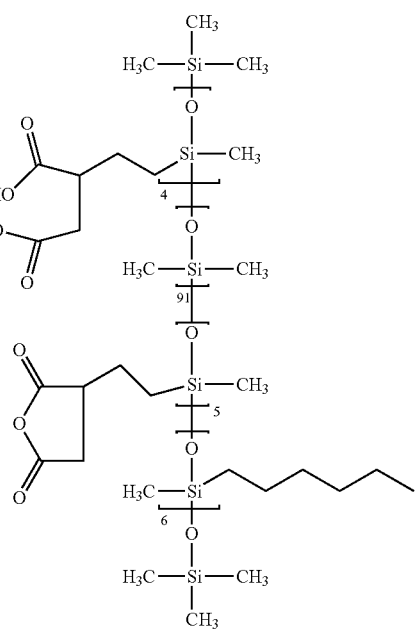

Example 1

5 grams of carboxy elastomer (30% solids in isododecane solvent (IDD)) and 0.3 grams of silicone polyamide (50% silicone polyamide in IDD, 2.83% overall polyamide) were placed in a max 20 blender cup. The material was mixed using a dental mixer for 120 seconds at 2750 rpm. The sample was observed after 24 hours and showed no visual signs of thickening or structuring.

Example 2

The procedure for evaluating durability of the carboxy elastomers was as follows: 3 grams of material from Example 1 was mixed with 0.38 grams of a pigment blend (32% pigment in IDD) in a max 20 blender cup. The material was mixed using a dental mixer for 60 seconds at 2750 rpm. Samples of pigmented carboxy elastomer polyamide blend were coated onto Vitro-Skin® from IMS at a wet thickness of 50 µm and allowed to dry for 2 hours. One drop of olive oil and one drop of artificial sebum (triolein, oleic acid and squalane (3/1/1)) were placed on the coating and allowed to sit for 2 minutes. Neither drops spread or soaked into the coating, indicating resistance to olive oil and sebum. Next, a sponge applicator was rubbed 10 times across each drop. Visual inspection noted very little rub-off of the coating and/or transfer to the sponge. The sample was observed after 24 hours and showed no visual signs of structuring. After 45 days, the pigmented sample was observed and indicated no structuring. The sample was once again coated onto Vitro-Skin® at a wet thickness of 50 µm and allowed to dry for 2 hours. One drop of olive oil and one drop of artificial sebum were placed on the coating and allowed to sit for 2 minutes. Neither drops spread or soaked into the coating, indicating resistance to olive oil and sebum. Next, a sponge applicator was rubbed 10 times across each drop. Visual inspection noted similar results as the freshly made sample. FIG. 1 shows ranking data for structuring and rub off, where 10=no rub off/no structuring, and 0=100% rub off/structuring.

Example 3

Samples of carboxy elastomer and varying amounts of silicone polyamide were prepared as follows: 6 grams of carboxy elastomer (30% solids in IDD) and silicone polyamide (33.3% polyamide in IDD at 0.25 g, 0.50 g, 0.75 g, 1.0 g and 1.25 g) were placed in max 20 blender cups. The materials were mixed using a dental mixer for 120 seconds at 2750 rpm. The samples were observed after 24 hours and data is shown in Table 1 below:

TABLE 1

Elastomer and Varying Additive Levels: Effect on Structuring

| Carboxy Elastomer (g) | 33.3% Polyamide in IDD (g) | % Polyamide | 24 hour Observation |
|---|---|---|---|
| 6 | 0.25 | 1.32 | slightly structured; shear thins easily |
| 6 | 0.5 | 2.54 | slightly structured; shear thins easily |
| 6 | 0.75 | 3.67 | not structured |
| 6 | 1 | 4.7 | not structured |
| 6 | 1.25 | 5.69 | not structured |

Example 4

Figure 2:
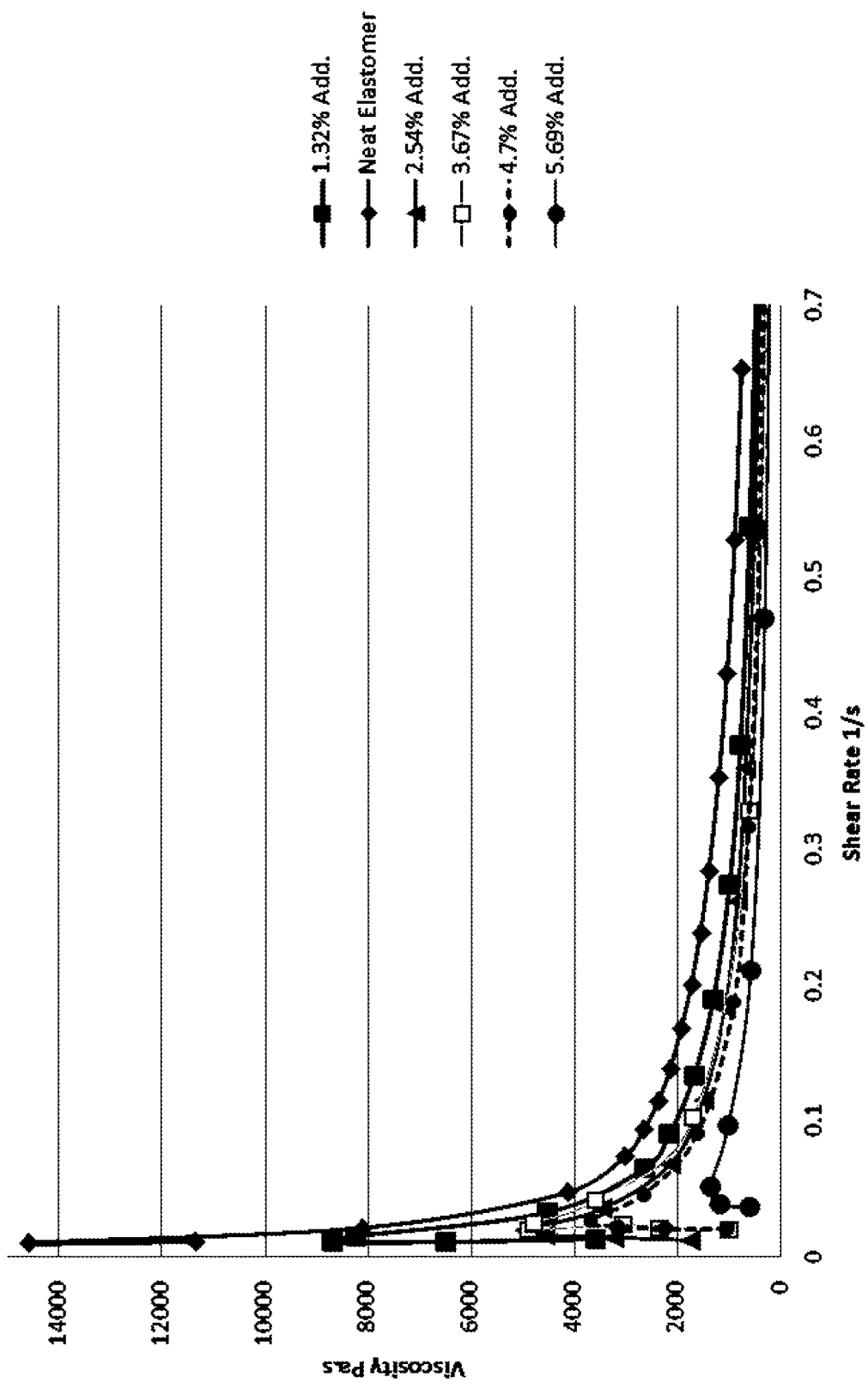
FIG. 2 is a scatter chart illustrating rheology curves of compositions comprising neat elastomer and varied levels of additive and the elastomer.

Samples from Example 3 were tested on a 60 mm Parallel Plate Rheometer. The gap was set at 1000 microns and the ramp rate was continuous. FIG. 2 indicates that with increasing polyamide levels, there is a decrease in viscosity and shear rate.

Preparation of Elastomer+Additive

Compositions comprising the elastomer(s) and additive(s) of this disclosure are made by combining and mixing the components using conventional lab equipment. Various samples of compositions having an additive amount ranging from 1 to 10, 2.5 to 5, 2.5, or 5, wt. % based on 100 parts by weight elastomer are formed. The resultant compositions, hereinafter referred to as a "COOH-elastomer+additive," are then introduced to various cosmetic formulations, with formulations and procedures for forming the particular cosmetic compositions provided below.

Use of COOH-Elastomer+Additive
Anhydrous Gel with High Level of Glycerin and Vitamin C
Formulation 1: Anhydrous Gel with High Level of Glycerin and Vitamin C

| Phase A | |
|---|---|
| PEG/PPG-19/19 Dimethicone (and) $C_{13}$-$C_{16}$ Isoparaffin (and) $C_{10}$-$C_{13}$ Isoparaffin | 4.0 |
| Caprylyl Methicone | 5.0 |
| COOH-elastomer + additive | 15.0 |
| Phase B | |
| L-ascorbic acid | 10.0 |
| Glycerin | 66.0 |
| Total Weight % | 100.0 |

Procedure:
1. Mix phase A well;
2. Heat glycerin to high temperature and add L-ascorbic acid into it under mixing until getting clear solution;
3. Drop phase B into Phase A slowly;
4. Mix final gel well.

The particularity of this gel was that it allows the incorporation of a high level of vitamin c using glycerin as a carrier, therefore to ensure the stability of the active without the drawback of the glycerin feel.

The silicone polyether (PEG/PPG-19/19 Dimethicone) can be either omitted or replaced by similar type of material such as grafted-block or block copolymers comprising at least one block of polyorganosiloxane type and at least one block of a polyether. The polyorganopolysiloxane block may especially be a polydimethylsiloxane or a poly ($C_2$-$C_8$) alkylmethylsiloxane; the polyether block may be a poly(oxy ($C_2$-$C_8$)alkylene, in particular polyoxyethylene and/or polyoxypropylene. These can also be linear rake or graft type materials, or ABA type where the B is the siloxane polymer block, and the A is the poly(oxyalkylene) group. The poly (oxyalkylene) group can consist of polyethylene oxide, polypropylene oxide, or mixed polyethylene oxide/polypropylene oxide groups. Other oxides, such as butylene oxide or phenylene oxide are also possible. Another type of silicone polyether composition that may be included in the present composition is an ABn polyalkylene oxide silicone copolymers as described in EP 492657.

Antiperspirant Gels/Soft Solids
Formulation 2.1: Antiperspirant Gel

| Phase A | |
|---|---|
| Cyclopentasiloxane (and) PEG-12 Dimethicone Crosspolymer | 10.0 |

| | |
|---|---|
| Cyclopentasiloxane | 10.0 |
| COOH-elastomer + additive | 10.0 |
| Phase B | |
| Aluminum chloride | 25.0 |
| propylene glycol | 7.0 |
| Water | 38.0 |
| Total Weight % | 100.0 |

Procedure:
1. Mix phase A well;
2. Dissolve aluminum chloride in mixture of water and propylene glycol under mixing;
3. Drop phase B into Phase A slowly;
4. Mix final gel well.

Formulation 2.2: Antiperspirant Soft Solid

| | |
|---|---|
| Phase A | |
| COOH-elastomer + additive | 33.0 |
| Phase B | |
| Aluminum chloride | 11.0 |
| Water | 22.0 |
| Phase C | |
| Glycerin | 34.0 |
| Total Weight % | 100.0 |

Procedure:
1. Dissolve aluminum chloride in water;
2. Mix Phase B and A well;
3. Add Phase C into Phase (A + B) and mix final soft solid well.

Other antiperspirant/deodorant actives could be used, such as Aluminium Zirconium Tetrachlorohydrex GLY, Aluminium Zirconium Tetrachiorohydrex PEG, Aluminium Chlorohydrex, Aluminium Zirconium Tetrachiorohydrex PG, Aluminium Chlorohydrex PEG, Aluminium Zirconium Trichlorohydrate, Aluminium Chlorohydrex PG, Aluminium Zirconium Trichlorohydrex GLY, Hexachlorophene, Benzalkonium Chloride, Aluminium Sesquichlorohydrate, Sodium Bicarbonate, Aluminium Sesquichlorohydrex PEG, Chlorophyllin-Copper Complex, Triclosan, Aluminium Zirconium Octachlorohydrate, and Zinc Ricinoleate.

The silicone polyether (PEG-12 Dimethicone cross polymer) can be either omitted or replaced by similar type of material such as grafted-block or block copolymers comprising at least one block of polyorganosiloxane type and at least one block of a polyether. The polyorganopolysiloxane block may especially be a polydimethylsiloxane or a poly $(C_2$-$C_8)$ Alkylmethylsiloxane; the polyether block may be a poly(oxy$(C_2$-$C_8)$alkylene, in particular polyoxyethylene and/or polyoxypropylene. These can also be linear rake or graft type materials, or ABA type where the B is the siloxane polymer block, and the A is the poly(oxyalkylene) group. The poly(oxyalkylene) group can consist of polyethylene oxide, polypropylene oxide, or mixed polyethylene oxide/polypropylene oxide groups. Other oxides, such as butylene oxide or phenylene oxide are also possible. Another type of silicone polyether composition that may be included in the present composition is an ABn polyalkylene oxide silicone copolymers as described in EP 492657.

Shower Gels

Formulation 3: Shower Gel

| | |
|---|---|
| Phase A | |
| Hydroxy Ethyl Cellulose | 0.4 |
| Water | 31.3 |
| Phase B | |
| Stearic acid | 1.6 |
| Myristic acid | 4.0 |
| Palmitic acid | 3.2 |
| Sodium Laureth Sulfate (and) Glycol Distearate (and) Cocamide MEA (and) Laureth-10 | 2.4 |
| COOH-elastomer + additive | 4.0 |
| Phase C | |
| Water | 39.6 |
| potassium hydroxide | 6.0 |
| Phase D | |
| Sodium Laureth Sulfate (and) Glycol Distearate (and) Cocamide MEA (and) Laureth-10 | 4.0 |
| Propylene glycol | 1.6 |
| Glycerin | 1.6 |
| Phase E | |
| Citric acid | 0.2 |
| Propylene Glycol (and) Diazolidinyl Urea (and) Methylparaben (and) Propylparaben | 0.4 |
| Total Weight % | 100.0 |

Procedure:
1. Heat water to 80° C.;
2. Disperse hydro ethyl cellulose into water slowly under mixing;
3. Mix Phase B and keep temperature of Phase B at 80° C.;
4. Add Phase A to Phase B;
5. Dissolve potassium hydroxide into water and heat solution to 80° C.;
6. Add Phase B into Phase C under mixing and keep temperature at 80° C.;
7. Add Phase D into Phase (A + B + C) and keep mixing until temperature down to 45° C.;
8. Add Phase E into Phase (A + B + C + D).

Alternative anionic surfactants can be used such as $C_6$-$C_{30}$ fatty acid salts, especially those derived from amines, for instance triethanolamine stearate; polyoxyethylenated fatty acid salts, especially those derived from amines or alkali metal salts, and mixtures thereof; phosphoric esters and salts thereof, such as DEA oleth-10 phosphate or monocetyl monopotassium phosphate sulfosuccinates such as Disodium PEG-5 citrate lauryl sulfosuccinate and Disodium ricinoleamido MEA sulfosuccinate; alkyl ether sulfates, such as sodium lauryl ether sulfate; isethionates; acylglutamates such as Disodium hydrogenated tallow glutamate, Alkyl polyglucosides and mixtures thereof.

It is also possible to use one or more amphoteric surfactants, for instance N-acylamino acids such as N-alkylaminoacetates and disodium cocoamphodiacetate, and amine oxides such as stearamine oxide, or alternatively silicone surfactants, for instance dimethicone copolyol phosphates.

The Hydroxyethylcellulose can be substituted by other water thickeners such as water-soluble cellulose-based thickeners,—guar gum, xanthan gum, carob gum, scleroglucan gum, gellan gum, rhamsan gum, karaya gum or carrageenan gum, alginates, maltodextrins, starch and its derivatives.

Rinse Off Conditioner

Formulation 4: Rinse Off Conditioner

| Phase A | |
| --- | --- |
| Hydro Ethyl Cellulose | 1.5 |
| Water | 91.9 |
| Phase B | |
| Octodecyl Trimethyl Ammonium Chloride | 0.3 |
| Cetearyl alcohol | 1.0 |
| COOH-elastomer + additive | 5.1 |
| Phase C | |
| DMDM Hydantoin | 0.2 |
| Total Weight % | 100.0 |

Procedure:
1. Heat water to 80° C.;
2. Disperse hydro ethyl cellulose into water slowly under mixing;
3. Keep temperature at 80° C.;
4. Add phase B into Phase A under mixing;
5. Add Phase C when temperature down to 45° C. and mix well.

The Hydroxyethylcellulose can be substituted by other water thickeners such as water-soluble cellulose-based thickeners, guar gum, xanthan gum, carob gum, scleroglucan gum, gellan gum, rhamsan gum, karaya gum or carrageenan gum, alginates, maltodextrins, starch and its derivatives.

Cetyl alcohol can also be replaced by other fatty alcohol such as stearyl alcohol.

Cationic polymer can also be added in order to improve the conditioning performance.

Shampoo

Formulation 5: Shampoo

| Phase A | |
| --- | --- |
| Sodium Laureth Sulfate (28%) | 32.8 |
| Cocamide Diethanolamine | 5.9 |
| PEG-150 Pentaerythrityl Tetrastearate (and) PEG-6 Caprylic/Capric Glycerides (and) Water | 5.9 |
| Cocamidopropyl Betaine (30%) | 6.6 |
| Octodecyl Trimethyl Ammonium Chloride | 0.3 |
| Lauryl Glucoside | 4.7 |
| COOH-elastomer + additive | 4.7 |
| Phase B | |
| Water | 39.3 |
| Phase C | |
| DMDM Hydantoin | 0.2 |
| Total Weight % | 100.0 |

Procedure:
1. Heat phase A to 65° C. and mix it well;
2. Heat phase B to 45° C.;
3. Add phase B into Phase A under mixing;
4. Cool Phase (A + B) to 45° C. in room temperature;
5. Add phase C into phase (A + B) and mix well.

In a similar fashion than in the shower gel, alternative surfactants and thickening agents can be used.

Water-in-Silicone Cream

Formulation 6: Water in Silicone Cream

| Phase A | |
| --- | --- |
| PEG/PPG-19/19 Dimethicone (and) C13-16 Isoparaffin (and) C10-13 Isoparaffin | 4.2 |
| COOH-elastomer + additive | 15.8 |
| Soy bean oil | 5.3 |
| Phenyl Trimethicone (and) Dimethiconol | 2.1 |
| Cyclopentasiloxane | 2.1 |
| Caprylyl Methicone | 4.2 |
| Cyclopentasiloxane (and) Polypropylsilsesquioxane | 2.1 |
| Phase B | |
| Water | 57.9 |
| Glycerin | 6.3 |
| Preservative & Fragrance | q.s. |
| Total Weight % | 100.0 |

Procedure:
1. Mix phase A and B well separately;
2. Drop phase B into phase A slowly;
3. Mix phase (A + B) well.

The silicone polyether (PEG/PPG 19/19 Dimethicone) can be either omitted or replaced by similar type of material as described in the antiperspirant Formulation 2.

The silicone gum blend (Phenyltrimethicone and Dimethiconol) can be replaced by other types of gum blends where the carrier is a silicone oil, an organic oil or a blend of both. The silicone gum blend can also be replaced by silicone elastomer gels, elastomeric solid organopolysiloxane enclosed in a fatty phase, where the at least one elastomeric solid organopolysiloxane is at least partially crosslinked, examples described in U.S. Pat. No. 5,654,362, EP 848029, EP 869142, WO2007/109240, WO2007/109260, WO2007/109282, WO2009/006091, WO2010/080755, U.S. Pat. Nos. 4,987,169, and 5,760,116.

The volatile silicone oil (cyclopentasiloxane and Caprylyl methicone) can be replaced by any "volatile oil" corresponding to the following definition: oil (or non-aqueous medium) capable of evaporating on contact with the skin in less than one hour, at room temperature and atmospheric pressure. The volatile oil is a volatile cosmetic oil, which is liquid at room temperature, especially having a non-zero vapor pressure, at room temperature and atmospheric pressure, in particular having a vapor pressure ranging from 0.13 Pa to 40000 Pa (10-3 to 300 mmHg), optionally ranging from 1.3 Pa to 13000 Pa (0.01 to 100 mmHg), optionally ranging from 1.3 Pa to 1300 Pa (0.01 to 10 mm Hg).

The vegetable oil (soybean oil) can be replaced by a nonvolatile oil which can be hydrocarbon based, silicone based or vegetable based including esters and triglycerides.

The film forming polymer (Polypropylsilsesquioxane) can be replaced by any other film former corresponding to the film-forming polymer definition above. This film former can be delivered from either an oil media, aqueous media or in an emulsion form.

Oil-in-Water Cream

Formulation 7.1: Oil-in-Water Cream

| Phase A | |
| --- | --- |
| Glyceryl Stearate (and) Cetearyl Alcohol (and) Sodium Lauroyl Lactylate, Lecithin | 3.7 |

-continued

| | |
|---|---|
| *Simmondsia Chinensis* Oil | 7.4 |
| *Macadamia Ternifilia* Seed Oil | 7.4 |
| COOH-elastomer + additive | 11.0 |
| Phase B | |
| Water | 51.5 |
| Glycerin | 2.2 |
| Phase C | |
| Glycerine (and) Water (and) Urea (and) Trehalose (and) Polyquaternium-51 (and) Sodium Hyaluronate | 5.1 |
| *Bacopa monniera* extract (and) Aqua (water) (and) PEG 8 (and) Hydroxyethylcellulose | 2.2 |
| Butylene glycol (and) water (and) Laureth-3 hydroxyethylcellulose (and) acetyl dipeptide-1 cetyl ester | 2.9 |
| PEG-4 (and) lactic acid (and) kojic acid (and) butylene glycol (and) *morus bombycis* (and) *arctostaphylos uva-ursi* (and) *glycyrrhiza glabra* | 0.7 |
| Aqua (and) *acacia senegal* gum (and) hydrolysed soy protein (and) xanthan gum | 0.7 |
| Butylene glycol (and) water (and) Laureth-3 hydroxyethylcellulose (and) acetyl dipeptide-1 cetyl ester | 1.5 |
| Phase D | |
| Betaine | 1.5 |
| Water | 2.2 |
| Phase E | |
| Benzyl Alcohol (and) Methylchloroisothiazolinone (and) Methylisothiazolinone | 0.1 |
| Total Weight % | 100.0 |

Procedure:
1. Heat phase A and to 80° C.;
2. Mix phase B and heat it to 80° C.;
3. Pour phase A into phase B under mixing;
4. Mix phase (A + B) well until getting homogenized lotion;
5. Keep mixing and cool mixture of phase (A + B) above to 45° C. in room temperature;
6. Add phase C into Phase (A + B);
7. Mix phase D and add phase D into phase (A + B + C);
8. Add phase E into Phase (A + B + C + D);
9. Keep mixing until getting homogenized cream.

Formulation 7.2: Oil-in-Water Cream (2)

| | |
|---|---|
| Phase A | |
| Sodium Polyacrylate (and) Dimethicone (and) Cyclopentasiloxane (and) Trideceth-6 (and) PEG/PPG-18/18 Dimethicone | 2.1 |
| Caprylic/Capric Triglyceride | 7.1 |
| *Simmondsia Chinensis* Oil | 3.6 |
| Olive Oil | 2.1 |
| Bis-hydroxyethoxypropyl Dimethicone | 2.8 |
| Dimethicone (and) Dimethiconol | 2.1 |
| CI 77891 & Hydrogenated lecithin | 1.1 |
| Phase B | |
| Hydro Ethyl Cellulose | 0.2 |
| Water | 64.4 |
| L-ascorbic acid | 0.2 |
| Glycerin | 1.6 |
| COOH-elastomer + additive | 12.5 |
| Benzyl Alcohol, methylchloroisothiazolinone, methylisothiazolinone | 0.2 |
| Total Weight % | 100.0 |

Procedure:
1. Mix phase A well;
2. Heat water to 75° C. and disperse hydro ethyl cellulose into water under mixing;
3. Mix phase B well;
4. Add phase B to phase A under mixing;
5. Keep mixing until getting homogenized cream.

Formulation 7.3: Oil-in-Water Cream (3)

| | |
|---|---|
| Phase A | |
| Glyceryl Stearate (and) Cetearyl Alcohol (and) Sodium Lauroyl Lactylate, Lecithin | 4.0 |
| COOH-elastomer + additive | 6.0 |
| Caprylyl Methicone | 6.0 |
| Mineral Oil | 8.0 |
| Phase B | |
| Water | 69.8 |
| Glycerin | 6.0 |
| Phase C | |
| Benzyl Alcohol (and) Methylchloroisothiazolinone (and) Methylisothiazolinone | 0.2 |
| Total Weight % | 100.0 |

Procedure:
1. Heat phase A and to 80° C.;
2. Mix phase B and heat it to 80° C.;
3. Pour phase A into phase B under mixing;
4. Mix phase (A + B) well until getting homogenized lotion;
5. Keep mixing and cool mixture of phase (A + B) to 45° C. in room temperature;
6. Add phase C into Phase (A + B);
7. Keep mixing until getting homogenized cream.

The thickening/emulsifying polymer dispersion (Sodium polyacrylate) can be replaced by crosslinked acrylamide polymers and copolymers, such as Sepigel 305 and by the carbomer families.

The oils (Caprylic/Capric triglycerides, Olive oil and Jojoba oil) can be replaced by a nonvolatile oil which can be hydrocarbon based, silicone based or vegetable based including esters and triglycerides The pigment (CI 77891 (and) Hydrogenated Lecithin) can be replaced by any other pigment included in the following definitions:

The term "pigments" should be understood as meaning white or colored, mineral or organic particles of any form, which are insoluble in the physiological medium, and which are intended to color the composition.

The term "nacres" should be understood as meaning iridescent particles of any form, produced especially by certain mollusks in their shell, or else synthesized.

The pigments may be white or colored, and mineral and/or organic.

In addition, these pigments could be treated/coated by a wide range of chemicals.

Oil-in-Water Foundations

Formulation 8.1: Oil-in-Water Foundation

| | |
|---|---|
| Phase A | |
| Steareth-21 | 1.5 |
| Steareth-2 | 1.5 |
| Stearic acid | 3.0 |
| Caprylic/Capric Triglyceride | 3.0 |
| Mineral Oil | 3.0 |
| Cyclopentasiloxane (and) Acrylates/Polytrimethylsiloxymethacrylate Copolymer | 4.0 |
| Pigment (Titanium dioxide, Talc, Dimethicone) | 9.0 |
| COOH-elastomer + additive | 15.0 |
| Phase B | |
| Hydro Ethyl Cellulose (2.5% solution) | 10.0 |
| Water | 41.8 |
| Bis-PEG-18 Methyl Ether Dimethyl Silane | 2.0 |
| Glycerin | 6.0 |

-continued

| Phase C | |
| --- | --- |
| Benzyl Alcohol, methylchloroisothiazolinone, methylisothiazolinone | 0.2 |
| Total Weight % | 100.0 |

Procedure:
1. Mix phase A well and heat to 80° C.;
2. Heat water to 75° C. and disperse hydro ethyl cellulose into water under mixing;
3. Mix phase B well and keep temperature as 75° C.;
4. Add phase A to phase B under mixing;
5. Keep mixing until getting homogenized product and cool it to 45° C.;
6. Add phase C into Phase (A + B) and mix it well.

Formulation 8.2: Oil-in-Water Foundation (2)

| Phase A | |
| --- | --- |
| Glycerol monostearate | 3.0 |
| Stearic acid | 3.0 |
| Caprylic/Capric Triglyceride | 3.0 |
| Mineral Oil | 3.0 |
| Phase B | |
| Cyclopentasiloxane (and) Acrylates/Polytrimethyl-siloxymethacrylate Copolymer | 4.0 |
| Pigment (Titanium dioxide, Talc, Dimethicone) | 9.0 |
| Phase C | |
| Water | 51.8 |
| Glycerin | 8.0 |
| Phase D | |
| COOH-elastomer + additive | 15.0 |
| Phase E | |
| Phenoxyethanol (and) Methylparaben (and) Ethylparaben (and) Butylparaben (and) Propylparaben (and) Isobutylparaben | 0.2 |
| Total Weight % | 100.0 |

Procedure:
1. Mix phase A well and heat to 80° C.;
2. Mix phase B well and add phase B to phase A under mixing;
3. Keep temperature of phase (A + B) as 75° C.;
4. Heat phase C to 75° C.;
5. Add phase (A + B) to phase C under mixing;
6. Keep mixing until getting homogenized product and cool it to 45° C.;
7. Add phase D into Phase (A + B + C) and mix it well;
8. Add phase E into Phase (A + B + C + D) and mix it well.

The nonionic emulsifiers blend (Steareth-2, Steareth-21 and Glyceryl Stearate (and) PEG-100 Stearate) can be replaced by any other oxyethylenated and/or oxypropylenated ethers (which may comprise from 1 to 150 oxyethylene and/or oxypropylene groups) of glycerol; oxyethylenated and/or oxypropylenated ethers (which may comprise from 1 to 150 oxyethylene and/or oxypropylene groups) of fatty alcohols (especially of a $C_8$-$C_{24}$ and optionally $C_{12}$-$C_{18}$ alcohol), such as oxyethylenated cetearyl alcohol ether containing 30 oxyethylene groups (CTFA name Ceteareth-30) and the oxyethylenated ether of the mixture of $C_{12}$-$C_{15}$ fatty alcohols comprising 7 oxyethylene groups (CTFA name $C_{12}$-$C_{15}$ Pareth-7); fatty acid esters (especially of a $C_8$-$C_{24}$ and optionally $C_{16}$-$C_{22}$ acid) of polyethylene glycol (which may comprise from 1 to 150 ethylene glycol units), such as PEG-50 stearate and PEG-40 monostearate; fatty acid esters (especially of a $C_8$-$C_{24}$ and optionally $C_{16}$-$C_{22}$ acid) of oxyethylenated and/or oxypropylenated glyceryl ethers (which may comprise from 1 to 150 oxyethylene and/or oxypropylene groups), for instance PEG-200 glyceryl monostearate; glyceryl stearate polyethoxylated with 30 ethylene oxide groups, glyceryl oleate polyethoxylated with 30 ethylene oxide groups, glyceryl cocoate polyethoxylated with 30 ethylene oxide groups, glyceryl isostearate polyethoxylated with 30 ethylene oxide groups, and glyceryl laurate polyethoxylated with 30 ethylene oxide groups; fatty acid esters (especially of a $C_8$-$C_{24}$ and optionally $C_{16}$-$C_{22}$ acid) of oxyethylenated and/or oxypropylenated sorbitol ethers (which may comprise from 1 to 150 oxyethylene and/or oxypropylene groups), dimethicone copolyol; dimethicone copolyol benzoate; copolymers of propylene oxide and of ethylene oxide, also known as EO/PO polycondensates; and mixtures thereof; saccharide esters and ethers, such as sucrose stearate, sucrose cocoate and sorbitan stearate, and mixtures thereof, fatty acid esters (especially of a $C_8$-$C_{24}$ and optionally $C_{16}$-$C_{22}$ acid) of polyols, especially of glycerol or of sorbitol, such as glyceryl stearate, glyceryl stearate, glyceryl laurate, polyglyceryl-2 stearate, sorbitan tristearate or glyceryl ricinoleate.

The stearic acid can be replaced by other waxes corresponding to the following definition: lipophilic compound that is solid at room temperature (25° C.), which undergoes a reversible solid/liquid change of state, and which has a melting point of greater than or equal to 30° C., which may be up to 120° C. By bringing the wax to the liquid state (melting), it is possible to make it miscible with the oils that may be present and to form a microscopically homogeneous mixture, but on reducing the temperature of the mixture to room temperature, recrystallization of the wax in the oils of the mixture takes place.

The oils (Caprylic/Capric triglycerides and Mineral oil) can be replaced by a nonvolatile oil which can be hydrocarbon based, silicone based or vegetable based including esters and triglycerides The film forming polymer (Acrylates/Polytrimethylsiloxymethacrylate Copolymer) can be replaced by any other film former corresponding to the film-forming polymer definition above. This film former can be delivered from either an oil media, aqueous media or in an emulsion form.

The pigment (CI 77891 (and) Hydrogenated Lecithin) can be replaced by any other pigment as described in formulation 7.

Loose Powder

Formulation 9: Loose Powder

| Phase A | |
| --- | --- |
| Talc | 68.0 |
| Titanium dioxide | 12.0 |
| Pigment (CI 15850, triethoxycaprylysilane; CI 42090 & Triethoxycaprylylsilane; Iron oxides (and) hydrogenated lecithin) | 3.0 |
| HDI/Trimethylol Hexyllactone Crosspolymer (And) Silica | 5.0 |
| Dimethicone/Vinyldimethicone Crosspolymer (and) Silica | 1.0 |
| Mica | 1.5 |
| CI 77891 & CI 77491 & Mica & Triethoxycaprylylsilane | 1.0 |
| COOH-elastomer + additive | 5.5 |
| Dimethicone | 3.0 |
| Total Weight % | 100.0 |

Procedure:
1. Add component one by one to the pigment mixer;
2. Mix all components well.

The fillers (Talc, BPD 500, Mica and submica) can be replaced by the following other filler families: mineral or organic, of any form, platelet-shaped, spherical or oblong, irrespective of the crystallographic form (for example lamellar, cubic, hexagonal, orthorhombic, etc.) such as silica, kaolin, polyamide, poly-β-alanine powder and polyethylene powder, tetrafluoroethylene polymer (Teflon®) powders, lauroyllysine, starch, boron nitride, hollow polymer microspheres, or of acrylic acid copolymers and silicone resin microbeads, elastomeric polyorganosiloxane particles, elastomeric organopolysiloxane powder coated with silicone resin, especially with silsesquioxane resin, hybrid silicone powders functionalized with fluoroalkyl groups, phenyl groups, precipitated calcium carbonate, magnesium carbonate, magnesium hydrogen carbonate, hydroxyapatite, hollow silica microspheres, glass or ceramic microcapsules, and metal soaps for example zinc stearate, magnesium stearate, lithium stearate, zinc laurate or magnesium myristate, polymethyl methacrylate powders, polyurethane powder as well as fibers defined as the following: "fibre" or "fiber" should be understood as meaning an object of length L and diameter D such that L is very much greater than D, D being the diameter of the circle in which the cross section of the fibre is inscribed.

The pigments (Iron Oxides, $TiO_2$ and Covapealantique) can be replaced by any other pigment as described in formulation 7.

Silicone oil (dimethicone) can be replaced by a nonvolatile oil which can be hydrocarbon based, silicone based or vegetable based including esters and triglycerides.

Lip Gloss

Formulation 10: Lip Gloss

| Phase A | |
|---|---|
| Dimethicone | 15.0 |
| Cyclopentasiloxane (and) Dimethiconol | 39.9 |
| Phenyltrimethicone | 6.0 |
| Bis-hydroxyethoxypropyl Dimethicone | 12.0 |
| Dimethicone (and) Trimethylsiloxysilicate | 8.0 |
| Olive oil | 2.0 |
| Ethylhexyl Salicylate | 6.0 |
| COOH-elastomer + additive | 11.0 |
| Phase B | |
| Silica silylate | 0.3 |
| Total Weight % | 100.0 |

Procedure:
1. Add component in phase A one by one in order under mixing;
2. Mix phase A well 75° C.;
3. Add phase B into phase A under mixing;
4. Mix phase (A + B) well.

Silicone and natural oils (Dimethicone, Phenyltrimethicone, Bis-hydroxyethoxypropyl Dimethicone, olive oil) can be replaced by a nonvolatile oil which can be hydrocarbon based, silicone based or vegetable based including esters and triglycerides.

Silicone gum blend (Cyclopentasiloxane and Dimethiconol) can be replaced by other gum blends or elastomer blends as described in Formulation 6.

Silicone resin (Trimethylsiloxysilicate) can be replaced by other film formers as described in Formulation 8.

Silica (silica silylate) can be replaced by other fillers as described in Formulation 9.

The pigments (Iron Oxides, $TiO_2$) can be replaced by any other pigment as described in Formulation 7.

Sunscreen (Ethylhexyl Salicylate) can be replaced by any other liquid organic sunscreens.

Cosmetic Paste

Formulation 11.1: Blemish Spot Treatment Paste

| Phase A | |
|---|---|
| Stearyl Dimethicone | 10.0 |
| $C_{30-45}$ Alkyldimethylsilyl polypropylsilsesquioxane | 12.0 |
| Phase B | |
| Caprylyl Methicone | 25.0 |
| Bis-hydroxyethoxypropyl Dimethicone | 10.0 |
| Dimethicone/Vinyldimethicone Crosspolymer (and) Silica | 10.0 |
| Titanium dioxide | 13.0 |
| Castor oil, CI19140 | 10.0 |
| COOH-elastomer + additive | 10.0 |
| Total Weight % | 100.0 |

Procedure:
1. Heat phase A to 70° C.;
2. Add components in phase B one by one to phase A under mixing and keep temperature;
3. Keep temperature and mix phase (A + B) well;
4. Pour to package bottle and cool to room temperature.

Formulation 11.2: Blemish Treatment Paste (2)

| Phase A | |
|---|---|
| Stearyl Dimethicone | 10.0 |
| $C_{30}$-$C_{45}$ Alkyldimethylsilyl polypropylsilsesquioxane | 12.0 |
| Phase B | |
| Bis-hydroxyethoxypropyl Dimethicone | 10.0 |
| Dimethicone/Vinyldimethicone Crosspolymer (and) Silica | 10.0 |
| Titanium dioxide | 13.0 |
| Castor oil, CI19140 | 10.0 |
| Phase C | |
| Water | 25.0 |
| COOH-elastomer + additive | 10.0 |
| Total Weight % | 100.0 |

Procedure:
1. Heat phase A to 70° C.;
2. Add components in phase B one by one to phase A under mixing and keep temperature;
3. Keep temperature and mix phase (A + B) well;
4. Mix phase C well;
5. Add phase C into Phase (A + B) under mixing;
6. Cool to room temperature.

Silicone oils (Caprylyl Methicone, Bis-hydroxyethoxypropyl Dimethicone) can be replaced by a volatile and nonvolatile oils which can be hydrocarbon based, silicone based or vegetable based including esters and triglycerides.

Silicone wax ($C_{30}$-$C_{45}$ Alkyldimethylsilyl Polypropylsilsesquioxane) can be replaced by other waxes as described in Formulation 8.

Alkyl methyl Silicone (Stearyl Dimethicone) can be replaced by any other alkylmethylsiloxanes, siloxane polymers generally having the formula $Me_3SiO[Me_2SiO]_y[MeR-SiO]_zSiMe_3$, in which R is a hydrocarbon group containing 6-30 carbon atoms, Me represents methyl, and the degree of polymerization (DP), i.e., the sum of y and z is 3-50. These alkylmethysiloxanes can be volatile, nonvolatile and solid at room temperature.

The pigments (Iron Oxides, $TiO_2$) can be replaced by any other pigment either pure or pre-dispersed in a carrier as described in Formulation 7.

Lipstick

Formulation 12: Lipstick

| Phase A | |
| --- | --- |
| Ozocerite | 4.0 |
| Carnauba wax | 11.0 |
| Petrolatum | 4.0 |
| Bee wax | 4.0 |
| Lanolin | 2.0 |
| Candelilla wax | 1.0 |
| Microcrystalline Wax | 1.0 |
| *Euphorbia Cerifera* & Isopropyl Palmitate & Ozokerite & Cetearyl Ethylhexanoate & Isostearyl Alcohol & *Copernicia Cerifera* & Myrystyl Lactate & Synthetic Beeswax & BHT | 10.0 |
| $C_{30}$-$C_{45}$ Alkyldimethylsilyl polypropylsilsesquioxane | 5.0 |
| COOH-elastomer + additive | 19.0 |
| Phase B | |
| Hydrogenated dimer Dilinoleyl/Dimethylcarbonate Copolymer | 14.0 |
| Oleyl Alcohol | 8.0 |
| Caprylyl Methicone | 9.0 |
| Pigment (Iron Oxide, CI331700, CI 77891, CI 73360, Titanium Dioxide) | 10.0 |
| Total Weight % | 100.0 |

Procedure:
1. Using pigment mixer mix all pigments well;
2. Melt all components in phase A and mix well;
3. Mix phase B well;
4. Add phase B to phase A and mix well;
5. Pour phase (A + B) into lipstick mold;
6. Put mold to refrigerator and keep for 15 minutes;
7. Take lipstick out of mold and package it.

Waxes (Ozokerite, Carnauba wax, Beeswax, Candelilla wax, Microcrystalline and $C_{30-45}$ methicone) can be replaced by other waxes as described in Formulation 8.

Oleyl alcohol can also be replaced by other fatty alcohol such as stearyl alcohol, cetyl alcohol.

Film forming polymer (Hydrogenated dimer Dilinoleyl/Dimethylcarbonate Copolymer) can be replaced by any other film former corresponding to the film-forming polymer definition above.

The pigments (Iron Oxides) can be replaced by any other pigment as described in Formulation 7.

W/O Foundation

Formulation 13: W/O Foundation

| Phase A | |
| --- | --- |
| Bis-Isobutyl PEG/PPG-10/7/Dimethicone Copolymer | 2.0 |
| $C_{30}$-$C_{45}$ Alkyldimethylsilyl polypropylsilsesquioxane | 2.0 |
| COOH-elastomer + additive | 20.0 |
| Trimethylsiloxy silicate (and) Polypropyl silsesquioxane | 1.0 |
| Isododecane | 1.0 |
| Phase B | |
| Water | 46.0 |
| Glycerin | 15.0 |
| Sodium chloride | 1.0 |

| Phase C | |
| --- | --- |
| Caprylyl Methicone | 5.0 |
| Pigment (Iron Oxide, Titanium Dioxide) | 7.0 |
| Total Weight % | 100.0 |

Procedure:
1. Using pigment mixer mix all pigments well;
2. Mix phase C well;
3. Mix phase B well;
4. Heat Phase A to melt wax and mix phase A well;
5. Add phase C to phase A and mix well;
6. Drop phase B to phase (A + C) slowly under mixing;
7. Mix foundation well until homogenized.

The silicone polyether (Bis-Isobutyl PEG/PPG-10/7/Dimethicone Copolymer) can be either omitted or replaced by similar type of material as described in the antiperspirant formulation number 2.

Silicone wax ($C_{30}$-$C_{45}$ Alkyldimethylsilyl Polypropylsilsesquioxane) can be replaced by other waxes as described in Formulation 8.

Film forming polymer (Trimethylsiloxysilicate and polypropylsilsesquioxane) can be replaced by any other film former corresponding to the film-forming polymer definition above.

The volatile silicone oil (Caprylyl methicone) can be replaced by any "volatile oil" as described in Formulation 6.

The pigments (Iron Oxides) can be replaced by any other pigment as described in Formulation 7.

Clear Gel

Formulation 14: Clear Gel

| Phase A | |
| --- | --- |
| Glycerin | 42.1 |
| Water | 27.0 |
| Phase B | |
| COOH-elastomer + additive | 30.9 |
| Total Weight % | 100.0 |

Procedure:
1. Mix phase A well;
2. Add phase A to phase B and mix well.

This clear gel is obtained by matching the refractive index of the water phase to the one of the silicone organic blend elastomer gel carrier with the help of glycerin. Other glycols such as propylene glycol, butylene glycol, dipropylene glycol or even ethanol or isopropyl alcohol can be used. Also, any other water soluble components impacting the Refractive index of the aqueous phase can also be used such as aluminium salt, sugar, etc.

Anhydrous Sunscreen

Formulation 15: Anhydrous Sun Care Gel

| Phase A | |
| --- | --- |
| COOH-elastomer + additive | 67.4 |
| Phase B | |
| Ethylhexyl Methoxycinnamate | 7.5 |
| Ethylhexyl salicylate | 5.0 |
| Capryllic/Capric Triglyceride | 8.0 |
| Dicaprylyl Carbonate | 12.0 |

-continued

| Phase C | |
|---|---|
| Silica silylate | 0.1 |
| Total Weight % | 100.0 |

Procedure:
1. Mix all components in phase B well;
2. Add phase B to phase A under mixing;
3. Add phase C to phase (A + B) and mix well.

The oil (Caprylic/Capric triglycerides) can be replaced by a nonvolatile oil which can be hydrocarbon based, silicone based or vegetable based including esters and triglycerides.

Silica (silica silylate) can be replaced by other fillers as described in Formulation 9.

Sunscreens (Ethylhexyl salycilate and Ethylhexyl Methoxycinnamate) can be replaced by any other liquid organic sunscreens.

The different formulations described in this patent illustrate the great versatility and ease of formulating of the new silicone organic elastomer blend, overcoming potential limitations of the previous elastomers gels by providing ideal balance between compatibility with the major components used in cosmetic and the unique texture and feel.

The following additional embodiments are provided, the numbering of which is not to be construed as designating levels of importance.

Embodiment 1 relates to a composition comprising: (a) an elastomer having a moiety according to the general formula: A-B-A or B-A-B; wherein each A independently comprises a polysiloxane moiety having at least two siloxy (Si—O) groups; wherein each B independently comprises a moiety, or a precursor thereof, having at least one carboxyl group; and wherein B is bonded to a silicon atom in A; and (b) an additive for stabilizing the elastomer.

Embodiment 2 relates to a composition comprising: (a) an elastomer having at least two siloxy (Si—O) groups and at least one carboxyl group, the elastomer comprising the reaction product of a reaction of: a first component having at least one reactive group; a second component having at least one reactive group; and a third component having at least two reactive groups reactive with the reactive groups of the first and second components for linking the first component to the second component; and (b) an additive for stabilizing the elastomer.

Embodiment 3 relates to the composition as set forth in Embodiment 1 or 2, further defined as a cosmetic composition, wherein the cosmetic composition further comprises: (c) at least one cosmetic component; (d) optionally in a cosmetically acceptable medium.

Embodiment 4 relates to the composition as set forth in Embodiment 1 or 3, wherein each B independently comprises a moiety, or a precursor thereof, having at least two carboxyl groups.

Embodiment 5 relates to the composition as set forth in any one of the preceding Embodiments, wherein the additive is solid at room temperature (about 25° C.), optionally has a melting point greater than 25° C.

Embodiment 6 relates to the composition as set forth in any one of the preceding Embodiments, wherein the additive comprises a silicon-based wax, an organic-based wax, or combinations thereof.

Embodiment 7 relates to the composition as set forth in any one of Embodiments 1 to 5, wherein the additive comprises a siloxane-based polyamide.

Embodiment 8 relates to the composition as set forth in any one of the preceding Embodiments, wherein the additive is present in an amount of from about 0.01 to about 100 parts by weight, optionally of from about 1 to about 50 parts by weight, based on 100 parts by weight of the elastomer.

Embodiment 9 relates to the composition as set forth in any one of Embodiments 2 to 8, wherein the at least one reactive group of the first and second components is independently selected from a hydroxyl group or an amine group and wherein the at least two reactive groups of the third component are anhydride groups.

Embodiment 10 relates to the composition as set forth in any one of Embodiments 2 to 9, wherein the first and second components are selected from siloxanes having at least one hydroxyl group or organic alcohols having at least one hydroxyl group and the third component is a siloxane having at least two terminal anhydride groups.

Embodiment 11 relates to the composition as set forth in any one of Embodiments 2 to 9, wherein the first and second components are selected from siloxanes having at least one amine group or organic amines having at least one amine group and the third component is a siloxane having at least two pendant anhydride groups.

Embodiment 12 relates to the composition as set forth in any one of Embodiments 2 to 8, wherein the at least one reactive group of the first and second components are anhydride groups and wherein the at least two reactive groups of the third component are hydroxyl groups or amine groups.

Embodiment 13 relates to the composition as set forth in Embodiment 12, wherein the first and second components are siloxanes and the anhydride groups are pendant.

Embodiment 14 relates to the composition as set forth in Embodiment 12 or 13, wherein the third component is selected from: i) an organic polyol having at least two hydroxyl groups; ii) a third siloxane having at least two hydroxyl groups; iii) an organic polyamine having at least two amine groups; or iv) a third siloxane having at least two amine groups.

Embodiment 15 relates to the composition as set forth in any one of Embodiments 1 to 8, wherein the elastomer is according to the general formula:

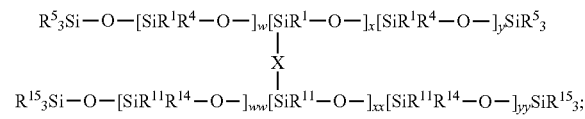

wherein each of $R^1$, $R^4$, $R^5$, $R^{11}$, $R^{14}$, and $R^{15}$ is independently a substituted or unsubstituted hydrocarbyl group, each of w and ww is an independently selected integer from zero (0) to 1,000, each of x and xx is an independently selected integer from 1 to 100, each of y and yy is an independently selected integer from 0 to 1,000, and X is of the following general formula:

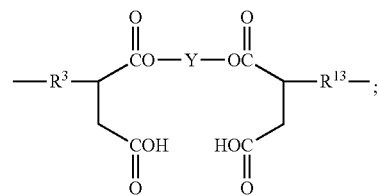

wherein each Y is a divalent group and wherein each of $R^3$ and $R^{13}$ is independently a divalent group.

Embodiment 16 relates to the composition as set forth in any one of Embodiments 1 to 8, wherein the elastomer is according to the general formula:

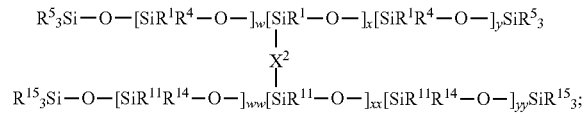

wherein each of $R^1$, $R^4$, $R^5$, $R^{11}$, $R^{14}$, and $R^{15}$ is independently a substituted or unsubstituted hydrocarbyl group, each of w and ww is an independently selected integer from zero (0) to 1,000, each of x and xx is an independently selected integer from 1 to 100, each of y and yy is an independently selected integer from 0 to 1,000, and $X^2$ is of the following general formula:

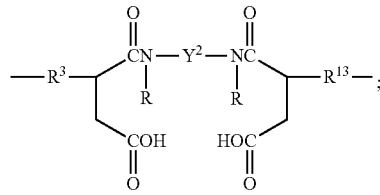

wherein each $Y^2$ is an divalent group and wherein each R is independently a hydrogen atom (H) or $R^1$ and wherein each of $R^3$ and $R^{13}$ is independently a divalent group.

Embodiment 17 relates to the composition as set forth in any one of Embodiments 1 to 8, wherein the elastomer is according to the general formula:

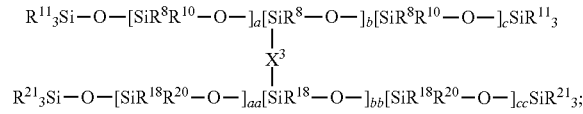

wherein each of $R^8$, $R^{10}$, $R^{11}$, $R^{18}$, $R^{20}$, and $R^{21}$ is independently a substituted or unsubstituted hydrocarbyl group, each of a and aa is an independently selected integer from zero (0) to 1,000, each of b and bb is an independently selected integer from 1 to 1000, each of c and cc is an independently selected integer from 0 to 1,000, and $X^3$ is of the following general formula:

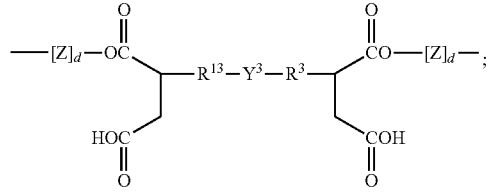

wherein each $Y^3$ is of the following general formula: $—SiR^5_2—O—[SiR^1R^4—O—]_w[SiR^1R^0—O—]_x[SiR^1R^4—O—]_ySiR^5_2—$; wherein each of $R^0$, $R^1$, $R^4$, and $R^5$ is independently a substituted or unsubstituted hydrocarbyl group; each of Z, $R^3$, and $R^{13}$ is independently a divalent group; each d is independently 0 or 1; w is an integer selected from 0 to 1,000; x is an integer selected from 0 to 100; and y is an integer selected from 0 to 1,000.

Embodiment 18 relates to the composition as set forth in any one of Embodiments 1 to 8, wherein the elastomer is according to the general formula:

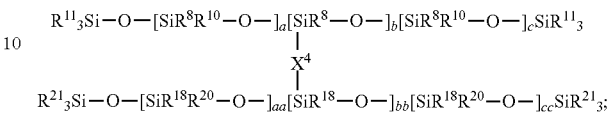

wherein each of $R^8$, $R^{10}$, $R^{11}$, $R^{18}$, $R^{20}$, and $R^{21}$ is independently a substituted or unsubstituted hydrocarbyl group, each of a and aa is an independently selected integer from zero (0) to 1,000, each of b and bb is an independently selected integer from 1 to 1000, each of c and cc is an independently selected integer from 0 to 1,000, and $X^4$ is of the following general formula:

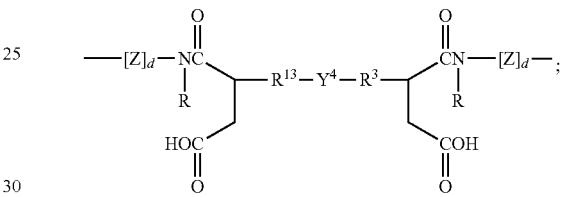

wherein each $Y^4$ is of the following general formula: $—SiR^5_2—O—[SiR^1R^4—O—]_w[SiR^1R^0—O—]_x[SiR^1R^4—O—]_ySiR^5_2—$; wherein each of $R^0$, $R^1$, $R^4$, and $R^5$ is independently a substituted or unsubstituted hydrocarbyl group; each of Z, $R^3$, and $R^{13}$ is independently a divalent group; each R is independently a hydrogen atom (H) or $R^1$; each d is independently 0 or 1; w is an integer selected from 0 to 1,000; x is an integer selected from 0 to 100; and y is an integer selected from 0 to 1,000.

Embodiment 19 relates to the composition as set forth in any one of Embodiments 1 to 8, wherein the elastomer is according to the general formula:

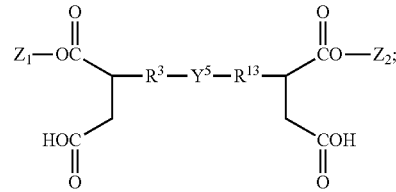

wherein each $Y^5$ is of the following general formula: $—SiR^5_2—O—[SiR^1R^4—O—]_w[SiR^1R^0—O—]_x[SiR^1R^4—O—]_ySiR^5_2—$; wherein each of $Z_1$ and $Z_2$ is independently attributable to an organic alcohol having at least one hydroxyl group, each of $R^3$ and $R^{13}$ is independently a divalent group, each of $R^0$, $R^1$, $R^4$, and $R^5$ is independently a substituted or unsubstituted hydrocarbyl group, w is an integer selected from zero (0) to 1,000, x is an integer selected from 0 to 100, and y is an integer selected from 0 to 1,000.

Embodiment 20 relates to the composition as set forth in any one of Embodiments 1 to 8, wherein the elastomer is according to the general formula:

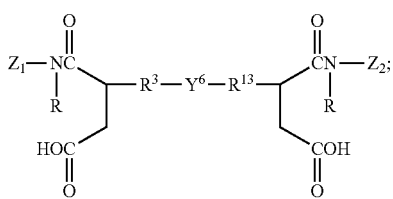

wherein each $Y^6$ is of the following general formula: —$SiR^5_2$—O—[$SiR^1R^4$—O—]$_w$[$SiR^1R^0$—O—]$_x$[$SiR^1R^4$—O—]$_y$$SiR^5_2$—; wherein each of $Z_1$ and $Z_2$ is independently attributable to an organic amine having at least one amine group, each of $R^3$ and $R^{13}$ is independently a divalent group, each of $R^0$, $R^1$, $R^4$, and $R^5$ is independently a substituted or unsubstituted hydrocarbyl group, w is an integer selected from zero (0) to 1,000, x is an integer selected from 0 to 100, and y is an integer selected from 0 to 1,000.

Embodiment 21 relates to the composition as set forth in any one of Embodiments 3 to 20, wherein the elastomer is reacted with the at least one cosmetic component.

Embodiment 22 relates to the composition as set forth in any one of Embodiments 3 to 21, wherein the at least one cosmetic component is selected from emollients, waxes, moisturizers, surface active materials, thickeners, water phase stabilizing agents, pH controlling agents, preservatives and cosmetic biocides, sebum absorbants, sebum control agents, vegetable extracts, botanical extracts, vitamins, proteins and their derivatives, amino-acids and their derivatives, pigments, colorants, fillers, silicone conditioning agents, cationic conditioning agents, UV absorbers, sunscreen agents, antidandruff agents, antiperspirant agents, deodorant agents, skin protectants, hair dyes, nail care components, fragrances, perfumes, antioxidants, oxidizing agents, reducing agents, propellant gases, fatty alcohols, color care additives, pearlising agents, chelating agents, film formers, styling agents, ceramides, suspending agents, anti-aging actives, and combinations thereof.

Embodiment 23 relates to the composition as set forth in any one of the preceding Embodiments, which is in the form of a cream, a gel, a powder (free flowing powder or pressed), a paste, a solid, a freely pourable liquid, or an aerosol.

Embodiment 24 relates to the composition as set forth in any one of Embodiments 3 to 23, which is a lipstick, a foundation, a primer, a body cream, a face cream, a hair coloring product, a mascara, a color cosmetic, a nail varnish, an anti-wrinkle composition, an anti-aging composition, an eyeliner, an eyeshadow or a blush.

Embodiment 25 relates to the composition as set forth in any one of Embodiments 3 to 24, which is in the form of a shampoo, a cream, a rinse-off conditioner, a leave-in conditioner, a styling lotion, a styling spray or a gel.

Embodiment 26 relates to use of the composition according to any one of the preceding Embodiments for the care of keratinous substrates.

Embodiment 27 relates to a method of forming the composition as set forth in any one of Embodiments 3 to 25, the method comprising: combining the elastomer and the additive to form a mixture; and combining the mixture and the at least one cosmetic component to form a cosmetic composition; optionally in the presence of the cosmetically acceptable medium.

Embodiment 28 relates to the method as set forth in Embodiment 27, wherein the combining steps are separate.

Embodiment 29 relates to the preceding Embodiments, wherein the elastomer comprises the reaction product of: a first siloxane having at least one pendant anhydride group; a second siloxane having at least one pendant anhydride group; and a reactant comprising a polyol having at least two carbon-bonded hydroxyl groups reactive with the pendant anhydride groups of the first and second siloxanes.

Embodiment 30 relates to Embodiment 29, wherein the polyol is selected from the group of: i) an organic polyol having at least two carbon-bonded hydroxyl groups reactive with the pendant anhydride groups of the first and second siloxanes; ii) a third siloxane having at least two carbon-bonded hydroxyl groups reactive with the pendant anhydride groups of the first and second siloxanes; or iii) combinations thereof.

Embodiment 31 relates to Embodiment 30, wherein the polyol is the organic polyol and wherein: i) the organic polyol has two terminal carbon-bonded hydroxyl groups; and/or ii) the organic polyol is free of silicon.

Embodiment 32 relates to Embodiment 30, wherein the polyol is the third siloxane and the third siloxane has two terminal carbon-bonded hydroxyl groups.

Embodiment 33 relates to the preceding Embodiments, wherein the elastomer comprises the reaction product of: a first reactant having at least two hydroxyl groups; a second reactant having at least two hydroxyl groups; and a siloxane having at least two terminal anhydride groups reactive with the hydroxyl groups of the first and second reactants; wherein the first reactant is selected from the group of; i) a first siloxane different from the siloxane and having at least two hydroxyl groups, ii) a first organic alcohol having at least two hydroxyl groups, or iii) a combination thereof; and wherein the second reactant is selected from the group of; i) a second siloxane different from the siloxane and having at least two hydroxyl groups, ii) a second organic alcohol having at least two hydroxyl groups, or iii) a combination thereof.

Embodiment 34 relates to Embodiment 33, wherein: i) the first reactant comprises the first siloxane having at least two hydroxyl groups, alternatively at least two pendant hydroxyl groups; and/or ii) the second reactant comprises the second siloxane having at least two hydroxyl groups, alternatively at least two pendant hydroxyl groups.

Embodiment 35 relates to Embodiment 34, wherein: i) the first siloxane has at least three hydroxyl groups, alternatively at least three pendant hydroxyl groups; and/or ii) the second siloxane has at least three hydroxyl groups, alternatively at least three pendant hydroxyl groups.

Embodiment 36 relates to Embodiment 33, wherein: i) the first reactant comprises the first organic alcohol having at least two hydroxyl groups, alternatively at least three hydroxyl groups; and/or ii) the second reactant comprises the second organic alcohol having at least two hydroxyl groups, alternatively at least three hydroxyl groups.

Embodiment 37 relates to Embodiment 36, wherein: i) the first organic alcohol has at least one pendant hydroxyl group; and/or ii) the second organic alcohol has at least one pendant hydroxyl group.

Embodiment 38 relates to the preceding Embodiments, wherein the elastomer has at least two siloxy (Si—O) groups and at least two carboxyl groups, the elastomer comprising the reaction product of a reaction of: a first siloxane having at least one pendant anhydride group; a second siloxane having at least one pendant anhydride group; and a reactant selected from the group of; i) an organic polyol having at least two hydroxyl groups reactive with the pendant anhydride groups of the first and second siloxanes, and ii) a third siloxane having at least two hydroxyl groups reactive with the pendant anhydride groups of the first and second siloxanes.

Embodiment 39 relates to the preceding Embodiments, wherein the elastomer has at least two siloxy (Si—O) groups and at least two carboxyl groups, the elastomer comprising the reaction product of a reaction of: a first component having at least two hydroxyl groups; a second component having at least two hydroxyl groups; and a siloxane having at least two terminal anhydride groups reactive with the hydroxyl groups of the first and second components for linking the first component to the second component; wherein the first component is selected from the group of; i) a first siloxane different from the siloxane, and ii) a first organic alcohol; and wherein the second component is selected from the group of; i) a second siloxane different from the siloxane, and ii) a second organic alcohol.

The terms "comprising" or "comprise" are used herein in their broadest sense to mean and encompass the notions of "including," "include," "consist(ing) essentially of," and "consist(ing) of. The use of "for example," "e.g.," "such as," and "including" to list illustrative examples does not limit to only the listed examples. Thus, "for example" or "such as" means "for example, but not limited to" or "such as, but not limited to" and encompasses other similar or equivalent examples. The term "about" as used herein serves to reasonably encompass or describe minor variations in numerical values measured by instrumental analysis or as a result of sample handling. Such minor variations may be in the order of ±0-25, ±0-10, ±0-5, or ±0-2.5, % of the numerical values. Further, The term "about" applies to both numerical values when associated with a range of values. Moreover, the term "about" may apply to numerical values even when not explicitly stated.

Generally, as used herein a hyphen "-" or dash "—" in a range of values is "to" or "through"; a ">" is "above" or "greater-than"; a "≥" is "at least" or "greater-than or equal to"; a "<" is "below" or "less-than"; and a "≤" is "at most" or "less-than or equal to." On an individual basis, each of the aforementioned applications for patent, patents, and/or patent application publications, is expressly incorporated herein by reference in its entirety in one or more non-limiting embodiments.

It is to be understood that the appended claims are not limited to express and particular compounds, compositions, or methods described in the detailed description, which may vary between particular embodiments which fall within the scope of the appended claims. With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination and provides adequate support for specific embodiments within the scope of the appended claims.

It is also to be understood that any ranges and subranges relied upon in describing various embodiments of the present invention independently and collectively fall within the scope of the appended claims, and are understood to describe and contemplate all ranges including whole and/or fractional values therein, even if such values are not expressly written herein. One of skill in the art readily recognizes that the enumerated ranges and subranges sufficiently describe and enable various embodiments of the present invention, and such ranges and subranges may be further delineated into relevant halves, thirds, quarters, fifths, and so on. As just one example, a range "of from 0.1 to 0.9" may be further delineated into a lower third, i.e., from 0.1 to 0.3, a middle third, i.e., from 0.4 to 0.6, and an upper third, i.e., from 0.7 to 0.9, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 10" inherently includes a subrange of from at least 10 to 35, a subrange of from at least 10 to 25, a subrange of from 25 to 35, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range "of from 1 to 9" includes various individual integers, such as 3, as well as individual numbers including a decimal point (or fraction), such as 4.1, which may be relied upon and provide adequate support for specific embodiments within the scope of the appended claims.

The present invention has been described herein in an illustrative manner, and it is to be understood that the terminology which has been used is intended to be in the nature of words of description rather than of limitation. Many modifications and variations of the present invention are possible in light of the above teachings. The present invention may be practiced otherwise than as specifically described within the scope of the appended claims. The subject matter of all combinations of independent and dependent claims, both single and multiple dependent, is herein expressly contemplated.

What is claimed is:

1. A composition comprising:

(a) an elastomer; and (b) an additive comprising siloxane-based polyamide for stabilizing the elastomer;

wherein the elastomer is according to the general formula:

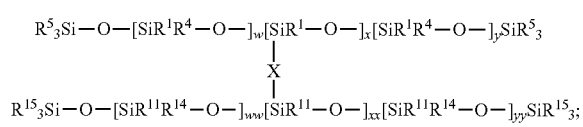

wherein each of $R^1$, $R^4$, $R^5$, $R^{11}$, $R^{14}$, and $R^{15}$ independently a substituted or unsubstituted hydrocarbyl group, each of w and ww is independently an integer from zero (0) to 1,000, each of x and xx is independently an integer from 1 to 100, each of y and yy is independently an integer from 0 to 1,000, and X is of the following general formula:

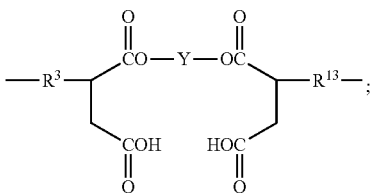

wherein each Y is a divalent group and wherein each of $R^3$ and $R^{13}$ is independently a divalent group.

2. The composition as set forth in claim 1, further defined as a cosmetic composition, wherein the cosmetic composition further comprises:
 (c) at least one cosmetic component;
 (d) optionally in a cosmetically acceptable medium.

3. The composition as set forth in claim 1, wherein the additive is solid at 25° C.

4. The composition as set forth in claim 1, wherein the additive is present in an amount of from about 0.01 to about 100 parts by weight based on 100 parts by weight of the elastomer.

5. A method of forming the composition as set forth claim 1, the method comprising:
 combining the elastomer and the additive to form a mixture; and
 combining the mixture and the at least one cosmetic component to form a cosmetic composition;
 optionally in the presence of the cosmetically acceptable medium.

6. The composition as set forth in claim 4, wherein the additive is present in an amount of from about 1 to about 50 parts by weight based on 100 parts by weight of the elastomer.

7. The composition as set forth in claim 2, wherein the cosmetically acceptable medium is present.

8. The composition as set forth in claim 2, wherein the elastomer is present in an amount of from about 0.1% to about 95% by weight relative to the total weight of the cosmetic composition.

9. The composition as set forth in claim 8, wherein the elastomer is present in an amount of from about 0.2% to about 50% by weight relative to the total weight of the cosmetic composition.

10. The composition as set forth in claim 1, wherein:
 each $R^1$, $R^5$, $R^{11}$, and $R^{15}$ is independently an alkyl group;
 each $R^4$ and $R^{14}$ is independently an alkyl group, a polyether group, or an anhydride group;
 each of w and ww is independently an integer from 50 to 150;
 each of x and xx is independently an integer from 1 to 10;
 each of y and yy is independently an integer from 1 to 50;
 Y comprises a divalent hydrocarbylene group having from 1 to 10 carbon atoms; and
 each of $R^3$ and $R^{13}$ is independently a divalent hydrocarbylene group having from 1 to 10 carbon atoms.

11. The composition as set forth in claim 2, wherein:
 each $R^1$, $R^5$, $R^{11}$, and $R^{15}$ is independently an alkyl group;
 each $R^4$ and $R^{14}$ is independently an alkyl group, a polyether group, or an anhydride group;
 each of w and ww is independently an integer from 50 to 150;
 each of x and xx is independently an integer from 1 to 10;
 each of y and yy is independently an integer from 1 to 50;
 Y comprises a divalent hydrocarbylene group having from 1 to 10 carbon atoms; and
 each of $R^3$ and $R^{13}$ is independently a divalent hydrocarbylene group having from 1 to 10 carbon atoms.

12. The method as set forth in claim 5, wherein the cosmetically acceptable medium is present.

* * * * *